US010844027B2

(12) United States Patent
Kruegel et al.

(10) Patent No.: US 10,844,027 B2
(45) Date of Patent: Nov. 24, 2020

(54) CARBOXYLIC DIARYLTHIAZEPINEAMINES AS MU-OPIOID RECEPTOR AGONISTS

(71) Applicants: Andrew Kruegel, Secaucus, NJ (US); Dalibor Sames, New York, NY (US); Madalee G. Wulf, Beverly, MA (US); Jonathan A. Javitch, Dobbs Ferry, NY (US)

(72) Inventors: Andrew Kruegel, Secaucus, NJ (US); Dalibor Sames, New York, NY (US); Madalee G. Wulf, Beverly, MA (US); Jonathan A. Javitch, Dobbs Ferry, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 15/759,706

(22) PCT Filed: Sep. 16, 2016

(86) PCT No.: PCT/US2016/052250
§ 371 (c)(1),
(2) Date: Mar. 13, 2018

(87) PCT Pub. No.: WO2017/049158
PCT Pub. Date: Mar. 23, 2017

(65) Prior Publication Data
US 2019/0047970 A1 Feb. 14, 2019

Related U.S. Application Data

(60) Provisional application No. 62/219,446, filed on Sep. 16, 2015.

(51) Int. Cl.
| C07D 281/16 | (2006.01) |
| C07D 281/02 | (2006.01) |
| A61P 25/36 | (2006.01) |
| A61K 31/485 | (2006.01) |
| A61P 25/24 | (2006.01) |

(52) U.S. Cl.
CPC ............ *C07D 281/16* (2013.01); *A61P 25/24* (2018.01); *A61P 25/36* (2018.01); *C07D 281/02* (2013.01); *A61K 31/485* (2013.01); *A61K 2300/00* (2013.01)

(58) Field of Classification Search
None
See application file for complete search history.

(56) References Cited

U.S. PATENT DOCUMENTS

| 3,657,276 A | 4/1972 | Malen et al. |
| 4,766,114 A | 8/1988 | Malen et al. |
| 5,238,936 A | 8/1993 | Regnier et al. |
| 8,337,941 B2 | 12/2012 | Gubernator et al. |
| 9,075,014 B2 | 7/2015 | Sames et al. |
| 9,988,377 B2 | 6/2018 | Sames et al. |
| 10,183,919 B2 | 2/2019 | Kruegel et al. |
| 2001/0037021 A1 | 11/2001 | Blanchard et al. |
| 2002/0198191 A1 | 12/2002 | Failli et al. |
| 2003/0082214 A1 | 5/2003 | Williams et al. |
| 2003/0092214 A1 | 5/2003 | Williams et al. |
| 2005/0227961 A1 | 10/2005 | Kucharik et al. |
| 2008/0194522 A1 | 8/2008 | Chen et al. |
| 2009/0209474 A1 | 8/2009 | Roegel et al. |
| 2010/0035279 A1 | 2/2010 | Gubernator et al. |
| 2012/0115849 A1 | 5/2012 | Demopulos et al. |
| 2013/0171664 A1 | 7/2013 | Sames et al. |
| 2013/0190497 A1 | 7/2013 | Gubernator et al. |
| 2015/0056699 A1 | 2/2015 | Sames et al. |
| 2017/0217913 A1 | 8/2017 | Kruegel et al. |
| 2019/0084949 A1 | 3/2019 | Kruegel et al. |
| 2019/0084983 A1 | 3/2019 | Kruegel et al. |

FOREIGN PATENT DOCUMENTS

| CN | 102977053 A | 3/2013 |
| GB | 1269551 A | 4/1972 |
| WO | WO 2001085680 A2 | 11/2001 |
| WO | WO 2006/023821 A2 | 3/2006 |
| WO | WO 2006/026368 A2 | 3/2006 |
| WO | WO 2007/022263 A1 | 2/2007 |
| WO | WO 2008/006828 A1 | 1/2008 |
| WO | WO 2008/009416 A1 | 1/2008 |
| WO | WO 2008/013997 A2 | 1/2008 |
| WO | WO 2009/059047 A2 | 5/2009 |
| WO | WO 2010/070667 A2 | 6/2010 |
| WO | WO 2011/094560 A1 | 8/2011 |
| WO | WO 2012/143703 A1 | 10/2012 |
| WO | WO 2013/028999 A1 | 2/2013 |

(Continued)

OTHER PUBLICATIONS

PCT International Application Publication No. WO 2010/070667 A2, published Jun. 24, 2010 to Biophore India Pharmaceutials Pvt Ltd (Exhibit 1).
International Search Report dated Feb. 3, 2017 in connection with PCT International Application No. PCT/US2016/052250 (Exhibit 2).
Written Opinion of the International Searching Authority dated Feb. 3, 2017 in connection with PCT International Application No. PCT/US2016/052250.
Office Action dated Feb. 15, 2019 in connection with European Patent Application EP15762391.9.
Office Action dated Jan. 15, 2018 in connection with Australian Patent Application No. 2015229258.
Gassaway, M. M. et al. (2014) "The atypical antidepressant and neurorestorative agent tianeptine is a mu-opioid receptor agonist", Translational Psychiatry,vol. 4, No. 7, p. e411.

(Continued)

*Primary Examiner* — Kamal A Saeed
(74) *Attorney, Agent, or Firm* — John P. White; Gary J. Gershik; Cooper & Dunham LLP

(57) ABSTRACT

The present invention provides a compound having the structure of the instant invention of a pharmaceutically acceptable salt or ester thereof, methods of preparing the same, and methods of treating a subject with compounds of the instant invention in combination therapies.

21 Claims, No Drawings

(56) References Cited

FOREIGN PATENT DOCUMENTS

| WO | WO 2013/029136 A1 | 3/2013 |
| WO | WO 2013/167906 A1 | 11/2013 |
| WO | WO 2015/138791 A1 | 9/2015 |
| WO | WO 2016/086158 A1 | 6/2016 |
| WO | WO 2007/017768 A2 | 2/2017 |
| WO | WO 2017/049158 A1 | 3/2017 |
| WO | WO 2017/165738 A1 | 9/2017 |
| WO | WO 2018/170275 A1 | 9/2018 |

OTHER PUBLICATIONS

International Search Report dated Feb. 3, 2017 in connection with PCT International Application No. PCT/US2016/052250.
International Search Report dated Jun. 18, 2015 in connection with International Application PCT/US2015/020273.
Written Opinion of the International Search Authority dated Jun. 18, 2015 in connection with International Application PCT/US2015/020273.
International Preliminary Report on Patentability dated Sep. 13, 2006 in connection with International Application No. PCT/US2015/020273.
Extended European Search Report dated Jul. 20, 2017 in connection with European Patent Application EP15762391.9.
Office Action dated May 29, 2018 in connection with Chinese Patent Application No. 201580025035.3, including English translation prepared by Chinese agent.
Office Action dated Dec. 4, 2018 in connection with Japanese Patent Application No. 201580025035.3, including English translation prepared by Japanese agent.
International Preliminary Report on Patentability dated Mar. 29, 2018 in connection with International Application No. PCT/US16/052250.
European Search Report dated Jan. 16, 2019 in connection with European Patent Application No. 16847444.3.
International Search Report dated Jun. 28, 2018 in connection with International Application No. PCT/US2018/022650.
Written Opinion of the International Search Authority dated Jun. 28, 2018 in connection with International Application No. PCT/US2018/022650.
Jamero et al., US Pharm. 2011; 36(5): HS4-HS8.
Diamond D.M. et al. (2004) "Preclinical research on stress, memory, and the brain in the development of pharmacotherapy for depression" European Neuropsychopharmacol, vol. 14, pp. S491-D495.
Labrid, C. et al. (1988) "Structure-activity relationships of tricyclic antidepressants, with special reference to tianeptine," Clinical Neuropharmacol, vol. 11, No. suppl. 2, pp. s21-s31.
STN Registry No. 887588-50-3, Jun. 13, 2006.
CAS Registry No. 1369502-93-1, Apr. 17, 2012.
Office Action dated Aug. 9, 2019 in connection with U.S. Appl. No. 16/193,814.
Office Action dated Feb. 20, 2019 in connection with Chinese Patent Application No. 201580025035.3, including English translation provided by Chinese agent.
Office Action dated Jan. 8, 2020 in connection with Australian Patent Application No. 2015229258.
Office Action dated Jan. 13, 2020 in connection with Australian Patent Application No. 2015229258.

CARBOXYLIC DIARYLTHIAZEPINEAMINES AS MU-OPIOID RECEPTOR AGONISTS

CROSS-REFERENCE TO RELATED APPLICATIONS

This application is a § 371 national stage of PCT International Application No. PCT/US2016/052250, filed Sep. 16, 2016, claiming the benefit of U.S. Provisional Application No. 62/219,446, filed Sep. 16, 2015, the contents of each of which are hereby incorporated by reference into the application.

Throughout this application, certain publications are referenced in parentheses. Full citations for these publications may be found immediately preceding the claims. The disclosures of these publications in their entireties are hereby incorporated by reference into this application in order to describe more fully the state of the art to which this invention relates.

BACKGROUND OF THE INVENTION

The mu-opioid receptor (MOR) has been the major molecular target for treatment of pain for several decades. However, the vast majority of MOR agonists used clinically today are structurally related to or derived from morphine (and other poppy alkaloids). These compounds suffer from many serious problems, including development of tolerance (increased dosing is required to achieve the same analgesic effects), high addiction liability, and other side effects (e.g., respiratory depression, nausea, and constipation) (Williams, J. T. et al. 2013). Therefore, there is a continuing interest in the development of new pain medications, including new MOR agonists with improved therapeutic profile (Corbett, A. D. et al. 2006).

There is also both historical and growing interest in the use of MOR agonists as medicaments for depression. Prior to the adoption of tricyclic antidepressants and electroshock therapy as favored treatments for depression, opiates were among the only options available, with the "opium cure" being an accepted treatment modality in the early 20th century (Berrocoso, E. et al. 2009). More recently, studies in both rodents (Besson, A. et al. 1996) and humans (Bodkin, J. A. et al. 1995) have suggested that MOR activation may lead to antidepressant and/or anxiolytic effects. The antidepressant tianeptine has also been reported to act as a full agonist of the MOR (Gassaway, M. M. et al. 2014). On the molecular level, MORs are extensively expressed in the hippocampus and have been shown to exert a variety of indirect modulatory effects on glutamatergic neurons in this brain region (Xie, C. W. et al. 1997; Svoboda, K. R. et al. 1999). Normalization and modulation of glutamate signaling has been strongly associated with the actions of antidepressants (Paul, I. A. and Skolnick, P. 2003) and indeed, the NMDA antagonist ketamine, shows rapid and efficacious antidepressant activity in human clinical trials (Zarate, C. A. Jr et al. 2006). Further, agonists of the related delta-opioid receptor (DOR) have been demonstrated to show robust antidepressant efficacy (Jutkiewicz, E. M. 2006).

Opioid receptor dysfunction may also be associated with borderline personality disorder (BPD). Patients afflicted with BPD exhibit alterations in both basal MOR binding potential and endogenous opioid responses to negative stimuli (Prossin, A. R. et al. 2010). There is also a high prevalence of BPD among patients seeking buprenorphine treatment for opioid addiction (Sansone, R. A. et al. 2008). Accordingly, MOR modulators may be useful medicaments for BPD.

Long-acting prescription opioids may also be used as maintenance (replacement) therapies in the treatment of opioid addiction. In this case, a prescription opioid is provided to the patient chronically and under medical supervision to substitute for the use of illicit opioids (e.g. heroin), thus reducing cravings for, and abuse of, the illicit drug. Opioid maintenance therapy is considered a standard method of care for opioid addiction and is more successful than behavioral or antagonist interventions (Bart, G. 2012).

Unfortunately, respiratory depression is a major liability associated with the use of MOR agonists (Pattinson, K. T. S. 2008). This side effect may complicate medical use of opioids both in the control of pain and alongside other medications that also depress respiration. Similarly, the primary cause of death in cases of acute opioid overdose is respiratory failure. Accordingly, methods of controlling or reversing opioid-induced respiratory depression associated with opioid use or overdose are of high interest. Likewise, new opioid analgesics with reduced potential to cause respiratory depression are also valuable. The standard of care for opioid-induced respiratory depression and overdose is administration of naloxone, an MOR antagonist (Wermeling, D. P. 2015). Although effective, naloxone treatment is associated with several important shortcomings. For one, naloxone also reverses the analgesic effects of MOR agonists and is thus inappropriate for use in settings where pain management is required (e.g. postoperatively). Naloxone administration also induces precipitated withdrawal symptoms, which although not typically life threatening, are extremely unpleasant for the patient. Lastly, naloxone is not orally bioavailable and exhibits a short half-life, meaning that it must be administered via parenteral routes and, when treating respiratory depression from long-acting opioids, continuously to overcome the short duration of action. Therefore, new therapeutic strategies to address opioid-induced respiratory depression or overdose without these shortcomings are desirable.

SUMMARY OF THE INVENTION

The present invention provides a compound having the structure:

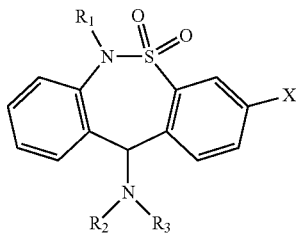

wherein
$R_1$ is —H or -(alkyl);
$R_2$ is -(alkyl)-$CO_2$H or -(alkyl)-$CO_2$-(alkyl);
$R_3$ is —H or -(alkyl); and
X is —Br or —I,
or a pharmaceutically acceptable salt or ester thereof.

The present invention further provides a process for producing the compound having the structure:

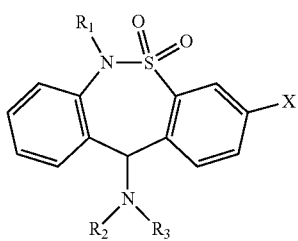

comprising
(a) contacting the compound having the structure:

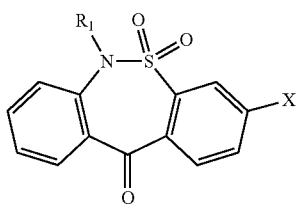

with a reducing agent in a first suitable solvent to produce a compound having the structure:

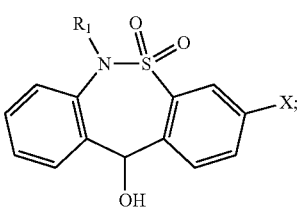

(b) reacting the product of step (a) with a halogenating agent, tosylating agent or triflating agent in a second suitable solvent so as to produce a compound having the structure:

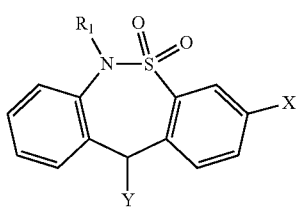

wherein Y is OTs, OTf, Cl, Br, or I;
(c) reacting the product of step (b) with an amine in the presence of a base in a third suitable solvent so as to produce the compound having the structure:

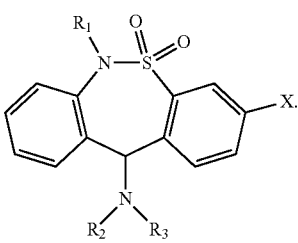

The present invention also provides a method of treating a subject afflicted with pain, a depressive disorder or a mood disorder comprising administering to the subject an effective amount of a DOR agonist or DOR antagonist and an effective amount of a compound having the structure:

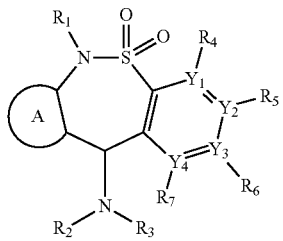

wherein

A is an aryl or heteroaryl, with or without substitution;

$R_1$ is —H or -(alkyl);

$R_2$ is -(alkyl), -(alkenyl), -(alkynyl), -(alkyl)-OH, -(alkyl)-$CO_2H$, -(alkyl)-$CO_2$-(alkyl), -(alkyl)-C(O)—$NH_2$, -(alkyl)-C(O)—NH(alkyl), -(alkyl)-C(O)—NH-(hydroxyalkyl), -(alkyl)-C(O)—N(alkyl)$_2$, -(alkyl)-C(O)—N(hydroxyalkyl)$_2$, -(alkyl)-O-(alkyl), -(alkyl)-S-(alkyl), -(alkyl)-$CF_3$, -(alkyl)-O-(hydroxyalkyl), -(alkyl)-O-(alkyl)-O-(alkyl), -(alkyl)-(CH)—(O-(alkyl))$_2$, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);

$R_3$ is —H or -(alkyl);

$R_4$, $R_5$, $R_6$ and $R_7$ are each absent or present, and when present, are each independently —H, —Cl, —Br, —F, —I, —CN, —$CF_3$, —$OCF_3$, -(alkyl), -(alkenyl), -(alkynyl), -(aryl), —$NH_2$, —NH-(alkyl), —NH-(alkenyl), —NH-(alkynyl)-NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), or —$SO_2$-(heteroaryl); and $Y_1$, $Y_2$, $Y_3$ and $Y_4$ are each independently N or C, wherein when $Y_1$ is N, then $R_4$ is absent, and when $Y_1$ is C, then $R_4$ is present; when $Y_2$ is N, then $R_5$ is absent, and when $Y_2$ is C, then $R_5$ is present; when $Y_3$ is N, then RE is absent, and when $Y_3$ is C, then $R_6$ is present; when $Y_4$ is N, then $R_7$ is absent, and when $Y_4$ is C, then $R_7$ is present, or a pharmaceutically acceptable salt thereof, so as to thereby treat the subject afflicted with pain, the depressive disorder or the mood disorder.

The present invention provides a method of treating a subject afflicted with borderline personality disorder, opioid addiction, opioid withdrawal symptoms, opioid-induced respiratory depression or opioid overdose comprising administering to the subject an effective amount of a compound having the structure:

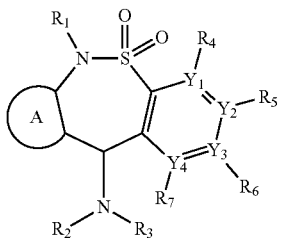

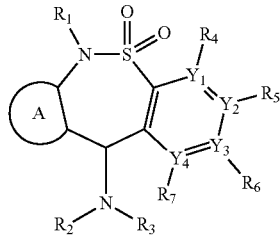

wherein

A is an aryl or heteroaryl, with or without substitution;

$R_1$ is —H or -(alkyl);

$R_2$ is -(alkyl), -(alkenyl), -(alkynyl), -(alkyl)-OH, -(alkyl)-$CO_2H$, -(alkyl)-$CO_2$-(alkyl), -(alkyl)-C(O)—$NH_2$, -(alkyl)-C(O)—NH(alkyl), -(alkyl)-C(O)—NH-(hydroxyalkyl), -(alkyl)-C(O)—N(alkyl)$_2$, -(alkyl)-C(O)—N(hydroxyalkyl)$_2$, -(alkyl)-O-(alkyl), -(alkyl)-S-(alkyl), -(alkyl)-$CF_3$, -(alkyl)-O-(hydroxyalkyl), -(alkyl)-O-(alkyl)-O-(alkyl), -(alkyl)-(CH)—(O-(alkyl))$_2$, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);

$R_3$ is —H or -(alkyl);

$R_4$, $R_5$, $R_6$ and $R_7$ are each absent or present, and when present, are each independently —H, —Cl, —Br, —F, —I, —CN, —$CF_3$, —$OCF_3$, -(alkyl), -(alkenyl), -(alkynyl), -(aryl), —$NH_2$, —NH-(alkyl), —NH-(alkenyl), —NH-(alkynyl)-NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), or —$SO_2$-(heteroaryl); and $Y_1$, $Y_2$, $Y_3$ and $Y_4$ are each independently N or C, wherein when $Y_1$ is N, then $R_4$ is absent, and when $Y_1$ is C, then $R_4$ is present; when $Y_2$ is N, then $R_5$ is absent, and when $Y_2$ is C, then $R_5$ is present; when $Y_3$ is N, then RE is absent, and when $Y_3$ is C, then $R_6$ is present; when $Y_4$ is N, then $R_7$ is absent, and when $Y_4$ is C, then $R_7$ is present, or a pharmaceutically acceptable salt thereof, so as to thereby treat the subject afflicted with the borderline personality disorder, opioid addiction, opioid withdrawal symptoms, opioid-induced respiratory depression or opioid overdose.

The present invention also provides a method of treating a subject afflicted with borderline personality disorder, opioid addiction, opioid withdrawal symptoms, opioid-induced respiratory depression or opioid overdose comprising administering to the subject an effective amount of an NMDA receptor antagonist, an NMDA receptor partial agonist, a neurokinin 1 receptor antagonist, a DOR agonist or a DOR antagonist and an effective amount of a compound having the structure:

wherein

A is an aryl or heteroaryl, with or without substitution;

$R_1$ is —H or -(alkyl);

$R_2$ is -(alkyl), -(alkenyl), -(alkynyl), -(alkyl)-OH, -(alkyl)-$CO_2H$, -(alkyl)-$CO_2$-(alkyl), -(alkyl)-C(O)—$NH_2$, -(alkyl)-C(O)—NH(alkyl), -(alkyl)-C(O)—NH-(hydroxyalkyl), -(alkyl)-C(O)—N(alkyl)$_2$, -(alkyl)-C(O)—N(hydroxyalkyl)$_2$, -(alkyl)-O-(alkyl), -(alkyl)-S-(alkyl), -(alkyl)-$CF_3$, -(alkyl)-O-(hydroxyalkyl), -(alkyl)-O-(alkyl)-O-(alkyl), -(alkyl)-(CH)—(O-(alkyl))$_2$, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);

$R_3$ is —H or -(alkyl);

$R_4$, $R_5$, $R_6$ and $R_7$ are each absent or present, and when present, are each independently —H, —Cl, —Br, —F, —I, —CN, —$CF_3$, —$OCF_3$, -(alkyl), -(alkenyl), -(alkynyl), -(aryl), —$NH_2$, —NH-(alkyl), —NH-(alkenyl), —NH-(alkynyl)-NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), or —$SO_2$-(heteroaryl); and $Y_1$, $Y_2$, $Y_3$ and $Y_4$ are each independently N or C, wherein when $Y_1$ is N, then $R_4$ is absent, and when $Y_1$ is C, then $R_4$ is present; when $Y_2$ is N, then $R_5$ is absent, and when $Y_2$ is C, then $R_5$ is present; when $Y_3$ is N, then $R_6$ is absent, and when $Y_3$ is C, then $R_6$ is present; when $Y_4$ is N, then $R_7$ is absent, and when $Y_4$ is C, then $R_7$ is present, or a pharmaceutically acceptable salt thereof, so as to thereby treat the subject afflicted with the borderline personality disorder, opioid addiction, opioid withdrawal symptoms, opioid-induced respiratory depression or opioid overdose.

The present invention further provides a method of treating a subject afflicted with pain, depressive disorder, a mood disorder, borderline personality disorder or opioid-induced respiratory depression, opioid overdose, opioid addiction, opioid withdrawal symptoms comprising administering to the subject an effective amount of naloxone or methylnaltrexone and an effective amount of a compound having the structure:

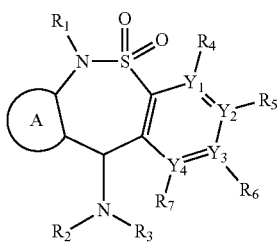

wherein
A is an aryl or heteroaryl, with or without substitution;
$R_1$ is —H or -(alkyl);
$R_2$ is -(alkyl), -(alkenyl), -(alkynyl), -(alkyl)-OH, -(alkyl)-$CO_2H$, -(alkyl)-$CO_2$-(alkyl), -(alkyl)-C(O)—$NH_2$, -(alkyl)-C(O)—NH(alkyl), -(alkyl)-C(O)—NH-(hydroxyalkyl), -(alkyl)-C(O)—N(alkyl)$_2$, -(alkyl)-C(O)—N(hydroxyalkyl)$_2$, -(alkyl)-O-(alkyl), -(alkyl)-S-(alkyl), -(alkyl)-$CF_3$, -(alkyl)-O-(hydroxyalkyl), -(alkyl)-O-(alkyl)-O-(alkyl), -(alkyl)-(CH)—(O-(alkyl))$_2$, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);
$R_3$ is —H or -(alkyl);
$R_4$, $R_5$, $R_6$ and $R_7$ are each absent or present, and when present, are each independently —H, —Cl, —Br, —F, —I, —CN, —$CF_3$, —$OCF_3$, -(alkyl), -(alkenyl), -(alkynyl), -(aryl), —$NH_2$, —NH-(alkyl), —NH-(alkenyl), —NH-(alkynyl)-NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), or —$SO_2$-(heteroaryl); and
$Y_1$, $Y_2$, $Y_3$ and $Y_4$ are each independently N or C,
wherein when $Y_1$ is N, then $R_4$ is absent, and when $Y_1$ is C, then $R_4$ is present; when $Y_2$ is N, then $R_5$ is absent, and when $Y_2$ is C, then $R_5$ is present; when $Y_3$ is N, then $R_6$ is absent, and when $Y_3$ is C, then $R_6$ is present; when $Y_4$ is N, then $R_7$ is absent, and when $Y_4$ is C, then $R_7$ is present,
for use in treating a subject afflicted with the pain, depressive disorder, a mood disorder, borderline personality disorder or opioid-induced respiratory depression, opioid overdose, opioid addiction, opioid withdrawal symptoms

DETAILED DESCRIPTION OF THE INVENTION

The present invention provides a compound having the structure:

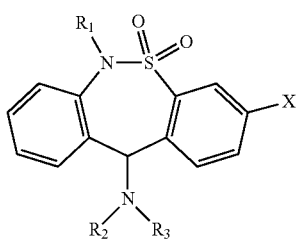

wherein
$R_1$ is —H or -(alkyl);
$R_2$ is -(alkyl)-$CO_2H$ or -(alkyl)-$CO_2$-(alkyl);
$R_3$ is —H or -(alkyl); and
X is —Br or —I,
or a pharmaceutically acceptable salt or ester thereof.
In some embodiments,
wherein
$R_1$ is —H or -(alkyl);
$R_2$ is —($C_2$-$C_5$ alkyl)-$CO_2H$ or —($C_2$-$C_5$ alkyl)-$CO_2$-(alkyl);
$R_3$ is —H or -(alkyl); and
X is —Br or —I.
In some embodiments,
wherein
$R_1$ is —H or -(alkyl);
$R_2$ is —($C_2$-$C_5$ alkyl)-$CO_2H$;
$R_3$ is —H or -(alkyl); and
X is —Br or —I.
In some embodiments,
wherein
$R_1$ is —H or -(alkyl);
$R_2$ is —($C_2$-$C_5$ alkyl)-$CO_2$-(alkyl);
$R_3$ is —H or -(alkyl); and
X is —Br or —I.
In some embodiments,
wherein
$R_1$ is —H or -(alkyl);
$R_2$ is —($C_2$-$C_5$ alkyl)-$CO_2CH_3$;
$R_3$ is —H or -(alkyl); and
X is —Br or —I.
In some embodiments,
wherein
$R_1$ is —H or -(alkyl);
$R_2$ is —($C_2$-$C_5$ alkyl)-$CO_2CH_2CH_3$;
$R_3$ is —H or -(alkyl); and
X is —Br or —I.
In some embodiments, wherein $R_1$ is —H, —$CH_3$ or —$CH_2CH_3$.
In some embodiments, wherein $R_3$ is —H, —$CH_3$ or —$CH_2CH_3$.
In some embodiments, wherein X is —Br.
In some embodiments, wherein X is —I.
In some embodiments,
wherein
$R_2$ is —($C_2$ alkyl)-$CO_2H$, —($C_3$ alkyl)-$CO_2H$, —($C_4$ alkyl)-$CO_2H$, or ($C_5$ alkyl)-$CO_2H$; and
$R_3$ is —H.
In some embodiments,
wherein
$R_2$ is —($C_2$ alkyl)-$CO_2CH_3$, —($C_3$ alkyl)-$CO_2CH_3$, —($C_4$ alkyl)-$CO_2CH_3$, or —($C_5$ alkyl)-$CO_2CH_3$; and
$R_3$ is —H.
In some embodiments,
wherein
$R_2$ is —($C_2$ alkyl)-$CO_2CH_2CH_3$—($C_3$ alkyl)-$CO_2CH_2CH_3$, —($C_4$ alkyl)-$CO_2CH_2CH_3$, or —($C_5$ alkyl)-$CO_2CH_2CH_3$; and
$R_3$ is —H.
In some embodiments,
wherein
$R_1$ is -(alkyl);
$R_2$ is -(alkyl)-$CO_2H$ or -(alkyl)-$CO_2$-(alkyl);
$R_3$ is —H; and
X is —Br or —I.

In some embodiments, wherein
wherein
$R_1$ is -(alkyl);
$R_2$ is —($C_2$-$C_5$ alkyl)-$CO_2$H or —($C_2$-$C_5$ alkyl)-$CO_2CH_3$;
$R_3$ is —H; and
X is —Br or I—,
or a pharmaceutically acceptable salt or ester thereof.

In some embodiments, wherein
wherein
$R_1$ is -(alkyl);
$R_2$ is —($C_2$-$C_5$ alkyl)-$CO_2$H or —($C_2$-$C_5$ alkyl)-$CO_2CH_2CH_3$;
$R_3$ is —H; and
X is —Br or I—,
or a pharmaceutically acceptable salt or ester thereof.

In some embodiments, the compound having the structure:

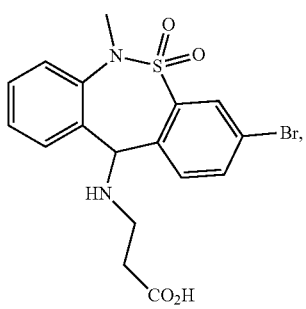

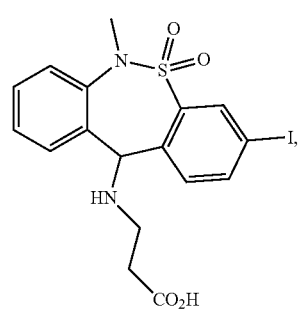

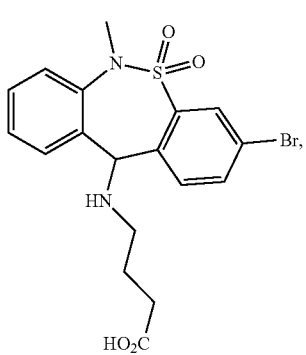

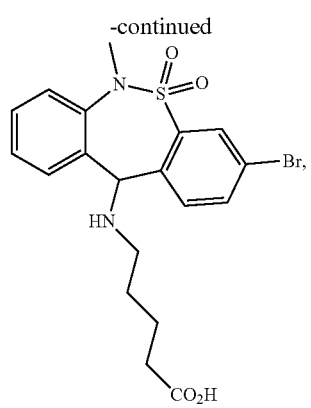

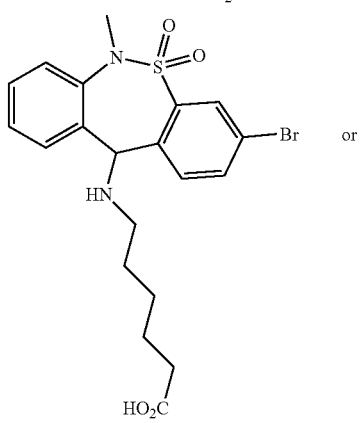

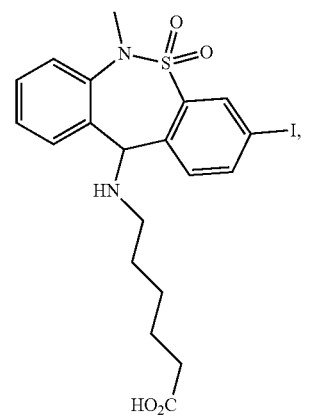

or a pharmaceutically acceptable salt or ester thereof.

In some embodiments, the compound having the structure:
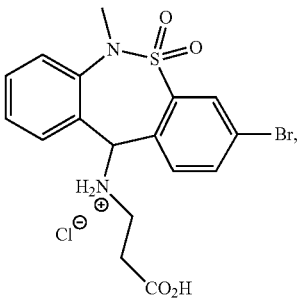
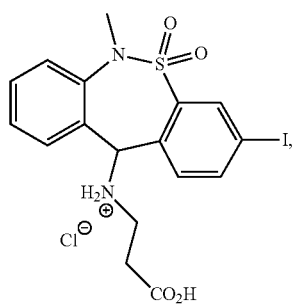
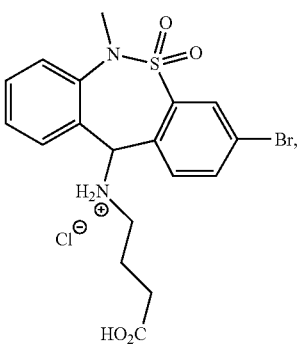
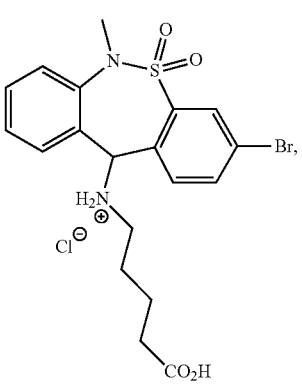
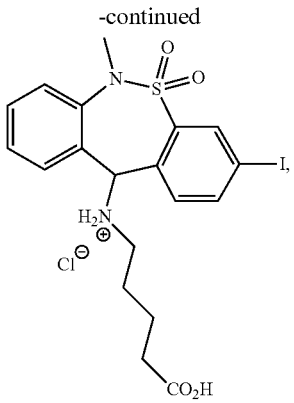
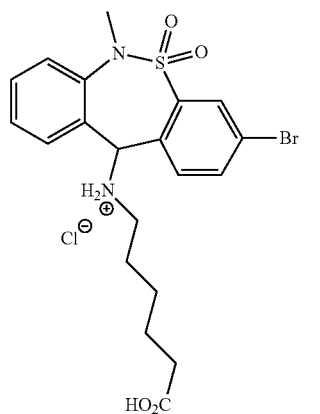
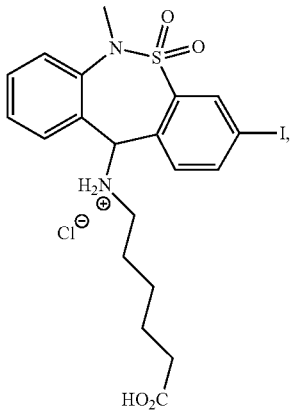
or a pharmaceutically acceptable salt or ester thereof.
In some embodiments, the compound having the structure:
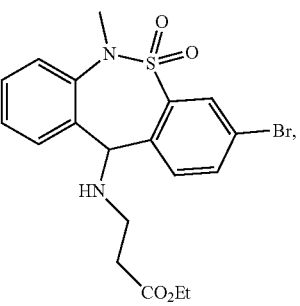

-continued

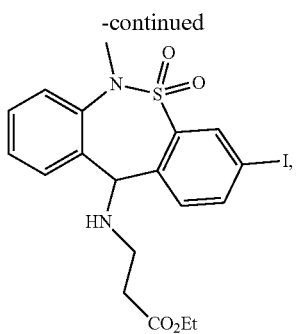

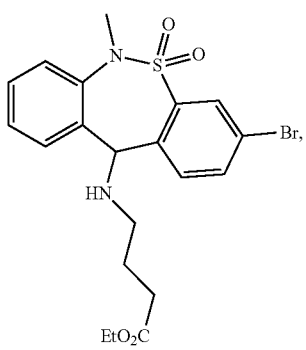

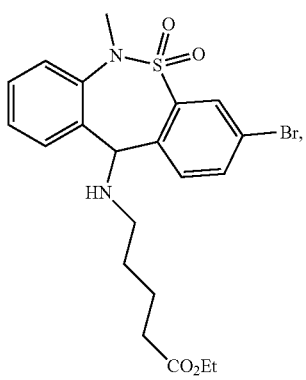

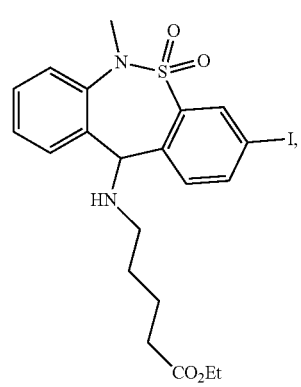

-continued

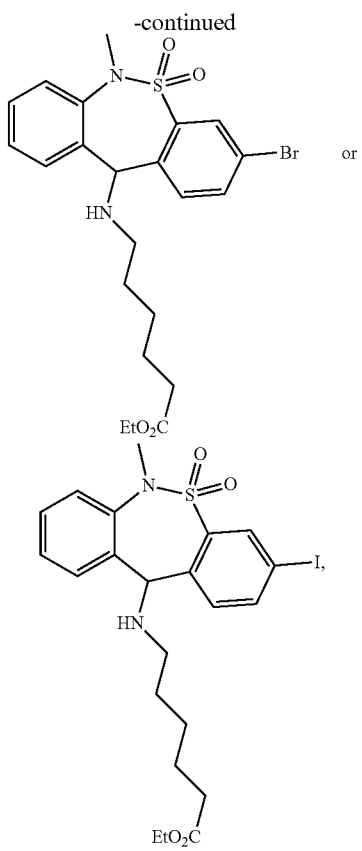

or a pharmaceutically acceptable salt or ester thereof.

In some embodiments, a pharmaceutical composition comprising the compound of the present invention and a pharmaceutically acceptable carrier.

In some embodiments, a method of activating a mu-opioid receptor or delta-opioid receptor comprising contacting the mu-opioid receptor or delta-opioid receptor with the compound of the present invention.

In some embodiments, a method of treating a subject afflicted with pain comprising administering an effective amount of the compound of the present invention to the subject so as to treat the subject afflicted with pain.

In some embodiments, a method of treating a subject afflicted with a depressive disorder comprising administering an effective amount of the compound of the present invention to the subject so as to treat the subject afflicted with the depressive disorder.

In some embodiments, a method of treating a subject afflicted with a mood disorder comprising administering an effective amount of the compound of the present invention to the subject so as to treat the subject afflicted with the mood disorder.

In some embodiments, a method of treating a subject afflicted with borderline personality disorder comprising administering an effective amount of the compound of the present invention to the subject so as to treat the subject afflicted with borderline personality disorder.

In some embodiments, a method of treating a subject afflicted with opioid addiction comprising administering an effective amount of the compound of the present invention to the subject so as to treat the subject afflicted with the opioid addiction.

In some embodiments, a method of treating a subject afflicted with opioid withdrawal symptoms comprising administering an effective amount of the compound of the present invention to the subject so as to treat the subject afflicted with the opioid withdrawal symptoms.

In some embodiments, a method of treating a subject afflicted with opioid-induced respiratory depression comprising administering an effective amount of the compound of the present invention to the subject so as to treat the subject afflicted with the opioid-induced respiratory depression.

In some embodiments, a method of treating a subject afflicted with opioid overdose comprising administering an effective amount of the compound of the present invention to the subject so as to treat the subject afflicted with the opioid overdose.

In some embodiments, a method of treating a subject afflicted with a pain comprising administering to the subject an effective amount of an NMDA receptor antagonist, an NMDA receptor partial agonist, a neurokinin 1 receptor antagonist or a DOR agonist and an effective amount of the compound of the present invention so as to thereby treat the subject afflicted with pain.

In some embodiments, a method of treating a subject afflicted with pain comprising administering to the subject an effective amount of DOR antagonist and an effective amount of the compound of the present invention so as to thereby treat the subject afflicted with pain.

In some embodiments, a method of treating a subject afflicted with a depressive disorder comprising administering to the subject an effective amount of a NMDA receptor antagonist, an NMDA receptor partial agonist, a neurokinin 1 receptor antagonist, a neurokinin 2 receptor antagonist, a neurokinin 3 receptor antagonist or a DOR agonist and an effective amount of the compound of the present invention so as to thereby treat the subject afflicted with the depressive disorder.

In some embodiments, a method of treating a subject afflicted with a depressive disorder comprising administering to the subject an effective amount of DOR antagonist and an effective amount of the compound of the present invention so as to thereby treat the subject afflicted with the depressive disorder.

In some embodiments, a method of treating a subject afflicted with a mood disorder comprising administering to the subject an effective amount of a NMDA receptor antagonist, an NMDA receptor partial agonist, a neurokinin 1 receptor antagonist, a neurokinin 2 receptor antagonist, a neurokinin 3 receptor antagonist or a DOR agonist and an effective amount of the compound of the present invention so as to thereby treat the subject afflicted with the mood disorder.

In some embodiments, a method of treating a subject afflicted with a mood disorder comprising administering to the subject an effective amount of DOR antagonist and an effective amount of the compound of the present invention so as to thereby treat the subject afflicted with the mood disorder.

In some embodiments, a method of treating a subject afflicted with borderline personality disorder comprising administering to the subject an effective amount of an NMDA receptor antagonist, an NMDA receptor partial agonist, a neurokinin 1 receptor antagonist, a DOR agonist or a DOR antagonist and an effective amount of a pharmaceutical composition comprising the compound of the present invention or a salt or ester thereof, so as to thereby treat the subject afflicted with borderline personality disorder.

In some embodiments, a method of treating a subject afflicted with opioid addiction comprising administering to the subject an effective amount of an NMDA receptor antagonist, an NMDA receptor partial agonist, a neurokinin 1 receptor antagonist or a DOR antagonist and an effective amount of a pharmaceutical composition comprising the compound of the present invention or a salt or ester thereof, so as to thereby treat the subject afflicted with the opioid addiction.

In some embodiments, a method of treating a subject afflicted with opioid withdrawal symptoms comprising administering to the subject an effective amount of an NMDA receptor antagonist, an NMDA receptor partial agonist, a neurokinin 1 receptor antagonist or a DOR antagonist and an effective amount of a pharmaceutical composition comprising the compound of the present invention or a salt or ester thereof, so as to thereby treat the subject afflicted with the opioid withdrawal symptoms.

In some embodiments, a method of treating a subject afflicted with opioid-induced respiratory depression comprising administering to the subject an effective amount of a DOR agonist or a DOR antagonist and an effective amount of a pharmaceutical composition comprising the compound of the present invention or a salt or ester thereof, so as to thereby treat the subject afflicted with the opioid-induced respiratory depression.

In some embodiments, a method of treating a subject afflicted with opioid overdose comprising administering to the subject an effective amount of a DOR agonist or a DOR antagonist and an effective amount of a pharmaceutical composition comprising the compound of the present invention or a salt or ester thereof, so as to thereby treat the subject afflicted with the opioid overdose.

The present invention further provides a process for producing the compound having the structure:

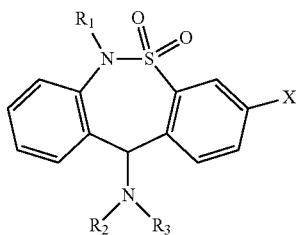

comprising (a) contacting the compound having the structure:

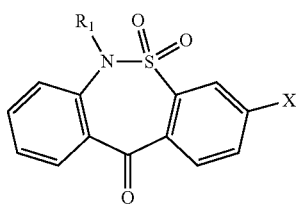

with a reducing agent in a first suitable solvent to produce a compound having the structure:

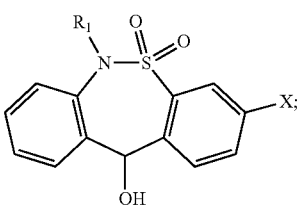

(b) reacting the product of step (a) with a halogenating agent or triflating agent in a second suitable solvent so as to produce a compound having the structure:

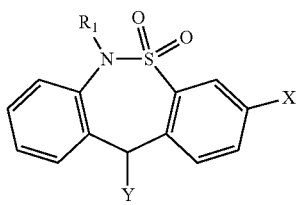

wherein Y is OTf, Cl, Br, or I;

(c) reacting the product of step (b) with an amine in the presence of a base in a third suitable solvent so as to produce the compound having the structure:

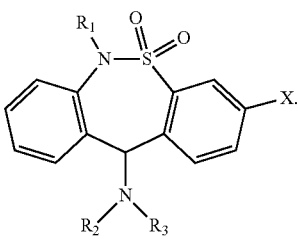

The present invention further provides a process for producing the compound having the structure:

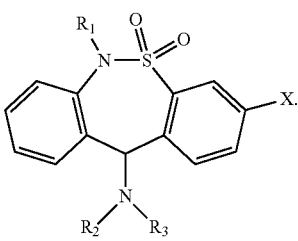

comprising
(a) contacting the compound having the structure:

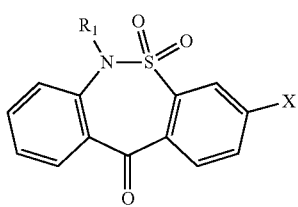

with a reducing agent in a first suitable solvent to produce a compound having the structure:

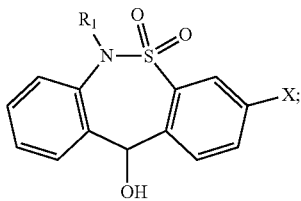

(b) reacting the product of step (a) with a halogenating agent, tosylating or triflating agent in a second suitable solvent so as to produce a compound having the structure:

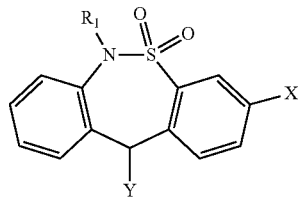

wherein Y is OTs, OTf, Cl, Br, or I;

(c) reacting the product of step (b) with an amine in the presence of a base in a third suitable solvent so as to produce the compound having the structure:

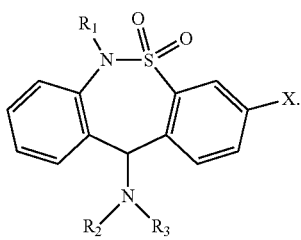

In some embodiments, the process wherein the reducing agent is sodium borohydride.

In some embodiments, the process wherein the halogenating agent is sulfonyl chloride or hydrogen chloride.

In some embodiments, the process wherein the halogenating agent is thionyl chloride or hydrogen chloride.

In some embodiments, the process wherein the amine is a primary amine or a secondary amine.

In some embodiments, the process wherein the first suitable solvent is methanol.

In some embodiments, the process wherein the second suitable solvent is dichloromethane.

In some embodiments, the process wherein the third suitable solvent is nitromethane.

The present invention yet further provides a method of treating a subject afflicted with pain, a depressive disorder or a mood disorder comprising administering to the subject an effective amount of a DOR agonist and an effective amount of a compound having the structure:

19

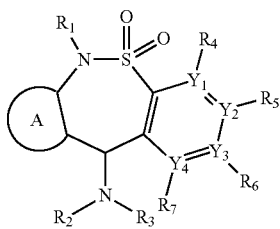

wherein
A is an aryl or heteroaryl, with or without substitution;
$R_1$ is —H or -(alkyl);
$R_2$ is -(alkyl), -(alkenyl), -(alkynyl), -(alkyl)-OH, -(alkyl)-$CO_2H$, -(alkyl)-$CO_2$-(alkyl), -(alkyl)-C(O)—$NH_2$, -(alkyl)-C(O)—NH(alkyl), -(alkyl)-C(O)—NH-(hydroxyalkyl), -(alkyl)-C(O)—N(alkyl)$_2$, -(alkyl)-C(O)—N(hydroxyalkyl)$_2$, -(alkyl)-O-(alkyl), -(alkyl)-S-(alkyl), -(alkyl)-$CF_3$, -(alkyl)-O-(hydroxyalkyl), -(alkyl)-O-(alkyl)-O-(alkyl), -(alkyl)-(CH)—(O-(alkyl))$_2$, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);
$R_3$ is —H or -(alkyl);
$R_4$, $R_5$, $R_6$ and $R_7$ are each absent or present, and when present, are each independently —H, —Cl, —Br, —F, —I, —CN, —$CF_3$, —$OCF_3$, -(alkyl), -(alkenyl), -(alkynyl), -(aryl), —$NH_2$, —NH-(alkyl), —NH-(alkenyl), —NH-(alkynyl)-NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), or —$SO_2$-(heteroaryl); and
$Y_1$, $Y_2$, $Y_3$ and $Y_4$ are each independently N or C,
wherein when $Y_1$ is N, then $R_4$ is absent, and when $Y_1$ is C, then $R_4$ is present; when $Y_2$ is N, then $R_5$ is absent, and when $Y_2$ is C, then $R_5$ is present; when $Y_3$ is N, then RE is absent, and when $Y_3$ is C, then $R_6$ is present; when $Y_4$ is N, then $R_7$ is absent, and when $Y_4$ is C, then $R_7$ is present,
or a pharmaceutically acceptable salt thereof, so as to thereby treat the subject afflicted with pain, the depressive disorder or the mood disorder.

The present invention yet further provides a method of treating a subject afflicted with borderline personality disorder, opioid addiction, opioid withdrawal symptoms, opioid-induced respiratory depression or opioid overdose comprising administering to the subject an effective amount of a compound having the structure:

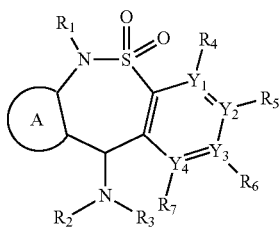

20 wherein
A is an aryl or heteroaryl, with or without substitution;
$R_1$ is —H or -(alkyl);
$R_2$ is -(alkyl), -(alkenyl), -(alkynyl), -(alkyl)-OH, -(alkyl)-$CO_2H$, -(alkyl)-$CO_2$-(alkyl), -(alkyl)-C(O)—$NH_2$, -(alkyl)-C(O)—NH(alkyl), -(alkyl)-C(O)—NH-(hydroxyalkyl), -(alkyl)-C(O)—N(alkyl)$_2$, -(alkyl)-C(O)—N(hydroxyalkyl)$_2$, -(alkyl)-O-(alkyl), -(alkyl)-S-(alkyl), -(alkyl)-$CF_3$, -(alkyl)-O-(hydroxyalkyl), -(alkyl)-O-(alkyl)-O-(alkyl), -(alkyl)-(CH)—(O-(alkyl))$_2$, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);
$R_3$ is —H or -(alkyl);
$R_4$, $R_5$, $R_6$ and $R_7$ are each absent or present, and when present, are each independently —H, —Cl, —Br, —F, —I, —CN, —$CF_3$, —$OCF_3$, -(alkyl), -(alkenyl), -(alkynyl), -(aryl), —$NH_2$, —NH-(alkyl), —NH-(alkenyl), —NH-(alkynyl)-NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), or —$SO_2$-(heteroaryl); and
$Y_1$, $Y_2$, $Y_3$ and $Y_4$ are each independently N or C,
wherein when $Y_1$ is N, then $R_4$ is absent, and when $Y_1$ is C, then $R_4$ is present; when $Y_2$ is N, then $R_5$ is absent, and when $Y_2$ is C, then $R_5$ is present; when $Y_3$ is N, then $R_6$ is absent, and when $Y_3$ is C, then $R_6$ is present; when $Y_4$ is N, then $R_7$ is absent, and when $Y_4$ is C, then $R_7$ is present,
or a pharmaceutically acceptable salt thereof, so as to thereby treat the subject afflicted with the borderline personality disorder, opioid addiction, opioid withdrawal symptoms, opioid-induced respiratory depression or opioid overdose.

The present invention yet further provides a method of treating a subject afflicted with borderline personality disorder comprising administering to the subject an effective amount of an NMDA receptor antagonist, an NMDA receptor partial agonist, a neurokinin 1 receptor antagonist, a DOR agonist or a DOR antagonist and an effective amount of a compound having the structure:

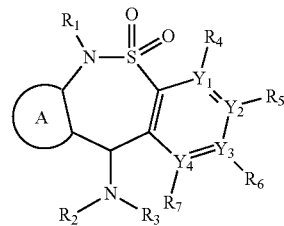

wherein
A is an aryl or heteroaryl, with or without substitution;
$R_1$ is —H or -(alkyl);
$R_2$ is -(alkyl), -(alkenyl), -(alkynyl), -(alkyl)-OH, -(alkyl)-$CO_2H$, -(alkyl)-$CO_2$-(alkyl), -(alkyl)-C(O)—$NH_2$, -(alkyl)-C(O)—NH(alkyl), -(alkyl)-C(O)—NH-(hydroxyalkyl), -(alkyl)-C(O)—N(alkyl)$_2$, -(alkyl)-C(O)—N(hydroxyalkyl)$_2$, -(alkyl)-O-(alkyl), -(alkyl)-S-(alkyl), -(alkyl)-$CF_3$, -(alkyl)-O-(hydroxyalkyl), -(alkyl)-O-(alkyl)-O-(alkyl), -(alkyl)-(CH)—(O-(alkyl))$_2$, -(alkyl)-(heterocyclyl), -(alkyl)-OAc, -(alkyl)-tetrahydrofuran, -(alkyl)-pyrrolidine, -(alkyl)-

N-methylpyrrolidine, -(alkyl)-(1,3-dioxane) or -(alkyl)-(4,5-dihydrooxazole);

$R_3$ is —H or -(alkyl);

$R_4$, $R_5$, $R_6$ and $R_7$ are each absent or present, and when present, are each independently —H, —Cl, —Br, —F, —I, —CN, —CF$_3$, —OCF$_3$, -(alkyl), -(alkenyl), -(alkynyl), -(aryl), —NH$_2$, —NH-(alkyl), —NH-(alkenyl), —NH-(alkynyl)-NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl), or —SO$_2$-(heteroaryl); and $Y_1$, $Y_2$, $Y_3$ and $Y_4$ are each independently N or C,
wherein when $Y_1$ is N, then $R_4$ is absent, and when $Y_1$ is C, then $R_4$ is present; when $Y_2$ is N, then $R_5$ is absent, and when $Y_2$ is C, then $R_5$ is present; when $Y_3$ is N, then $R_6$ is absent, and when $Y_3$ is C, then $R_6$ is present; when $Y_4$ is N, then $R_7$ is absent, and when $Y_4$ is C, then $R_7$ is present, or a pharmaceutically acceptable salt thereof, so as to thereby treat the subject afflicted with borderline personality disorder.

The present invention yet further provides a method of treating a subject afflicted with pain, a depressive disorder or a mood disorder comprising administering to the subject an effective amount of a DOR antagonist and an effective amount of a compound having the structure:

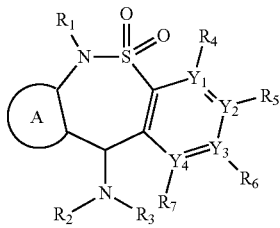

wherein

A is an aryl or heteroaryl, with or without substitution;

$R_1$ is —H or -(alkyl);

$R_2$ is -(alkyl), -(alkenyl), -(alkynyl), -(alkyl)-OH, -(alkyl)-CO$_2$H, -(alkyl)-CO$_2$-(alkyl), -(alkyl)-C(O)—NH$_2$, -(alkyl)-C(O)—NH(alkyl), -(alkyl)-C(O)—NH-(hydroxyalkyl), -(alkyl)-C(O)—N(alkyl)$_2$, -(alkyl)-C(O)—N(hydroxyalkyl)$_2$, -(alkyl)-O-(alkyl), -(alkyl)-S-(alkyl), -(alkyl)-CF$_3$, -(alkyl)-O-(hydroxyalkyl), -(alkyl)-O-(alkyl)-O-(alkyl), -(alkyl)-(CH)—(O-(alkyl))$_2$, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);

$R_3$ is —H or -(alkyl);

$R_4$, $R_5$, $R_6$ and $R_7$ are each absent or present, and when present, are each independently —H, —Cl, —Br, —F, —I, —CN, —CF$_3$, —OCF$_3$, -(alkyl), -(alkenyl), -(alkynyl), -(aryl), —NH$_2$, —NH-(alkyl), —NH-(alkenyl), —NH-(alkynyl)-NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl), or —SO$_2$-(heteroaryl); and $Y_1$, $Y_2$, $Y_3$ and $Y_4$ are each independently N or C,
wherein when $Y_1$ is N, then $R_4$ is absent, and when $Y_1$ is C, then $R_4$ is present; when $Y_2$ is N, then $R_5$ is absent, and when $Y_2$ is C, then $R_5$ is present; when $Y_3$ is N, then $R_6$ is absent, and when $Y_3$ is C, then $R_6$ is present; when $Y_4$ is N, then $R_7$ is absent, and when $Y_4$ is C, then $R_7$ is present, or a pharmaceutically acceptable salt thereof, so as to thereby treat the subject afflicted with pain, the depressive disorder or the mood disorder.

The present invention yet further provides a method of treating a subject afflicted with opioid addiction or opioid withdrawal symptoms comprising administering to the subject an effective amount of an NMDA receptor antagonist, an NMDA receptor partial agonist, a neurokinin 1 receptor antagonist or a DOR antagonist and an effective amount of a compound having the structure:

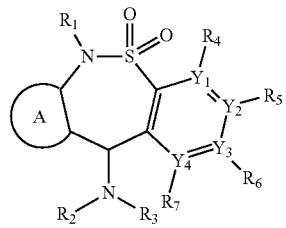

wherein

A is an aryl or heteroaryl, with or without substitution;

$R_1$ is —H or -(alkyl);

$R_2$ is -(alkyl), -(alkenyl), -(alkynyl), -(alkyl)-OH, -(alkyl)-CO$_2$H, -(alkyl)-CO$_2$-(alkyl), -(alkyl)-C(O)—NH$_2$, -(alkyl)-C(O)—NH(alkyl), -(alkyl)-C(O)—NH-(hydroxyalkyl), -(alkyl)-C(O)—N(alkyl)$_2$, -(alkyl)-C(O)—N(hydroxyalkyl)$_2$, -(alkyl)-O-(alkyl), -(alkyl)-S-(alkyl), -(alkyl)-CF$_3$, -(alkyl)-O-(hydroxyalkyl), -(alkyl)-O-(alkyl)-O-(alkyl), -(alkyl)-(CH)—(O-(alkyl))$_2$, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);

$R_3$ is —H or -(alkyl);

$R_4$, $R_5$, $R_6$ and $R_7$ are each absent or present, and when present, are each independently —H, —Cl, —Br, —F, —I, —CN, —CF$_3$, —OCF$_3$, -(alkyl), -(alkenyl), -(alkynyl), -(aryl), —NH$_2$, —NH-(alkyl), —NH-(alkenyl), —NH-(alkynyl)-NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl), or —SO$_2$-(heteroaryl); and $Y_1$, $Y_2$, $Y_3$ and $Y_4$ are each independently N or C,
wherein when $Y_1$ is N, then $R_4$ is absent, and when $Y_1$ is C, then $R_4$ is present; when $Y_2$ is N, then $R_5$ is absent, and when $Y_2$ is C, then $R_5$ is present; when $Y_3$ is N, then $R_6$ is absent, and when $Y_3$ is C, then $R_6$ is present; when $Y_4$ is N, then $R_7$ is absent, and when $Y_4$ is C, then $R_7$ is present, or a pharmaceutically acceptable salt thereof, so as to thereby treat the subject afflicted with the opioid addiction or opioid withdrawal symptoms.

The present invention yet further provides a method of treating a subject afflicted with opioid-induced respiratory depression or opioid overdose comprising administering to the subject an effective amount of a compound having the structure:

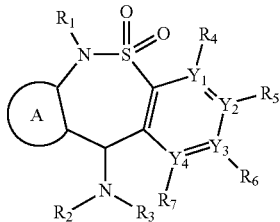

wherein
A is an aryl or heteroaryl, with or without substitution;
$R_1$ is —H or -(alkyl);
$R_2$ is -(alkyl), -(alkenyl), -(alkynyl), -(alkyl)-OH, -(alkyl)-$CO_2H$, -(alkyl)-$CO_2$-(alkyl), -(alkyl)-C(O)—$NH_2$, -(alkyl)-C(O)—NH(alkyl), -(alkyl)-C(O)—NH-(hydroxyalkyl), -(alkyl)-C(O)—N(alkyl)$_2$, -(alkyl)-C(O)—N(hydroxyalkyl)$_2$, -(alkyl)-O-(alkyl), -(alkyl)-S-(alkyl), -(alkyl)-$CF_3$, -(alkyl)-O-(hydroxyalkyl), -(alkyl)-O-(alkyl)-O-(alkyl), -(alkyl)-(CH)—(O-(alkyl))$_2$, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);
$R_3$ is —H or -(alkyl);
$R_4$, $R_5$, $R_6$ and $R_7$ are each absent or present, and when present, are each independently —H, —Cl, —Br, —F, —I, —CN, —$CF_3$, —$OCF_3$, -(alkyl), -(alkenyl), -(alkynyl), -(aryl), —$NH_2$, —NH-(alkyl), —NH-(alkenyl), —NH-(alkynyl)-NH-(aryl), —NH-(heteroaryl), —OH, —OAc, —O—C(O) (alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), or —$SO_2$-(heteroaryl); and
$Y_1$, $Y_2$, $Y_3$ and $Y_4$ are each independently N or C,
wherein when $Y_1$ is N, then $R_4$ is absent, and when $Y_1$ is C, then $R_4$ is present; when $Y_2$ is N, then $R_5$ is absent, and when $Y_2$ is C, then $R_5$ is present; when $Y_3$ is N, then $R_6$ is absent, and when $Y_3$ is C, then $R_6$ is present; when $Y_4$ is N, then $R_7$ is absent, and when $Y_4$ is C, then $R_7$ is present,
or a pharmaceutically acceptable salt thereof, so as to thereby treat the subject afflicted with the opioid-induced respiratory depression or opioid overdose.

The present invention yet further provides a method of treating a subject afflicted with opioid-induced respiratory depression or opioid overdose symptoms comprising administering to the subject an effective amount of a DOR agonist or a DOR antagonist and an effective amount of a compound having the structure:

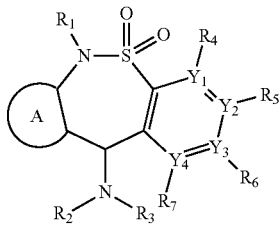

wherein
A is an aryl or heteroaryl, with or without substitution;
$R_1$ is —H or -(alkyl);
$R_2$ is -(alkyl), -(alkenyl), -(alkynyl), -(alkyl)-OH, -(alkyl)-$CO_2H$, -(alkyl)-$CO_2$-(alkyl), -(alkyl)-C(O)—$NH_2$, -(alkyl)-C(O)—NH(alkyl), -(alkyl)-C(O)—NH-(hydroxyalkyl), -(alkyl)-C(O)—N(alkyl)$_2$, -(alkyl)-C(O)—N(hydroxyalkyl)$_2$, -(alkyl)-O-(alkyl), -(alkyl)-S-(alkyl), -(alkyl)-$CF_3$, -(alkyl)-O-(hydroxyalkyl), -(alkyl)-O-(alkyl)-O-(alkyl), -(alkyl)-(CH)—(O-(alkyl))$_2$, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);
$R_3$ is —H or -(alkyl);
$R_4$, $R_5$, $R_6$ and $R_7$ are each absent or present, and when present, are each independently —H, —Cl, —Br, —F, —I, —CN, —$CF_3$, —$OCF_3$, -(alkyl), -(alkenyl), -(alkynyl), -(aryl), —$NH_2$, —NH-(alkyl), —NH-(alkenyl), —NH-(alkynyl)-NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), or —$SO_2$-(heteroaryl); and
$Y_1$, $Y_2$, $Y_3$ and $Y_4$ are each independently N or C,
wherein when $Y_1$ is N, then $R_4$ is absent, and when $Y_1$ is C, then $R_4$ is present; when $Y_2$ is N, then $R_5$ is absent, and when $Y_2$ is C, then $R_5$ is present; when $Y_3$ is N, then $R_6$ is absent, and when $Y_3$ is C, then $R_6$ is present; when $Y_4$ is N, then $R_7$ is absent, and when $Y_4$ is C, then $R_7$ is present,
or a pharmaceutically acceptable salt thereof, so as to thereby treat the subject afflicted with the opioid-induced respiratory depression or opioid overdose.

The present invention yet further provides a method of treating a subject afflicted with opioid overdose, opioid addiction or opioid withdrawal symptoms comprising administering to the subject an effective amount of naloxone or methylnaltrexone and an effective amount of a compound having the structure:

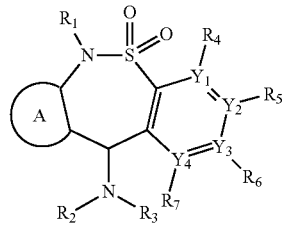

wherein
A is an aryl or heteroaryl, with or without substitution;
$R_1$ is —H or -(alkyl);
$R_2$ is -(alkyl), -(alkenyl), -(alkynyl), -(alkyl)-OH, -(alkyl)-$CO_2H$, -(alkyl)-$CO_2$-(alkyl), -(alkyl)-C(O)—$NH_2$, -(alkyl)-C(O)—NH(alkyl), -(alkyl)-C(O)—NH-(hydroxyalkyl), -(alkyl)-C(O)—N(alkyl)$_2$, -(alkyl)-C(O)—N(hydroxyalkyl)$_2$, -(alkyl)-O-(alkyl), -(alkyl)-S-(alkyl), -(alkyl)-$CF_3$, -(alkyl)-O-(hydroxyalkyl), -(alkyl)-O-(alkyl)-O-(alkyl), -(alkyl)-(CH)—(O-(alkyl))$_2$, -(alkyl)-(heterocyclyl), -(alkyl)-OAc, -(alkyl)-tetrahydrofuran, -(alkyl)-pyrrolidine, -(alkyl)-

N-methylpyrrolidine, -(alkyl)-(1,3-dioxane) or -(alkyl)-(4,5-dihydrooxazole);

R$_3$ is —H or -(alkyl);

R$_4$, R$_5$, R$_6$ and R$_7$ are each absent or present, and when present, are each independently —H, —Cl, —Br, —F, —I, —CN, —CF$_3$, —OCF$_3$, -(alkyl), -(alkenyl), -(alkynyl), -(aryl), —NH$_2$, —NH-(alkyl), —NH-(alkenyl), —NH-(alkynyl)-NH-(aryl), —NH-(heteroaryl), —OH, —OAc, —O—C(O) (alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl), or —SO$_2$-(heteroaryl); and Y$_1$, Y$_2$, Y$_3$ and Y$_4$ are each independently N or C,
wherein when Y$_1$ is N, then R$_4$ is absent, and when Y$_1$ is C, then R$_4$ is present; when Y$_2$ is N, then R$_5$ is absent, and when Y$_2$ is C, then R$_5$ is present; when Y$_3$ is N, then R$_6$ is absent, and when Y$_3$ is C, then R$_6$ is present; when Y$_4$ is N, then R$_7$ is absent, and when Y$_4$ is C, then R$_7$ is present, for use in treating a subject afflicted with the opioid overdose, opioid addiction or opioid withdrawal symptoms.

The present invention yet further provides a method of treating a subject afflicted with a pain, a depressive disorder, a mood disorder, borderline personality disorder or opioid-induced respiratory depression comprising administering to the subject an effective amount of naloxone or methylnaltrexone and an effective amount of a compound having the structure:

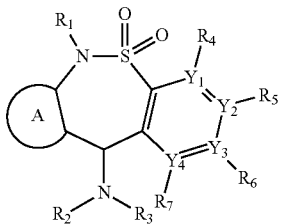

wherein

A is an aryl or heteroaryl, with or without substitution;

R$_1$ is —H or -(alkyl);

R$_2$ is -(alkyl), -(alkenyl), -(alkynyl), -(alkyl)-OH, -(alkyl)-CO$_2$H, -(alkyl)-CO$_2$-(alkyl), -(alkyl)-C(O)—NH$_2$, -(alkyl)-C(O)—NH(alkyl), -(alkyl)-C(O)—NH-(hydroxyalkyl), -(alkyl)-C(O)—N(alkyl)$_2$, -(alkyl)-C(O)—N(hydroxyalkyl)$_2$, -(alkyl)-O-(alkyl), -(alkyl)-S-(alkyl), -(alkyl)-CF$_3$, -(alkyl)-O-(hydroxyalkyl), -(alkyl)-O-(alkyl)-O-(alkyl), -(alkyl)-(CH)—(O-(alkyl))$_2$, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);

R$_3$ is —H or -(alkyl);

R$_4$, R$_5$, R$_6$ and R$_7$ are each absent or present, and when present, are each independently —H, —Cl, —Br, —F, —I, —CN, —CF$_3$, —OCF$_3$, -(alkyl), -(alkenyl), -(alkynyl), -(aryl), —NH$_2$, —NH-(alkyl), —NH-(alkenyl), —NH-(alkynyl)-NH-(aryl), —NH-(heteroaryl), —OH, —OAc, —O—C(O)(alkyl), —O-(alkyl), —O-(alkylaryl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl), or —SO$_2$-(heteroaryl); and Y$_1$, Y$_2$, Y$_3$ and Y$_4$ are each independently N or C,
wherein when Y$_1$ is N, then R$_4$ is absent, and when Y$_1$ is C, then R$_4$ is present; when Y$_2$ is N, then R$_5$ is absent, and when Y$_2$ is C, then R$_5$ is present; when Y$_3$ is N, then R$_6$ is absent, and when Y$_3$ is C, then R$_6$ is present; when Y$_4$ is N, then R$_7$ is absent, and when Y$_4$ is C, then R$_7$ is present, for use in treating a subject afflicted with the pain, depressive disorder, a mood disorder, borderline personality disorder or opioid-induced respiratory depression.

The above group of compounds, including specific compounds within the genus and synthetic methods for their preparation, are disclosed in PCT International Application No. PCT/US2015/020273, filed Mar. 12, 2015, the contents of which are hereby incorporated by reference.

In one embodiment of any of the compounds disclosed herein R$_2$ is —(C$_{2-5}$ alkyl)-CO$_2$H or any combination of any of —(C$_2$ alkyl)-CO$_2$H, —(C$_3$ alkyl)-CO$_2$H, —(C$_4$ alkyl)-CO$_2$H, or —(C$_5$ alkyl)-CO$_2$H.

In one embodiment of any of the compounds disclosed herein R$_2$ is —(C$_{2-5}$ alkyl)-CO$_2$-(alkyl) or any combination of any of —(C$_2$ alkyl)-C$_2$-(alkyl), —(C$_3$ alkyl)-CO$_2$-(alkyl), —(C$_4$ alkyl)-CO$_2$-(alkyl) or —(C$_5$ alkyl)-CO$_2$-(alkyl).

The present invention provides a pharmaceutical composition comprising the compound of the present invention and a pharmaceutically acceptable carrier.

The present invention provides a pharmaceutical composition comprising the compound of the present invention and a NMDA receptor antagonist, an NMDA receptor partial agonist, a neurokinin 1 receptor antagonist, a neurokinin 2 receptor antagonist, a neurokinin 3 receptor antagonist, a DOR agonist, a DOR antagonist, naloxone or methylnaltrexone and a pharmaceutically acceptable carrier.

The present invention provides a method of activating the mu-opioid receptor comprising contacting the mu-opioid receptor with the compound of the present invention.

The present invention provides a method of activating the delta-opioid receptor comprising contacting the delta-opioid receptor with the compound of the present invention.

The present invention provides a method of treating a subject afflicted with depression comprising administering an effective amount of the compound of the present invention to the subject so as to treat the subject afflicted with the depression.

The present invention provides a method of treating a subject afflicted with pain comprising administering an effective amount of the compound of the present invention to the subject so as to treat the subject afflicted with pain.

The present invention provides a method of treating a subject afflicted with anxiety comprising administering an effective amount of the compound of the present invention to the subject so as to treat the subject afflicted with the anxiety.

The present invention provides a method of treating a subject afflicted with borderline personality disorder comprising administering an effective amount of the compound of the present invention to the subject so as to treat the subject afflicted with borderline personality disorder.

The present invention provides a method of treating a subject afflicted with a depressive disorder comprising administering an effective amount of the compound of the present invention to the subject so as to treat the subject afflicted with the depressive disorder.

The present invention provides a method of treating a subject afflicted with a mood disorder comprising administering an effective amount of the compound of the present invention to the subject so as to treat the subject afflicted with the mood disorder.

The present invention provides a method of treating a subject afflicted with opioid addiction comprising administering an effective amount of the compound of the present invention to the subject so as to treat the subject afflicted with the opioid addiction.

The present invention provides a method of treating a subject afflicted with opioid withdrawal symptoms comprising administering an effective amount of the compound of the present invention to the subject so as to treat the subject afflicted with the opioid withdrawal symptoms.

The present invention provides a method of treating a subject afflicted with opioid-induced respiratory depression comprising administering an effective amount of the compound of the present invention to the subject so as to treat the subject afflicted with the opioid-induced respiratory depression.

The present invention provides a method of treating a subject afflicted with opioid overdose comprising administering an effective amount of the compound of the present invention to the subject so as to treat the subject afflicted with the opioid overdose.

In some embodiments, the mu-opioid receptors or delta-opioid receptors are in a human subject.

The present invention also provides a compound having the structure:

wherein
$R_1$ is —H or -(alkyl);
$R_2$ is -(alkyl)-$CO_2H$ or -(alkyl)-$CO_2$-(alkyl);
$R_3$ is —H or -(alkyl); and
X is —Br or —I,
or a salt or ester thereof, for use as an add-on therapy or in combination with an NMDA receptor antagonist, an NMDA receptor partial agonist, a neurokinin 1 receptor antagonist, a neurokinin 2 receptor antagonist, a neurokinin 3 receptor antagonist, or a DOR agonist in treating a subject afflicted with depression.

The present invention also provides a compound having the structure:

wherein
$R_1$ is —H or -(alkyl);
$R_2$ is -(alkyl)-$CO_2H$ or -(alkyl)-$CO_2$-(alkyl);
$R_3$ is —H or -(alkyl); and
X is —Br or —I,
or a salt or ester thereof, for use as an add-on therapy or in combination with an NMDA receptor antagonist, an NMDA receptor partial agonist, a neurokinin 1 receptor antagonist or a DOR agonist in treating a subject afflicted with pain.

The present invention also provides a compound having the structure:

wherein
$R_1$ is —H or -(alkyl);
$R_2$ is -(alkyl)-$CO_2H$ or -(alkyl)-$CO_2$-(alkyl);
$R_3$ is —H or -(alkyl); and
X is —Br or —I,
or a salt or ester thereof, for use as an add-on therapy or in combination with an NMDA receptor antagonist, an NMDA receptor partial agonist, a neurokinin 1 receptor antagonist, a neurokinin 2 receptor antagonist, a neurokinin 3 receptor antagonist, or a DOR agonist in treating a subject afflicted with a depressive disorder or mood disorder.

The present invention also provides a compound having the structure:

wherein
$R_1$ is —H or -(alkyl);
$R_2$ is -(alkyl)-$CO_2H$ or -(alkyl)-$CO_2$-(alkyl);
$R_3$ is —H or -(alkyl); and
X is —Br or —I,
or a salt or ester thereof, for use as an add-on therapy or in combination with a DOR antagonist in treating a subject afflicted with a depressive disorder or mood disorder.

The present invention also provides a compound having the structure:

[Chemical structure diagram]

wherein
R$_1$ is —H or -(alkyl);
R$_2$ is -(alkyl)-CO$_2$H or -(alkyl)-CO$_z$-(alkyl);
R$_3$ is —H or -(alkyl); and
X is —Br or —I,
or a salt or ester thereof, for use as an add-on therapy or in combination with a DOR antagonist in treating a subject afflicted with depression or pain.

The present invention also provides a compound having the structure:

[Chemical structure diagram]

wherein
R$_1$ is —H or -(alkyl);
R$_2$ is -(alkyl)-CO$_2$H or -(alkyl)-CO$_2$-(alkyl);
R$_3$ is —H or -(alkyl); and
X is —Br or —I,
or a salt or ester thereof, for use as an add-on therapy or in combination with an NMDA receptor antagonist, an NMDA receptor partial agonist, a neurokinin 1 receptor antagonist, a DOR agonist or a DOR antagonist in treating a subject afflicted with borderline personality disorder.

The present invention also provides a compound having the structure:

[Chemical structure diagram]

wherein
R$_1$ is —H or -(alkyl);
R$_2$ is -(alkyl)-CO$_2$H or -(alkyl)-CO$_2$-(alkyl);
R$_3$ is —H or -(alkyl); and
X is —Br or —I,
or a salt or ester thereof, for use as an add-on therapy or in combination with a DOR agonist or a DOR antagonist in treating a subject afflicted with opioid-induced respiratory depression.

The present invention also provides a compound having the structure:

[Chemical structure diagram]

wherein
R$_1$ is —H or -(alkyl);
R$_2$ is -(alkyl)-CO$_2$H or -(alkyl)-CO$_2$-(alkyl);
R$_3$ is —H or -(alkyl); and
X is —Br or —I,
or a salt or ester thereof, for use as an add-on therapy or in combination with an NMDA receptor antagonist, an NMDA receptor partial agonist, a neurokinin 1 receptor antagonist or a DOR antagonist in treating a subject afflicted with opioid addiction or opioid withdrawal symptoms.

The present invention also provides a compound having the structure:

[Chemical structure diagram]

wherein
R$_1$ is —H or -(alkyl);
R$_2$ is -(alkyl)-CO$_2$H or -(alkyl)-CO$_2$-(alkyl);
R$_3$ is —H or -(alkyl); and
X is —Br or —I,
or a salt or ester thereof, for use as an add-on therapy or in combination with a DOR agonist or a DOR antagonist in treating a subject afflicted with opioid overdose.

The present invention further provides a pharmaceutical composition comprising an amount of a compound having the structure:

[Chemical structure diagram]

wherein
R₁ is —H or -(alkyl);
R₂ is -(alkyl)-CO₂H or -(alkyl)-CO₂-(alkyl);
R₃ is —H or -(alkyl); and
X is —Br or —I, or a salt or ester thereof, and an amount of a NMDA receptor antagonist, an NMDA receptor partial agonist, a neurokinin 1 receptor antagonist, a neurokinin 2 receptor antagonist, a neurokinin 3 receptor antagonist, or a DOR agonist for use in treating a subject afflicted with depression.

The present invention further provides a pharmaceutical composition comprising an amount of a compound having the structure

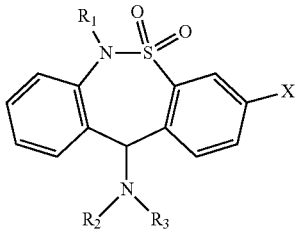

wherein
R₁ is —H or -(alkyl);
R₂ is -(alkyl)-CO₂H or -(alkyl)-CO₂-(alkyl);
R₃ is —H or -(alkyl); and
X is —Br or —I, or a salt or ester thereof, and an amount of a NMDA receptor antagonist, an NMDA receptor partial agonist, a neurokinin 1 receptor antagonist or a DOR agonist for use in treating a subject afflicted with pain.

The present invention further provides a pharmaceutical composition comprising an amount of a compound having the structure

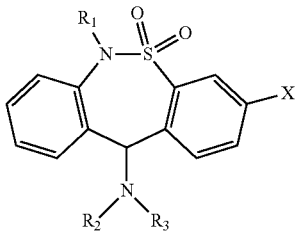

wherein
R₁ is —H or -(alkyl);
R₂ is -(alkyl)-CO₂H or -(alkyl)-CO₂-(alkyl);
R₃ is —H or -(alkyl); and
X is —Br or —I, or a salt or ester thereof, and an amount of a DOR antagonist for use in treating a subject afflicted with depression or pain.

The present invention further provides a pharmaceutical composition comprising an amount of a compound having the structure

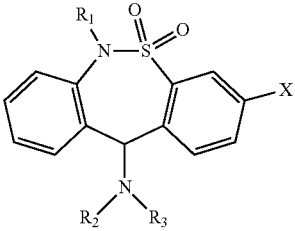

wherein
R₁ is —H or -(alkyl);
R₂ is -(alkyl)-CO₂H or -(alkyl)-CO₂-(alkyl);
R₃ is —H or -(alkyl); and
X is —Br or —I, or a salt or ester thereof, and an amount of a NMDA receptor antagonist, an NMDA receptor partial agonist, a neurokinin 1 receptor antagonist, a neurokinin 2 receptor antagonist, a neurokinin 3 receptor antagonist, or a DOR agonist for use in treating a subject afflicted with a depressive disorder or mood disorder.

The present invention further provides a pharmaceutical composition comprising an amount of a compound having the structure

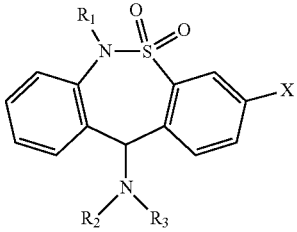

wherein
R₁ is —H or -(alkyl);
R₂ is -(alkyl)-CO₂H or -(alkyl)-CO₂-(alkyl);
R₃ is —H or -(alkyl); and
X is —Br or —I, or a salt or ester thereof, and an amount of a DOR antagonist for use in treating a subject afflicted with a depressive disorder or mood disorder.

The present invention further provides a pharmaceutical composition comprising an amount of a compound having the structure

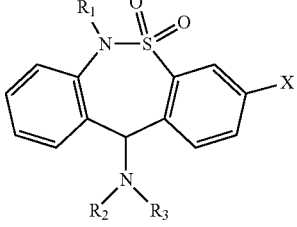

wherein
R₁ is —H or -(alkyl);
R₂ is -(alkyl)-CO₂H or -(alkyl)-CO₂-(alkyl);
R₃ is —H or -(alkyl); and
X is —Br or —I, or a salt or ester thereof, and an amount of a NMDA receptor antagonist, an NMDA receptor partial agonist, a neurokinin 1 receptor antagonist, a DOR agonist or a DOR antagonist in treating a subject afflicted with borderline personality disorder.

The present invention further provides a pharmaceutical composition comprising an amount of a compound having the structure

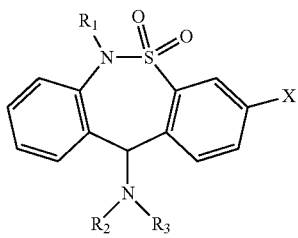

wherein
$R_1$ is —H or -(alkyl);
$R_2$ is -(alkyl)-$CO_2$H or -(alkyl)-$CO_2$-(alkyl);
$R_3$ is —H or -(alkyl); and
X is —Br or —I,
or a salt or ester thereof, and an amount of a DOR agonist or a DOR antagonist in treating a subject afflicted with opioid-induced respiratory depression.

The present invention further provides a pharmaceutical composition comprising an amount of a compound having the structure

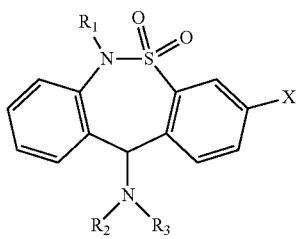

wherein
$R_1$ is —H or -(alkyl);
$R_2$ is -(alkyl)-$CO_2$H or -(alkyl)-$CO_2$-(alkyl);
$R_3$ is —H or -(alkyl); and
X is —Br or —I,
or a salt or ester thereof, and an amount of an NMDA receptor antagonist, an NMDA receptor partial agonist, a neurokinin 1 receptor antagonist or a DOR antagonist in treating a subject afflicted with opioid addiction or opioid withdrawal symptoms.

The present invention further provides a pharmaceutical composition comprising an amount of a compound having the structure

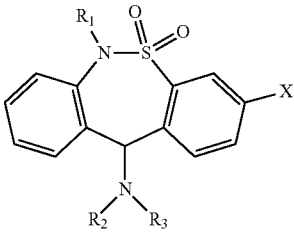

wherein
$R_1$ is —H or -(alkyl);
$R_2$ is -(alkyl)-$CO_2$H or -(alkyl)-$CO_2$-(alkyl);
$R_3$ is —H or -(alkyl); and
X is —Br or —I,
or a salt or ester thereof, and an amount of a DOR agonist or a DOR antagonist in treating a subject afflicted with opioid overdose.

The present invention also provides a compound having the structure:

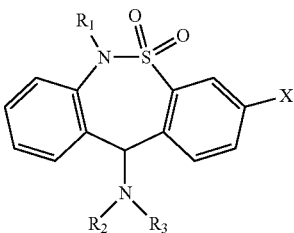

wherein
$R_1$ is —H or -(alkyl);
$R_2$ is -(alkyl)-$CO_2$H or -(alkyl)-$CO_2$-(alkyl);
$R_3$ is —H or -(alkyl); and
X is —Br or —I,
or a salt or ester thereof, for use as an add-on therapy or in combination with an SSRI or an SNRI in treating a subject afflicted with a depressive disorder, a mood disorder, or borderline personality disorder.

The present invention further provides a pharmaceutical composition comprising an amount of a compound having the structure

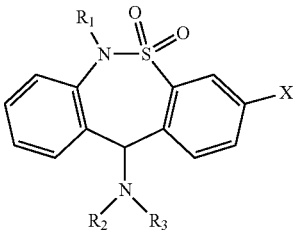

wherein
$R_1$ is —H or -(alkyl);
$R_2$ is -(alkyl)-$CO_2$H or -(alkyl)-$CO_2$-(alkyl);
$R_3$ is —H or -(alkyl); and
X is —Br or —I,
or a salt or ester thereof, and an amount of an SSRI or an SNRI in treating a subject afflicted with a depressive disorder, a mood disorder, or borderline personality disorder.

In some embodiments, a package comprising:
a) a first pharmaceutical composition comprising an amount of an NMDA receptor antagonist, an NMDA receptor partial agonist, a neurokinin 1 receptor antagonist or a DOR agonist and a pharmaceutically acceptable carrier;
b) a second pharmaceutical composition comprising an amount of any compound of the present invention, or a salt or ester thereof; and
c) instructions for use of the first and second pharmaceutical compositions together to treat a subject afflicted with pain.

In some embodiments, a package comprising:
a) a first pharmaceutical composition comprising an amount of a DOR antagonist and a pharmaceutically acceptable carrier;
b) a second pharmaceutical composition comprising an amount of any compound of the present invention, or a salt or ester thereof; and
c) instructions for use of the first and second pharmaceutical compositions together to treat a subject afflicted with pain.

In some embodiments, a package comprising:
a) a first pharmaceutical composition comprising an amount of an NMDA receptor antagonist, an NMDA receptor partial agonist, a neurokinin 1 receptor antagonist, a DOR agonist or a DOR antagonist and a pharmaceutically acceptable carrier;
b) a second pharmaceutical composition comprising an amount of any compound of the present invention, or a salt or ester thereof; and
c) instructions for use of the first and second pharmaceutical compositions together to treat a subject afflicted with borderline personality disorder.

In some embodiments, a package comprising:
a) a first pharmaceutical composition comprising an amount of a DOR agonist or a DOR antagonist and a pharmaceutically acceptable carrier;
b) a second pharmaceutical composition comprising an amount of any compound of the present invention, or a salt or ester thereof; and
c) instructions for use of the first and second pharmaceutical compositions together to treat a subject afflicted with opioid-induced respiratory depression.

In some embodiments, a package comprising:
a) a first pharmaceutical composition comprising an amount of an NMDA receptor antagonist, an NMDA receptor partial agonist, a neurokinin 1 receptor antagonist, or a DOR antagonist and a pharmaceutically acceptable carrier;
b) a second pharmaceutical composition comprising an amount of any compound of the present invention, or a salt or ester thereof; and
c) instructions for use of the first and second pharmaceutical compositions together to treat a subject afflicted with opioid addiction or opioid withdrawal symptoms.

In some embodiments, a package comprising:
a) a first pharmaceutical composition comprising an amount of a DOR agnostic or a DOR antagonist and a pharmaceutically acceptable carrier;
b) a second pharmaceutical composition comprising an amount of any compound of the present invention, or a salt or ester thereof; and
c) instructions for use of the first and second pharmaceutical compositions together to treat a subject afflicted with opioid overdose.

In some embodiments, a therapeutic package for dispensing to, or for use in dispensing to, a subject afflicted with pain, which comprises:
a) one or more unit doses, each such unit dose comprising:
(i) an amount of any compound of the present invention, or a salt or ester thereof; and
(ii) an amount of an NMDA receptor antagonist, an NMDA receptor partial agonist, a neurokinin 1 receptor antagonist or a DOR agonist,
wherein the respective amounts of said compound and said agonist or antagonist in said unit dose are effective, upon concomitant administration to said subject, to treat the subject, and
(b) a finished pharmaceutical container therefor, said container containing said unit dose or unit doses, said container further containing or comprising labeling directing the use of said package in the treatment of said subject.

In some embodiments, a therapeutic package for dispensing to, or for use in dispensing to, a subject afflicted with pain, which comprises:
a) one or more unit doses, each such unit dose comprising:
(i) an amount of any compound of the present invention, or a salt or ester thereof; and
(ii) an amount of a DOR antagonist,
wherein the respective amounts of said compound and said agonist or antagonist in said unit dose are effective, upon concomitant administration to said subject, to treat the subject, and
(b) a finished pharmaceutical container therefor, said container containing said unit dose or unit doses, said container further containing or comprising labeling directing the use of said package in the treatment of said subject.

In some embodiments, a therapeutic package for dispensing to, or for use in dispensing to, a subject afflicted with borderline personality disorder, which comprises:
a) one or more unit doses, each such unit dose comprising:
(i) an amount of any compound of the present invention, or a salt or ester thereof; and
(ii) an amount of an NMDA receptor antagonist, an NMDA receptor partial agonist, a neurokinin 1 receptor antagonist, a DOR agonist or a DOR antagonist,
wherein the respective amounts of said compound and said agonist or antagonist in said unit dose are effective, upon concomitant administration to said subject, to treat the subject, and
(b) a finished pharmaceutical container therefor, said container containing said unit dose or unit doses, said container further containing or comprising labeling directing the use of said package in the treatment of said subject.

In some embodiments, a therapeutic package for dispensing to, or for use in dispensing to, a subject afflicted with opioid-induced respiratory depression, which comprises:
a) one or more unit doses, each such unit dose comprising:
(i) an amount of any compound of the present invention, or a salt or ester thereof; and
(ii) an amount of a DOR agonist or a DOR antagonist,
wherein the respective amounts of said compound and said agonist or antagonist in said unit dose are effective, upon concomitant administration to said subject, to treat the subject, and
(b) a finished pharmaceutical container therefor, said container containing said unit dose or unit doses, said container further containing or comprising labeling directing the use of said package in the treatment of said subject.

In some embodiments, a therapeutic package for dispensing to, or for use in dispensing to, a subject afflicted with opioid addiction or opioid withdrawal symptoms, which comprises:
  a) one or more unit doses, each such unit dose comprising:
    (i) an amount of any compound of the present invention, or a salt or ester thereof; and
    (ii) an amount of an NMDA receptor antagonist, an NMDA receptor partial agonist, a neurokinin 1 receptor antagonist, or a DOR antagonist,
    wherein the respective amounts of said compound and said agonist or antagonist in said unit dose are effective, upon concomitant administration to said subject, to treat the subject, and
  (b) a finished pharmaceutical container therefor, said container containing said unit dose or unit doses, said container further containing or comprising labeling directing the use of said package in the treatment of said subject.

In some embodiments, a therapeutic package for dispensing to, or for use in dispensing to, a subject afflicted with opioid overdose, which comprises:
  a) one or more unit doses, each such unit dose comprising:
    (i) an amount of any compound of the present invention, or a salt or ester thereof; and
    (ii) an amount of a DOR agonist or a DOR antagonist, wherein the respective amounts of said compound and said agonist or antagonist in said unit dose are effective, upon concomitant administration to said subject, to treat the subject, and
  (b) a finished pharmaceutical container therefor, said container containing said unit dose or unit doses, said container further containing or comprising labeling directing the use of said package in the treatment of said subject.

The therapeutic package of the above embodiment, wherein the respective amounts of said compound and said agonist or antagonist in said unit dose when taken together is more effective to treat the subject than when compared to the administration of said compound in the absence of said agonist or antagonist or the administration of said agonist or antagonist in the absence of said compound.

A pharmaceutical composition in unit dosage form, useful in treating a subject afflicted with depression, major depression or pain, which comprises:
  (i) an amount of any compound of the present invention, or a salt or ester thereof; and
  (ii) an amount of an NMDA receptor antagonist, an NMDA receptor partial agonist, a neurokinin 1 receptor antagonist, a neurokinin 2 receptor antagonist, a neurokinin 3 receptor antagonist, or a DOR agonist,
  wherein the respective amounts of said compound and said agonist or antagonist in said composition are effective, upon concomitant administration to said subject of one or more of said unit dosage forms of said composition, to treat the subject.

A pharmaceutical composition in unit dosage form, useful in treating a subject afflicted with depression, major depression or pain, which comprises:
  (i) an amount of any compound of the present invention, or a salt or ester thereof; and
  (ii) an amount of a DOR antagonist,
  wherein the respective amounts of said compound and said agonist or antagonist in said composition are effective, upon concomitant administration to said subject of one or more of said unit dosage forms of said composition, to treat the subject.

The pharmaceutical composition of the above embodiment, wherein the respective amounts of said compound and said agonist or antagonist in said unit dose when taken together is more effective to treat the subject than when compared to the administration of said compound in the absence of said agonist or antagonist or the administration of said agonist or antagonist in the absence of said compound.

In some embodiments, a package comprising:
  a) a first pharmaceutical composition comprising an amount of an NMDA receptor antagonist, an NMDA receptor partial agonist, a neurokinin 1 receptor antagonist, a neurokinin 2 receptor antagonist, a neurokinin 3 receptor antagonist, or a DOR agonist and a pharmaceutically acceptable carrier;
  b) a second pharmaceutical composition comprising an amount of any compound of the present invention, or a salt or ester thereof; and
  c) instructions for use of the first and second pharmaceutical compositions together to treat a subject afflicted with a depressive disorder or mood disorder.

In some embodiments, a package comprising:
  a) a first pharmaceutical composition comprising a DOR antagonist and a pharmaceutically acceptable carrier;
  b) a second pharmaceutical composition comprising an amount of any compound of the present invention, or a salt or ester thereof; and
  c) instructions for use of the first and second pharmaceutical compositions together to treat a subject afflicted with a depressive disorder or mood disorder.

In some embodiments, a package comprising:
  a) a first pharmaceutical composition comprising an amount of an NMDA receptor antagonist, an NMDA receptor partial agonist, a neurokinin 1 receptor antagonist, a DOR agonist or a DOR antagonist and a pharmaceutically acceptable carrier;
  b) a second pharmaceutical composition comprising an amount of any compound of the present invention, or a salt or ester thereof; and
  c) instructions for use of the first and second pharmaceutical compositions together to treat a subject afflicted with borderline personality disorder.

In some embodiments, a package comprising:
  a) a first pharmaceutical composition comprising an amount of a DOR agonist or a DOR antagonist and a pharmaceutically acceptable carrier;
  b) a second pharmaceutical composition comprising an amount of any compound of the present invention, or a salt or ester thereof; and
  c) instructions for use of the first and second pharmaceutical compositions together to treat a subject afflicted with opioid-induced respiratory depression.

In some embodiments, a package comprising:
  a) a first pharmaceutical composition comprising an amount of an NMDA receptor antagonist, an NMDA receptor partial agonist, a neurokinin 1 receptor antagonist or a DOR antagonist and a pharmaceutically acceptable carrier;
  b) a second pharmaceutical composition comprising an amount of any compound of the present invention, or a salt or ester thereof; and
  c) instructions for use of the first and second pharmaceutical compositions together to treat a subject afflicted with opioid addiction or opioid withdrawal symptoms.

In some embodiments, a package comprising:
  a) a first pharmaceutical composition comprising an amount of a DOR agonist or a DOR antagonist and a pharmaceutically acceptable carrier;

b) a second pharmaceutical composition comprising an amount of any compound of the present invention, or a salt or ester thereof; and c) instructions for use of the first and second pharmaceutical compositions together to treat a subject afflicted with opioid overdose.

In some embodiments, a therapeutic package for dispensing to, or for use in dispensing to, a subject afflicted with a depressive disorder or mood disorder, which comprises:

a) one or more unit doses, each such unit dose comprising:
(i) an amount of any compound of the present invention, or a salt or ester thereof; and
(ii) an amount of an NMDA receptor antagonist, an NMDA receptor partial agonist, a neurokinin 1 receptor antagonist, a neurokinin 2 receptor antagonist, a neurokinin 3 receptor antagonist, or a DOR agonist,
wherein the respective amounts of said compound and said agonist or antagonist in said unit dose are effective, upon concomitant administration to said subject, to treat the subject, and (b) a finished pharmaceutical container therefor, said container containing said unit dose or unit doses, said container further containing or comprising labeling directing the use of said package in the treatment of said subject.

In some embodiments, a therapeutic package for dispensing to, or for use in dispensing to, a subject afflicted with a depressive disorder or mood disorder, which comprises:

a) one or more unit doses, each such unit dose comprising:
(i) an amount of any compound of the present invention, or a salt or ester thereof; and
(ii) an amount of a DOR antagonist,
wherein the respective amounts of said compound and said agonist or antagonist in said unit dose are effective, upon concomitant administration to said subject, to treat the subject, and (b) a finished pharmaceutical container therefor, said container containing said unit dose or unit doses, said container further containing or comprising labeling directing the use of said package in the treatment of said subject.

In some embodiments, a therapeutic package for dispensing to, or for use in dispensing to, a subject afflicted with borderline personality disorder, which comprises:

a) one or more unit doses, each such unit dose comprising:
(i) an amount of any compound of the present invention, or a salt or ester thereof; and
(ii) an amount of an NMDA receptor antagonist, an NMDA receptor partial agonist, a neurokinin 1 receptor antagonist, a DOR agonist or a DOR antagonist,
wherein the respective amounts of said compound and said agonist or antagonist in said unit dose are effective, upon concomitant administration to said subject, to treat the subject, and (b) a finished pharmaceutical container therefor, said container containing said unit dose or unit doses, said container further containing or comprising labeling directing the use of said package in the treatment of said subject.

In some embodiments, a therapeutic package for dispensing to, or for use in dispensing to, a subject afflicted with opioid-induced respiratory depression, which comprises:

a) one or more unit doses, each such unit dose comprising:
(i) an amount of any compound of the present invention, or a salt or ester thereof; and
(ii) an amount of a DOR agonist or a DOR antagonist,
wherein the respective amounts of said compound and said agonist or antagonist in said unit dose are effective, upon concomitant administration to said subject, to treat the subject, and (b) a finished pharmaceutical container therefor, said container containing said unit dose or unit doses, said container further containing or comprising labeling directing the use of said package in the treatment of said subject.

In some embodiments, a therapeutic package for dispensing to, or for use in dispensing to, a subject afflicted with opioid addiction or opioid withdrawal symptoms, which comprises:

a) one or more unit doses, each such unit dose comprising:
(i) an amount of any compound of the present invention, or a salt or ester thereof; and
(ii) an amount of an NMDA receptor antagonist, an NMDA receptor partial agonist, a neurokinin 1 receptor antagonist, or a DOR antagonist,
wherein the respective amounts of said compound and said agonist or antagonist in said unit dose are effective, upon concomitant administration to said subject, to treat the subject, and (b) a finished pharmaceutical container therefor, said container containing said unit dose or unit doses, said container further containing or comprising labeling directing the use of said package in the treatment of said subject.

In some embodiments, a therapeutic package for dispensing to, or for use in dispensing to, a subject afflicted with opioid overdose, which comprises:

a) one or more unit doses, each such unit dose comprising:
(i) an amount of any compound of the present invention, or a salt or ester thereof; and
(ii) an amount of a DOR agonist or a DOR antagonist,
wherein the respective amounts of said compound and said agonist or antagonist in said unit dose are effective, upon concomitant administration to said subject, to treat the subject, and (b) a finished pharmaceutical container therefor, said container containing said unit dose or unit doses, said container further containing or comprising labeling directing the use of said package in the treatment of said subject.

The therapeutic package of the above embodiment, wherein the respective amounts of said compound and said agonist or antagonist in said unit dose when taken together is more effective to treat the subject than when compared to the administration of said compound in the absence of said agonist or antagonist or the administration of said agonist or antagonist in the absence of said compound.

A pharmaceutical composition in unit dosage form, useful in treating a subject afflicted with a depressive disorder or mood disorder, which comprises:

(i) an amount of any compound of the present invention, or a salt or ester thereof; and
(ii) an amount of an NMDA receptor antagonist, an NMDA receptor partial agonist, a neurokinin 1 receptor antagonist, a neurokinin 2 receptor antagonist, a neurokinin 3 receptor antagonist, or a DOR agonist,
wherein the respective amounts of said compound and said agonist or antagonist in said composition are effective, upon concomitant administration to said subject of one or more of said unit dosage forms of said composition, to treat the subject.

A pharmaceutical composition in unit dosage form, useful in treating a subject afflicted with a depressive disorder or mood disorder, which comprises:

(i) an amount of any compound of the present invention, or a salt or ester thereof; and
(ii) an amount of a DOR antagonist,
wherein the respective amounts of said compound and said agonist or antagonist in said composition are effective, upon concomitant administration to said subject of one or more of said unit dosage forms of said composition, to treat the subject.

A pharmaceutical composition in unit dosage form, useful in treating a subject afflicted with borderline personality disorder, which comprises:
  (i) an amount of any compound of the present invention, or a salt or ester thereof; and
  (ii) an amount of an NMDA receptor antagonist, an NMDA receptor partial agonist, a neurokinin 1 receptor antagonist, a DOR agonist or a DOR antagonist,
  wherein the respective amounts of said compound and said agonist or antagonist in said composition are effective, upon concomitant administration to said subject of one or more of said unit dosage forms of said composition, to treat the subject.

A pharmaceutical composition in unit dosage form, useful in treating a subject afflicted with opioid-induced respiratory depression, which comprises:
  (i) an amount of any compound of the present invention, or a salt or ester thereof; and
  (ii) an amount of a DOR agonist or a DOR antagonist,
  wherein the respective amounts of said compound and said agonist or antagonist in said composition are effective, upon concomitant administration to said subject of one or more of said unit dosage forms of said composition, to treat the subject.

A pharmaceutical composition in unit dosage form, useful in treating a subject afflicted with opioid addiction or opioid withdrawal symptoms, which comprises:
  (i) an amount of any compound of the present invention, or a salt or ester thereof; and
  (ii) an amount of an NMDA receptor antagonist, an NMDA receptor partial agonist, a neurokinin 1 receptor antagonist, or a DOR antagonist,
  wherein the respective amounts of said compound and said agonist or antagonist in said composition are effective, upon concomitant administration to said subject of one or more of said unit dosage forms of said composition, to treat the subject.

A pharmaceutical composition in unit dosage form, useful in treating a subject afflicted with opioid overdose, which comprises:
  (i) an amount of any compound of the present invention, or a salt or ester thereof; and
  (ii) an amount of a DOR agonist or a DOR antagonist,
  wherein the respective amounts of said compound and said agonist or antagonist in said composition are effective, upon concomitant administration to said subject of one or more of said unit dosage forms of said composition, to treat the subject.

The pharmaceutical composition of the above embodiment, wherein the respective amounts of said compound and said agonist or antagonist in said unit dose when taken together is more effective to treat the subject than when compared to the administration of said compound in the absence of said agonist or antagonist or the administration of said agonist or antagonist in the absence of said compound.

The present invention also provides a method of treating a subject afflicted with a pain, depressive disorder, a mood disorder, or borderline personality disorder comprising administering to the subject an effective amount of an SSRI or an SNRI and an effective amount of any compound of the present invention, or a salt or ester thereof, so as to thereby treat the subject.

The present invention also provides a compound of the present invention or a salt or ester thereof, for use as an add-on therapy or in combination with an SSRI or an SNRI in treating a subject afflicted with a depressive disorder, a mood disorder, or borderline personality disorder.

The present invention further provides a pharmaceutical composition comprising an amount of any of the compounds of the present invention, or a salt or ester thereof, and an amount of an SSRI or an SNRI for use in treating a subject afflicted with pain, a depressive disorder, a mood disorder, or borderline personality disorder.

The present invention also provides a method of treating a subject afflicted with a depressive disorder or mood disorder comprising administering to the subject an effective amount of an NMDA receptor antagonist, an NMDA receptor partial agonist, a neurokinin 1 receptor antagonist, a neurokinin 2 receptor antagonist, a neurokinin 3 receptor antagonist, or a DOR agonist and an effective amount of any compound of the present invention, or a salt or ester thereof, so as to thereby treat the subject.

The present invention also provides a compound of the present invention or a salt or ester thereof, for use as an add-on therapy or in combination with an NMDA receptor antagonist, an NMDA receptor partial agonist, a neurokinin 1 receptor antagonist, a neurokinin 2 receptor antagonist, neurokinin 3 receptor antagonist, or a DOR agonist in treating a subject afflicted with a depressive disorder or mood disorder.

The present invention further provides a pharmaceutical composition comprising an amount of any of the compounds of the present invention, or a salt or ester thereof, and an amount of an NMDA receptor antagonist, an NMDA receptor partial agonist, a neurokinin 1 receptor antagonist, a neurokinin 2 receptor antagonist, a neurokinin 3 receptor antagonist, or a DOR agonist for use in treating a subject afflicted with a depressive disorder or mood disorder.

The present invention also provides a method of treating a subject afflicted with a depressive disorder or mood disorder comprising administering to the subject an effective amount of an NMDA receptor antagonist and an effective amount of any compound of the present invention, or a salt or ester thereof, so as to thereby treat the subject.

The present invention also provides a compound of the present invention or a salt or ester thereof, for use as an add-on therapy or in combination with an NMDA receptor antagonist, in treating a subject afflicted with a depressive disorder or mood disorder.

The present invention further provides a pharmaceutical composition comprising an amount of any of the compounds of the present invention, or a salt or ester thereof, and an amount of an NMDA receptor antagonist, for use in treating a subject afflicted with a depressive disorder or mood disorder.

The present invention also provides a method of treating a subject afflicted with a depressive disorder or mood disorder comprising administering to the subject an effective amount of an NMDA receptor partial agonist, and an effective amount of any compound of the present invention, or a salt or ester thereof, so as to thereby treat the subject.

The present invention also provides a compound of the present invention or a salt or ester thereof, for use as an add-on therapy or in combination with an NMDA receptor partial agonist in treating a subject afflicted with a depressive disorder or mood disorder.

The present invention further provides a pharmaceutical composition comprising an amount of any of the compounds of the present invention, or a salt or ester thereof, and an amount of an NMDA receptor partial agonist, for use in treating a subject afflicted with a depressive disorder or mood disorder.

The present invention also provides a method of treating a subject afflicted with a depressive disorder or mood disorder comprising administering to the subject an effective amount of a neurokinin 1 receptor antagonist and an effective amount of any compound of the present invention, or a salt or ester thereof, so as to thereby treat the subject.

The present invention also provides a compound of the present invention or a salt or ester thereof, for use as an add-on therapy or in combination with a neurokinin 1 receptor antagonist in treating a subject afflicted with a depressive disorder or mood disorder.

The present invention further provides a pharmaceutical composition comprising an amount of any of the compounds of the present invention, or a salt or ester thereof, and an amount of a neurokinin 1 receptor antagonist for use in treating a subject afflicted with a depressive disorder or mood disorder.

The present invention also provides a method of treating a subject afflicted with a depressive disorder or mood disorder comprising administering to the subject an effective amount of a neurokinin 2 receptor antagonist and an effective amount of any compound of the present invention, or a salt or ester thereof, so as to thereby treat the subject.

The present invention also provides a compound of the present invention or a salt or ester thereof, for use as an add-on therapy or in combination with a neurokinin 2 receptor antagonist in treating a subject afflicted with a depressive disorder or mood disorder.

The present invention further provides a pharmaceutical composition comprising an amount of any of the compounds of the present invention, or a salt or ester thereof, and an amount of a neurokinin 2 receptor antagonist for use in treating a subject afflicted with a depressive disorder or mood disorder.

The present invention also provides a method of treating a subject afflicted with a depressive disorder or mood disorder comprising administering to the subject an effective amount of a neurokinin 3 receptor antagonist and an effective amount of any compound of the present invention, or a salt or ester thereof, so as to thereby treat the subject.

The present invention also provides a compound of the present invention or a salt or ester thereof, for use as an add-on therapy or in combination with a neurokinin 3 receptor antagonist in treating a subject afflicted with a depressive disorder or mood disorder.

The present invention further provides a pharmaceutical composition comprising an amount of any of the compounds of the present invention, or a salt or ester thereof, and an amount of a neurokinin 3 receptor antagonist for use in treating a subject afflicted with a depressive disorder or mood disorder.

The present invention also provides a method of treating a subject afflicted with a depressive disorder or mood disorder comprising administering to the subject an effective amount of a DOR agonist and an effective amount of any compound of the present invention, or a salt or ester thereof, so as to thereby treat the subject.

The present invention also provides a compound of the present invention or a salt or ester thereof, for use as an add-on therapy or in combination with a DOR agonist in treating a subject afflicted with a depressive disorder or mood disorder.

The present invention further provides a pharmaceutical composition comprising an amount of any of the compounds of the present invention, or a salt or ester thereof, and an amount of a DOR agonist for use in treating a subject afflicted with a depressive disorder or mood disorder.

The present invention also provides a method of treating a subject afflicted with pain comprising administering to the subject an effective amount of an NMDA receptor antagonist and an effective amount of any compound of the present invention, or a salt or ester thereof, so as to thereby treat the subject.

The present invention also provides a compound of the present invention or a salt or ester thereof, for use as an add-on therapy or in combination with an NMDA receptor antagonist, in treating a subject afflicted with pain.

The present invention further provides a pharmaceutical composition comprising an amount of any of the compounds of the present invention, or a salt or ester thereof, and an amount of an NMDA receptor antagonist, for use in treating a subject afflicted with pain.

The present invention also provides a method of treating a subject afflicted with pain comprising administering to the subject an effective amount of an NMDA receptor partial agonist, and an effective amount of any compound of the present invention, or a salt or ester thereof, so as to thereby treat the subject.

The present invention also provides a compound of the present invention or a salt or ester thereof, for use as an add-on therapy or in combination with an NMDA receptor partial agonist in treating a subject afflicted with pain.

The present invention further provides a pharmaceutical composition comprising an amount of any of the compounds of the present invention, or a salt or ester thereof, and an amount of an NMDA receptor partial agonist, for use in treating a subject afflicted with pain.

The present invention also provides a method of treating a subject afflicted with pain comprising administering to the subject an effective amount of a neurokinin 1 receptor antagonist and an effective amount of any compound of the present invention, or a salt or ester thereof, so as to thereby treat the subject.

The present invention also provides a compound of the present invention or a salt or ester thereof, for use as an add-on therapy or in combination with a neurokinin 1 receptor antagonist in treating a subject afflicted with pain.

The present invention further provides a pharmaceutical composition comprising an amount of any of the compounds of the present invention, or a salt or ester thereof, and an amount of a neurokinin 1 receptor antagonist for use in treating a subject afflicted with pain.

In some embodiments, a method of treating a subject afflicted with opioid overdose, opioid addiction or opioid withdrawal symptoms comprising administering to the subject an effective amount of naloxone or methylnaltrexone and an effective amount of the compound of the present invention so as to thereby treat the subject afflicted with the opioid overdose, opioid addiction or opioid withdrawal symptoms.

In some embodiments, a method of treating a subject afflicted with pain, a depressive disorder, a mood disorder, borderline personality disorder or opioid-induced respiratory depression, comprising administering to the subject an effective amount of naloxone or methylnaltrexone and an effective amount of the compound of the present invention so as to thereby treat the subject afflicted with pain, the depressive disorder, mood disorder, borderline personality disorder or opioid-induced respiratory depression.

The present invention also provides a method of treating a subject afflicted with pain comprising administering to the subject an effective amount of a DOR agonist and an effective amount of any compound of the present invention, or a salt or ester thereof, so as to thereby treat the subject.

The present invention also provides a compound of the present invention or a salt or ester thereof, for use as an add-on therapy or in combination with a DOR agonist in treating a subject afflicted with pain.

The present invention further provides a pharmaceutical composition comprising an amount of any of the compounds of the present invention, or a salt or ester thereof, and an amount of a DOR agonist for use in treating a subject afflicted with pain.

In any of the embodiments of the present method, compound, package, use or pharmaceutical composition the subject is afflicted with borderline personality disorder, opioid addiction, opioid withdrawal symptoms, opioid-induced respiratory depression or opioid overdose symptoms.

In some embodiments of the present method, compound, package, use or pharmaceutical composition, the compound has the structure:

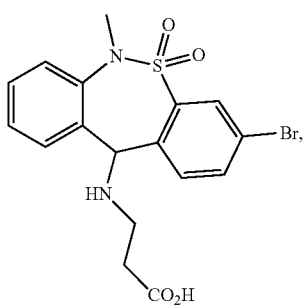

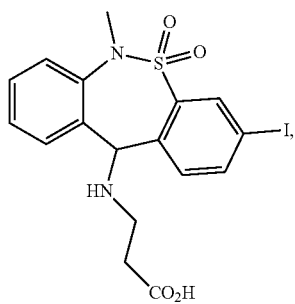

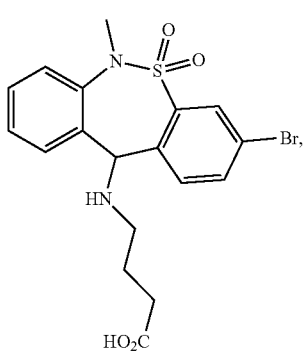

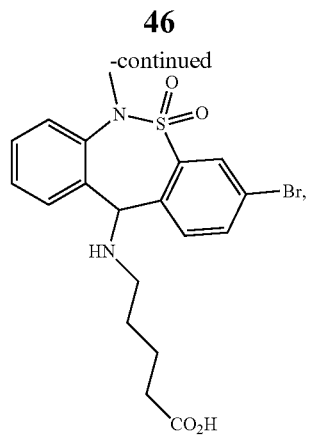

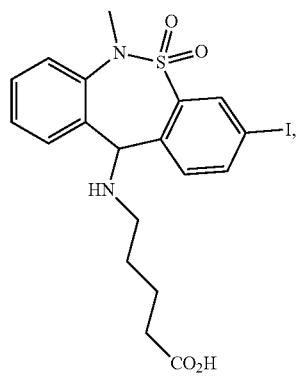

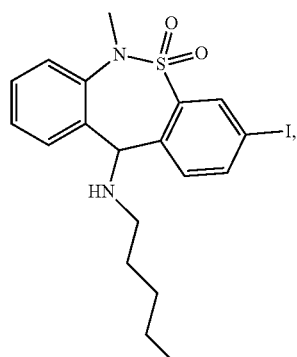

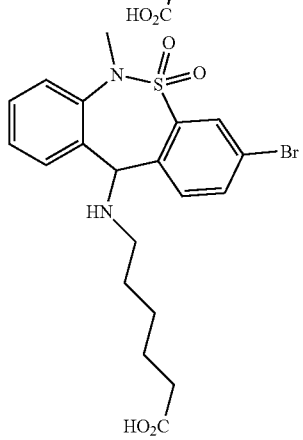

47
-continued
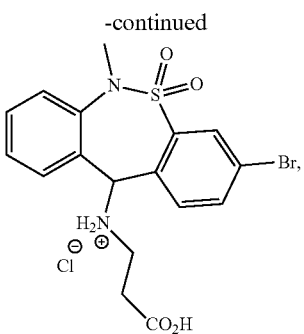
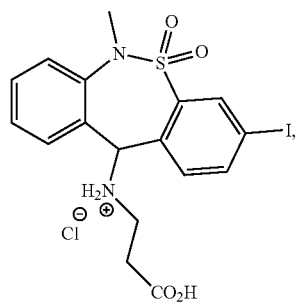
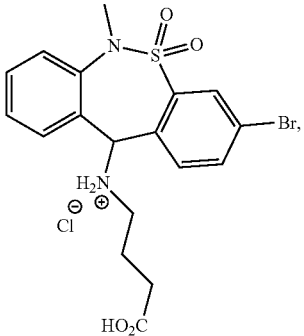
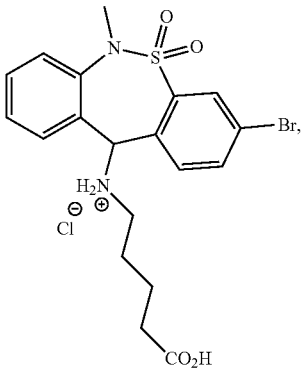
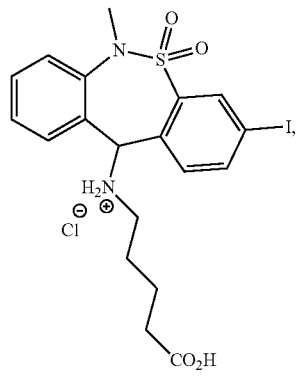
48
-continued
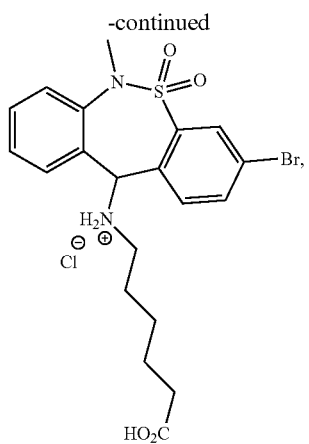
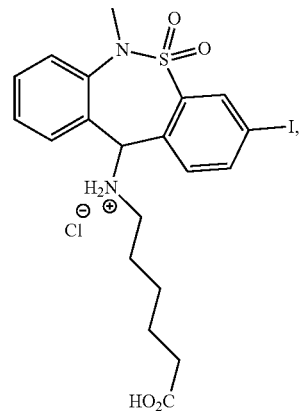
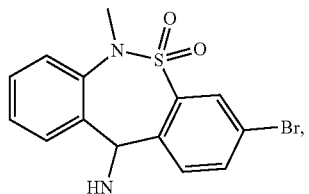
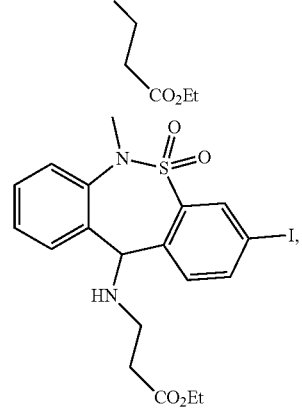

-continued

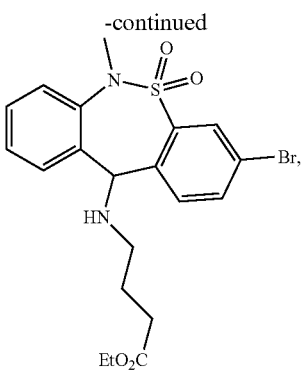

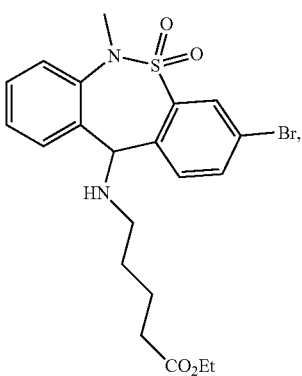

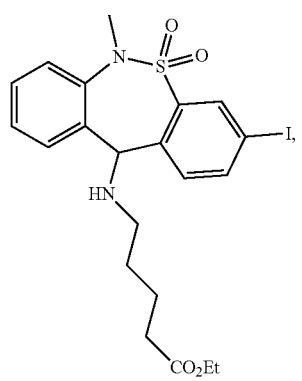

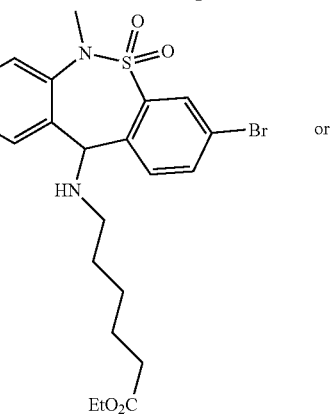

-continued

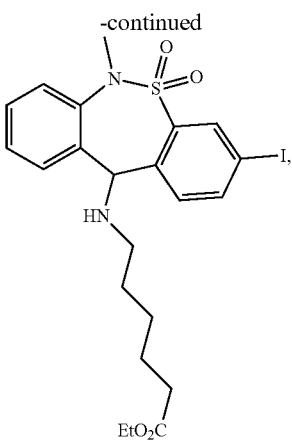

or a pharmaceutically acceptable salt or ester thereof.

In some embodiments of any of the above method, compound, package, use or pharmaceutical composition, the compound has the structure:

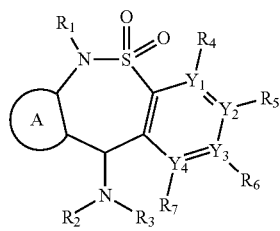

wherein
A is an aryl or heteroaryl, with or without substitution;
$R_1$ is —H or -(alkyl);
$R_2$ is -(alkyl), -(alkenyl), -(alkynyl)-(alkyl)-OH, -(alkyl)-$CO_2$H, -(alkyl)-$CO_2$-(alkyl), -(alkyl)-C(O)—$NH_2$, -(alkyl)-C(O)—NH(alkyl), -(alkyl)-C(O)—NH-(hydroxyalkyl), -(alkyl)-C(O)—N(alkyl)$_2$, -(alkyl)-C(O)—N(hydroxyalkyl)$_2$, -(alkyl)-O-(alkyl), -(alkyl)-S-(alkyl), -(alkyl)-$CF_3$, -(alkyl)-O-(hydroxyalkyl), -(alkyl)-O-(alkyl)-$OCH_3$, -(alkyl)-(CH)—(O-(alkyl))$_2$, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);
$R_3$ is —H or -(alkyl);
$R_4$, $R_5$, $R_6$ and $R_7$ are each absent or present, and when present, are each independently —H, —Cl, —Br, —F, —I, —CN, —$CF_3$, —$OCF_3$, -(alkyl), -(alkenyl), -(alkynyl), -(aryl), —$NH_2$, —NH-(alkyl), —NH-(alkenyl), —NH-(alkynyl)-NH-(aryl), —NH-(heteroaryl), —OH, —OAc, —O—C(O) (alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), or —$SO_2$-(heteroaryl); and
$Y_1$, $Y_2$, $Y_3$ and $Y_4$ are each independently N or C,
wherein when $Y_1$ is N, then $R_4$ is absent, and when $Y_1$ is C, then $R_4$ is present; when $Y_2$ is N, then $R_5$ is absent, and when $Y_2$ is C, then $R_5$ is present; when $Y_3$ is N, then $R_6$ is absent, and when $Y_3$ is C, then $R_6$ is present; when $Y_4$ is N, then $R_7$ is absent, and when $Y_4$ is C, then $R_7$ is present, wherein when A is phenyl, R₁ is —CH₃, R₃, R₄, R₆, and R₇ are each —H, and R₅ is Cl, then R₂ is other than —(CH₂)₄CO₂H, —(CH₂)₆CO₂H, —(CH₂)₆CO₂CH₂CH₃, or —(CH₂)₆CH₃, wherein when A is phenyl, R₁ is —CH₃, R₃, R₄, R₆, and R₇ are each —H, and R₅ is —SO₂CH₃, then R₂ is other than —(CH₂)₃OCH₃, or a pharmaceutically acceptable salt thereof.

In some embodiments of any of the above method, compound, package, use or pharmaceutical composition, the compound has the structure:

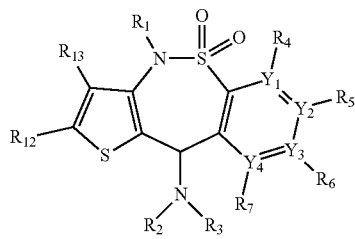

wherein

R₁ is —H or -(alkyl);

R₂ is -(alkyl), -(alkenyl), -(alkynyl), -(alkyl)-OH, -(alkyl)-CO₂H, -(alkyl)-CO₂-(alkyl), -(alkyl)-C(O)—NH₂, -(alkyl)-C(O)—NH(alkyl), -(alkyl)-C(O)—NH-(hydroxyalkyl), -(alkyl)-C(O)—N(alkyl)₂, -(alkyl)-C(O)—N(hydroxyalkyl)₂, -(alkyl)-O-(alkyl), -(alkyl)-S-(alkyl), -(alkyl)-CF₃, -(alkyl)-O-(hydroxyalkyl), -(alkyl)-O-(alkyl)-OCH₃, -(alkyl)-(CH)—(O-(alkyl))₂, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);

R₃ is —H or -(alkyl);

R₄, R₅, R₆ and R₇ are each absent or present, and when present, are each independently —H, —Cl, —Br, —F, —I, —CN, —CF₃, —OCF₃, -(alkyl), -(alkenyl), -(alkynyl), -(aryl), —NH₂, —NH-(alkyl), —NH-(alkenyl), —NH-(alkynyl)-NH-(aryl), —NH-(heteroaryl), —OH, —OAc, —O—C(O) (alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO₂-(alkyl), —SO₂-(aryl), or —SO₂-(heteroaryl);

R₁₂ and R₁₃ are each independently —H, —Cl, —Br, —F, —I, —CN, —CF₃, —OCF₃, -(alkyl), -(aryl), -(heteroaryl)-(alkenyl), -(alkynyl), —NH₂, —NH-(alkyl), —NH-(alkenyl), —NH-(alkynyl)-NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO₂-(alkyl), —SO₂-(aryl), or —SO₂-(heteroaryl); and Y₁, Y₂, Y₃ and Y₄ are each independently N or C,
wherein when Y₁ is N, then R₄ is absent, and when Y₁ is C, then R₄ is present; when Y₂ is N, then R₅ is absent, and when Y₂ is C, then R₅ is present; when Y₃ is N, then R₆ is absent, and when Y₃ is C, then R₆ is present; when Y₄ is N, then R₇ is absent, and when Y₄ is C, then R₇ is present.

In some embodiments of any of the above method, compound, package, use or pharmaceutical composition, the compound has the structure:

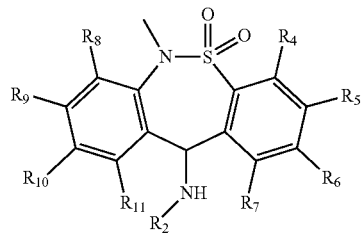

wherein

R₂ is -(alkyl), -(alkenyl), -(alkynyl), -(alkyl)-OH, -(alkyl)-CO₂H, -(alkyl)-CO₂-(alkyl), -(alkyl)-C(O)—NH₂, -(alkyl)-C(O)—NH(alkyl), -(alkyl)-C(O)—NH-(hydroxyalkyl), -(alkyl)-C(O)—N(alkyl)₂, -(alkyl)-C(O)—N(hydroxyalkyl)₂, -(alkyl)-O-(alkyl), -(alkyl)-S-(alkyl), -(alkyl)-CF₃, -(alkyl)-O-(hydroxyalkyl), -(alkyl)-O-(alkyl)-O-(alkyl), -(alkyl)-(CH)—(O-(alkyl))₂, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);

R₅ is —Br, or —I;

R₄, R₆ and R₇ are each independently —H, —Cl, —Br, —F, —I, —CN, —CF₃, —OCF₃, -(alkyl), -(alkenyl), -(alkynyl), -(aryl), —NH₂, —NH-(alkyl), —NH-(alkenyl), —NH-(alkynyl)-NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO₂-(alkyl), —SO₂-(aryl) or —SO₂-(heteroaryl); and R₈, R₉, R₁₀ and R₁₁ are each independently —H, —Cl, —Br, —F, —I, —CN, —CF₃, —OCF₃, -(alkyl), -(aryl), -(heteroaryl)-(alkenyl), -(alkynyl), —NH₂, —NH-(alkyl), —NH-(alkenyl), —NH-(alkynyl)-NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO₂-(alkyl), —SO₂-(aryl), or —SO₂-(heteroaryl).

In some embodiments of any of the above method, compound, package, use or pharmaceutical composition, the compound has the structure:

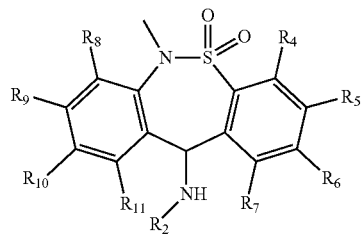

wherein

R₂ is -(alkyl)-O-(alkyl) or -(alkyl)-O-(alkyl)-O-(alkyl);

R₅ is —Cl, —Br, —F, or —I;

R4, R6 and R7 are each independently —H, —Cl, —Br, —F, —I, —CN, —CF3, —OCF3, -(alkyl), -(alkenyl), -(alkynyl), -(aryl), —NH2, —NH-(alkyl), —NH-(alkenyl), —NH-(alkynyl)-NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO2-(alkyl), —SO2-(aryl) or —SO2-(heteroaryl);

R8, R9, R10 and R11 are each independently —H, —Cl, —Br, —F, —I, —CN, —CF3, —OCF3, -(alkyl), -(aryl), -(heteroaryl)-(alkenyl), -(alkynyl), —NH2, —NH-(alkyl), —NH-(alkenyl), —NH-(alkynyl)-NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO2-(alkyl), —SO2-(aryl), or —SO2-(heteroaryl).

In some embodiments of any of the above method, compound, package, use or pharmaceutical composition, the compound has the structure:

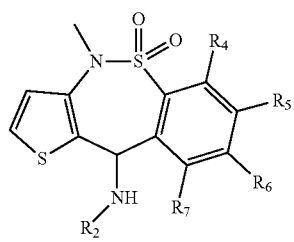

wherein

R2 is -(alkyl), -(alkenyl), -(alkynyl), -(alkyl)-OH, -(alkyl)-CO2H, -(alkyl)-CO2-(alkyl), -(alkyl)-C(O)—NH2, -(alkyl)-C(O)—NH(alkyl), -(alkyl)-C(O)—NH-(hydroxyalkyl), -(alkyl)-C(O)—N(alkyl)2, -(alkyl)-C(O)—N(hydroxyalkyl)2, -(alkyl)-O-(alkyl), -(alkyl)-S-(alkyl), -(alkyl)-CF3, -(alkyl)-O-(hydroxyalkyl), -(alkyl)-O-(alkyl)-(alkyl), -(alkyl)-(CH)—(O-(alkyl))2, -(alkyl)-(heterocyclyl), -(alkyl)-OAc, -(alkyl)-tetrahydrofuran, -(alkyl)-pyrrolidine, -(alkyl)-N-methylpyrrolidine, -(alkyl)-(1,3-dioxane) or -(alkyl)-(4,5-dihydrooxazole);

R5 is —Cl, —Br, —F, or —I;

R4, R6 and R7 are each independently —H, —Cl, —Br, —F, —I, —CN, —CF3, —OCF3, -(alkyl), -(alkenyl), -(alkynyl), -(aryl), —NH2, —NH-(alkyl), —NH-(alkenyl), —NH-(alkynyl)-NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO2-(alkyl), —SO2-(aryl) or —SO2-(heteroaryl).

In some embodiments of any of the above method, compound, package, use or pharmaceutical composition, the compound has the structure:

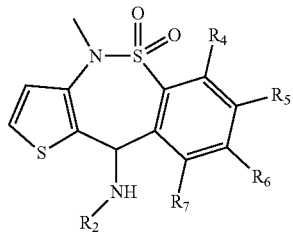

wherein

R2 is -(alkyl)-CO2-(alkyl), -(alkyl)-O-(alkyl) or -(alkyl)-O-(alkyl)-O-(alkyl);

R5 is —Cl, —Br, —F, or —I;

R4, R6 and R7 are each independently —H, —Cl, —Br, —F, —I, —CN, —CF3, —OCF3, -(alkyl), -(alkenyl), -(alkynyl), -(aryl), —NH2, —NH-(alkyl), —NH-(alkenyl), —NH-(alkynyl)-NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO2-(alkyl), —SO2-(aryl) or —SO2-(heteroaryl);

R8, R9, R10 and R11 are each independently —H, —Cl, —Br, —F, —I, —CN, —CF3, —OCF3, -(alkyl), -(aryl), -(heteroaryl)-(alkenyl), -(alkynyl), —NH2, —NH-(alkyl), —NH-(alkenyl), —NH-(alkynyl)-NH-(aryl), —NH-(heteroaryl), —OH, —OAc, —O—C(O)(alkyl), —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO2-(alkyl), —SO2-(aryl), or —SO2-(heteroaryl).

In some embodiments of any of the above method, compound, package, use or pharmaceutical composition, the compound has the structure:

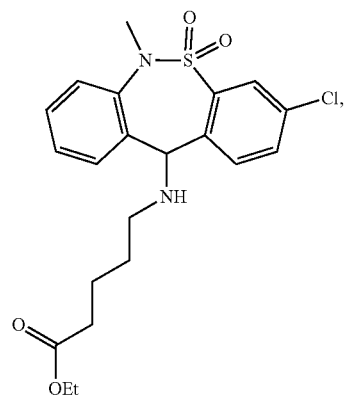

55
-continued
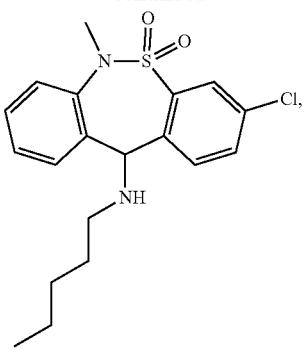
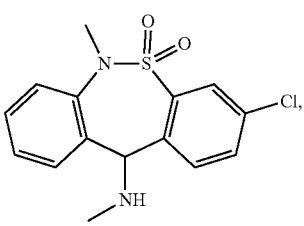
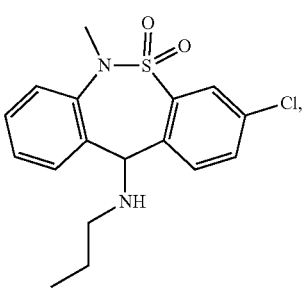
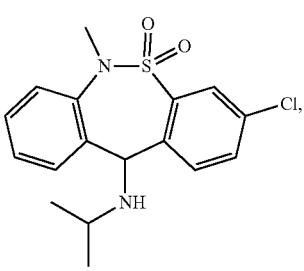
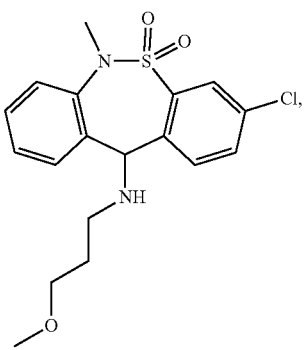
56
-continued
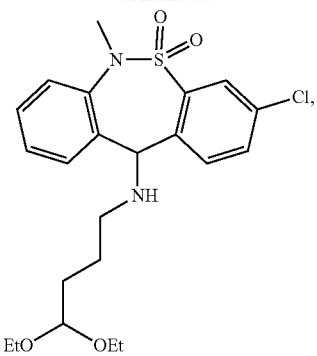
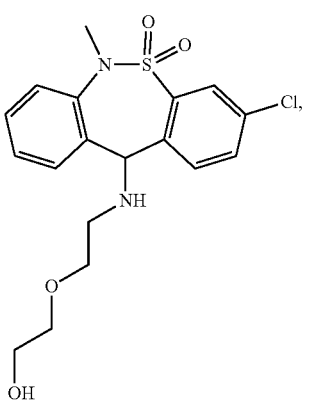
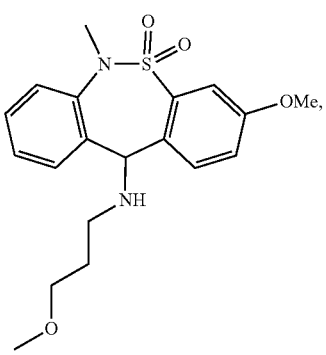
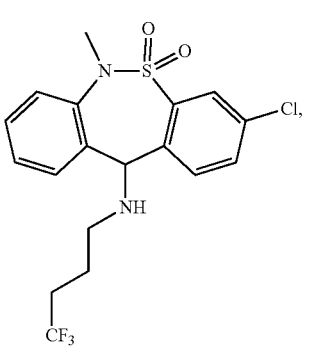

57
-continued
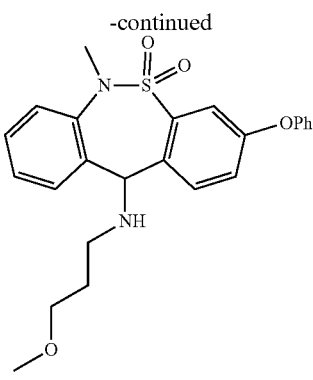
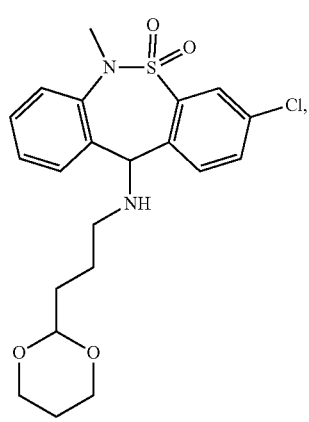
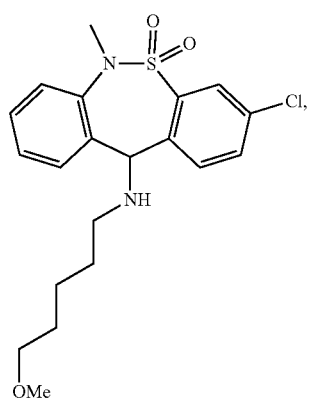
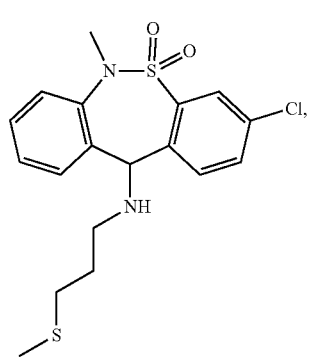
58
-continued
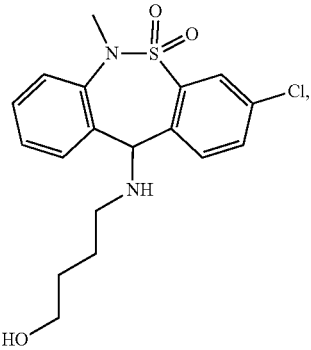
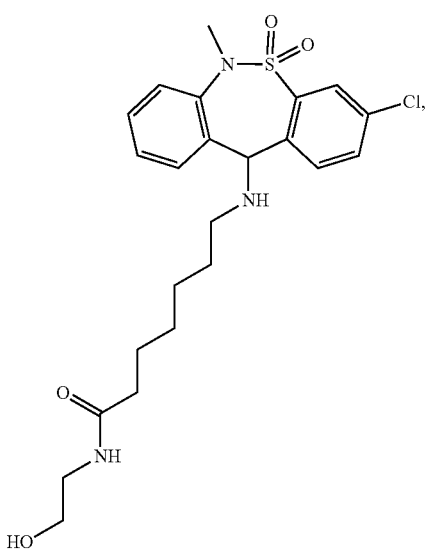
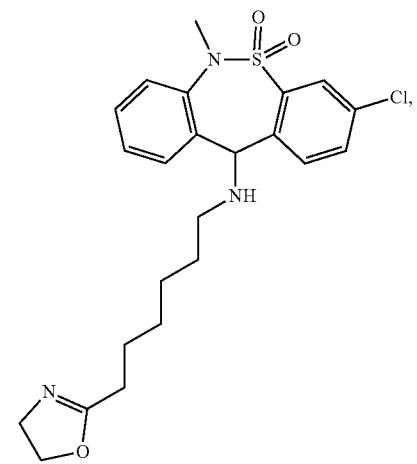

-continued
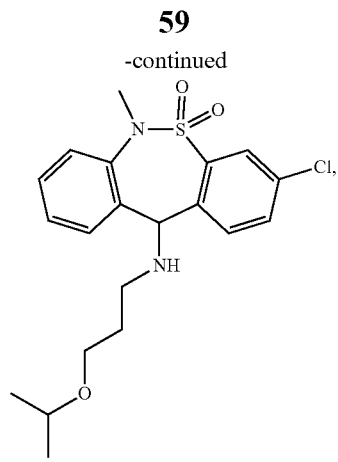
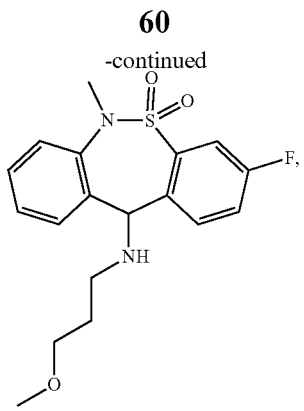
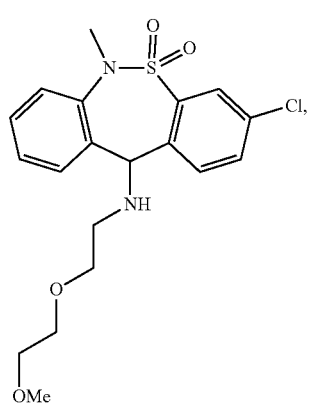
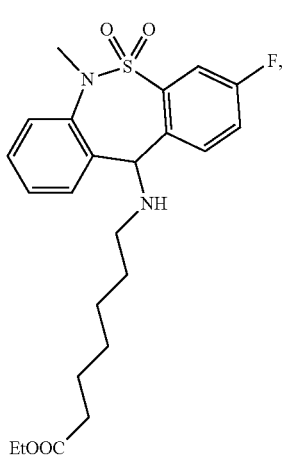
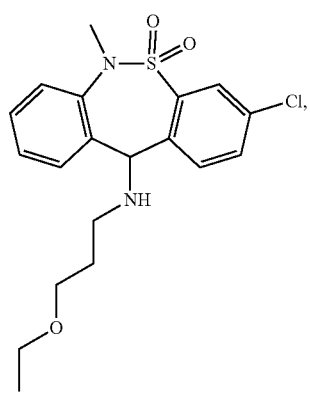
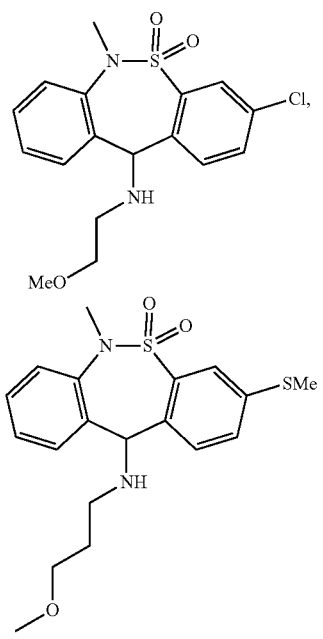
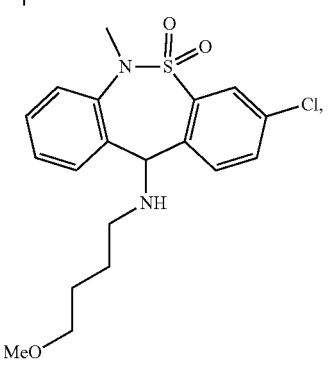

61
-continued
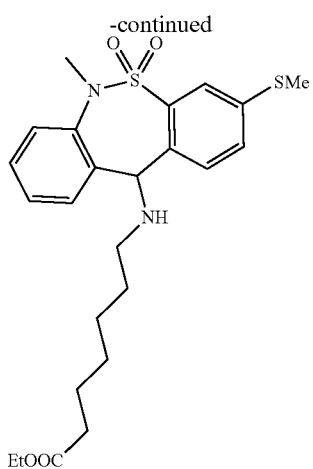
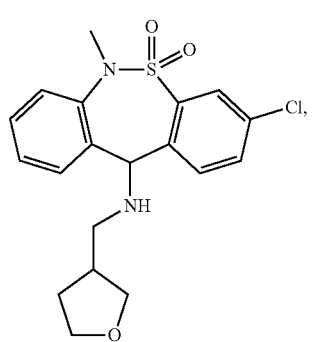
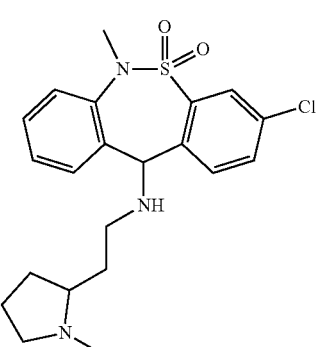
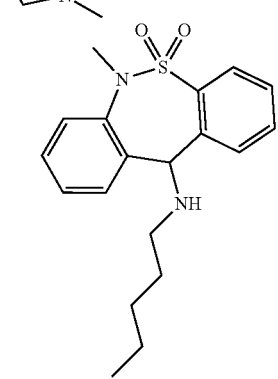
62
-continued
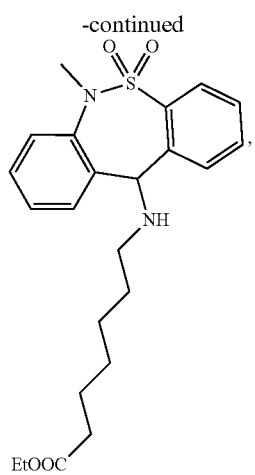
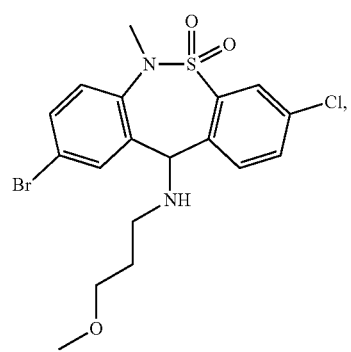
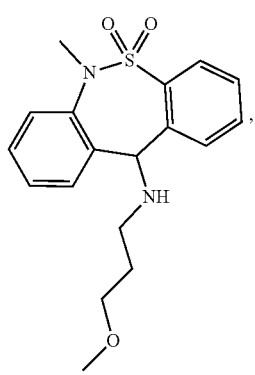
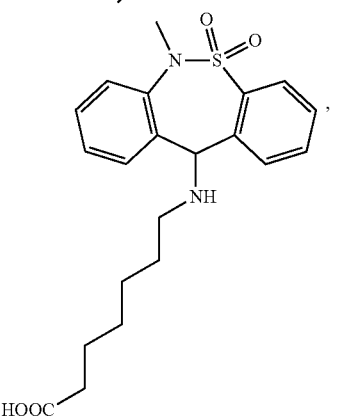

63
-continued
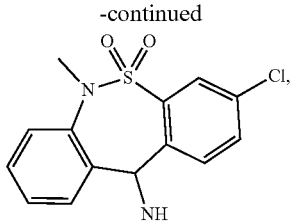
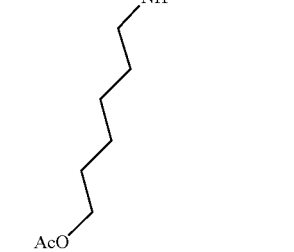
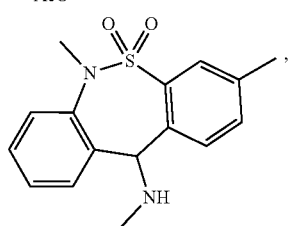
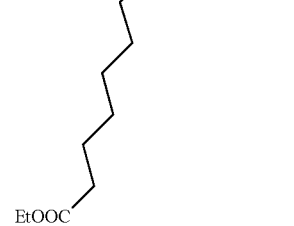
64
-continued
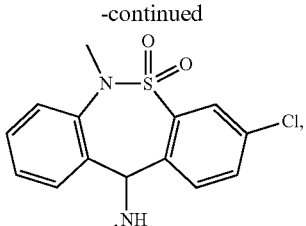
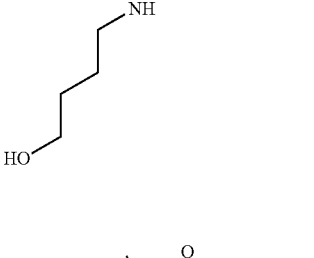
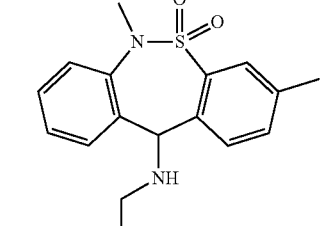
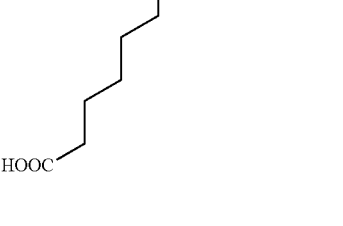
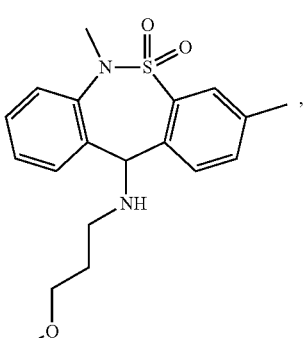
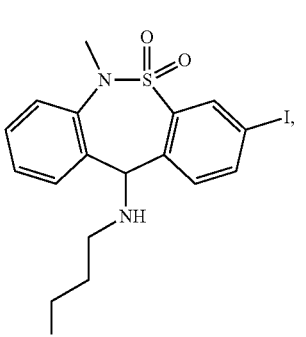
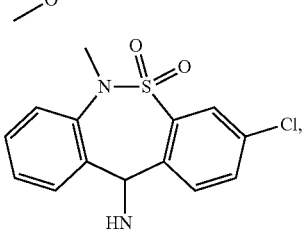
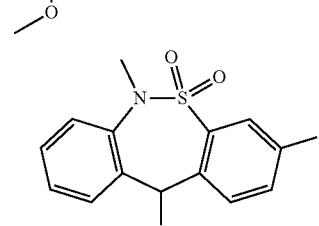
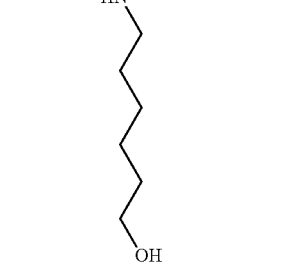

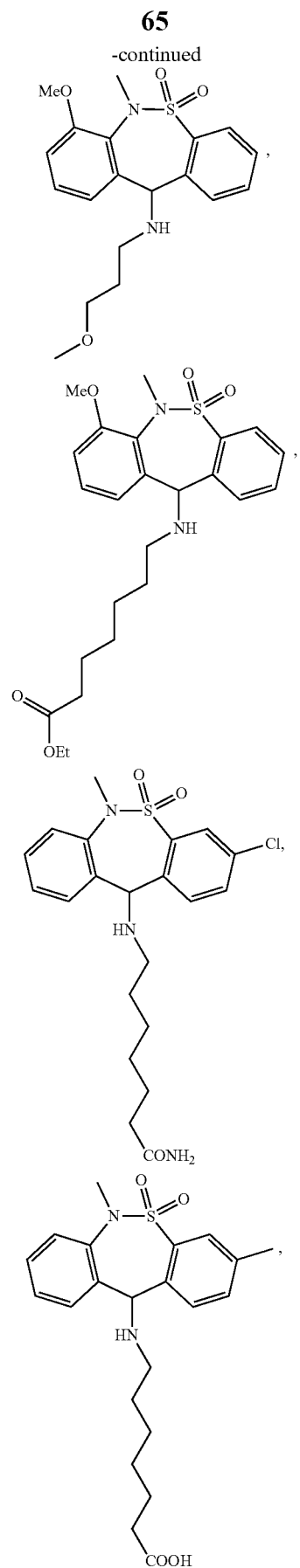
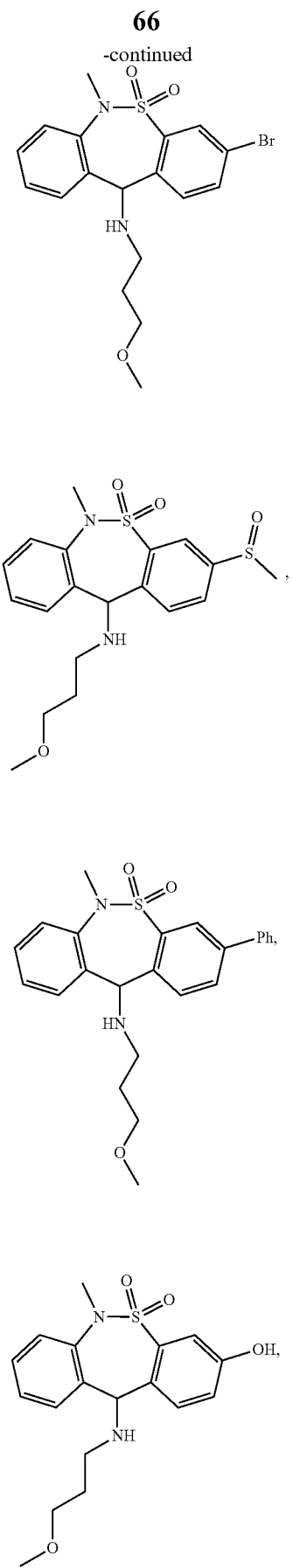

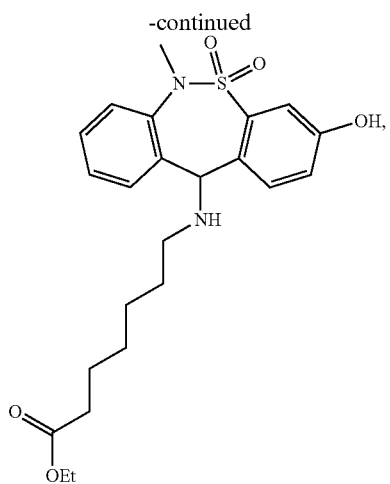
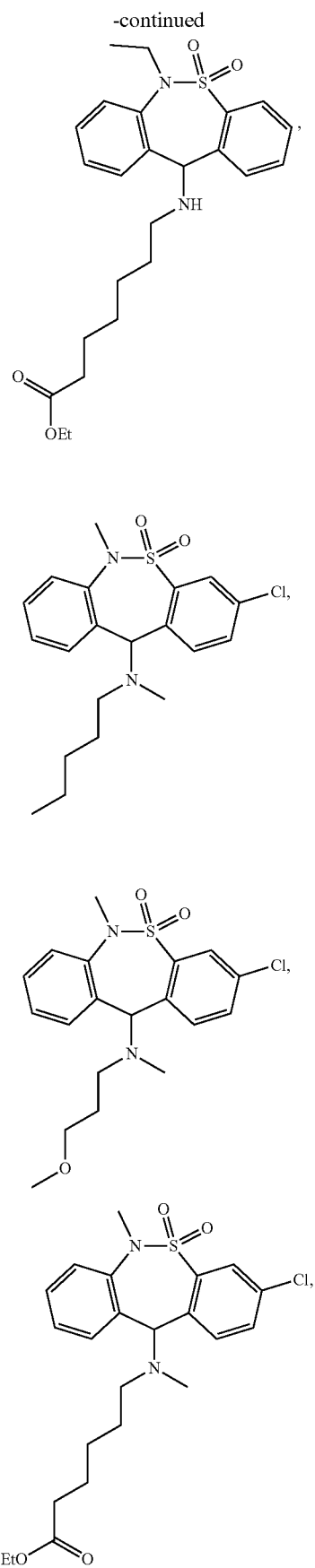

69
-continued
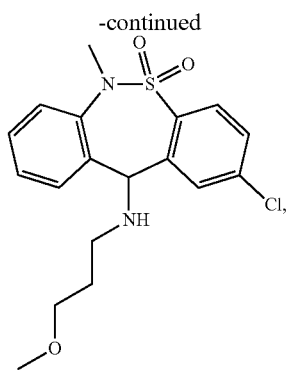
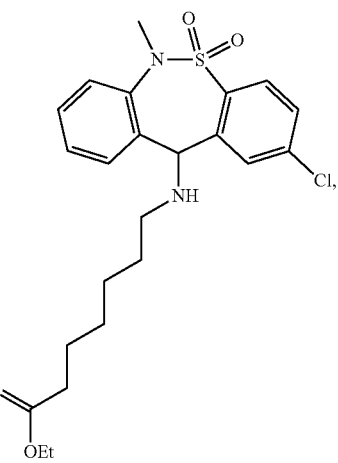
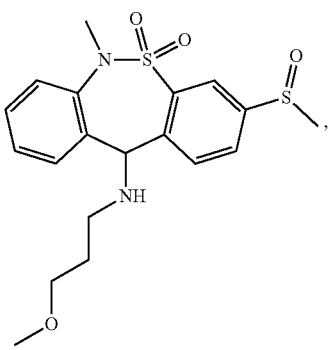
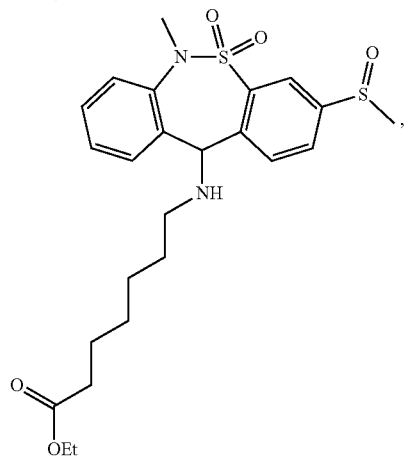
70
-continued
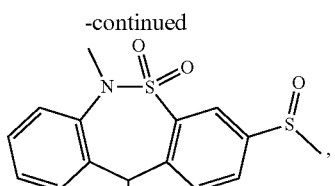
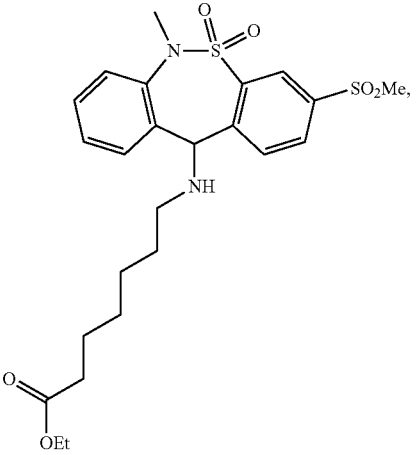
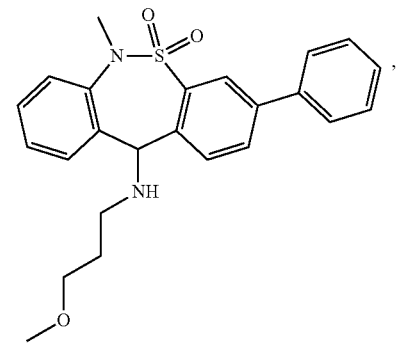
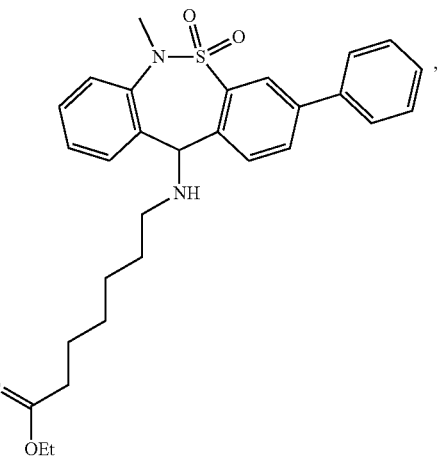

-continued
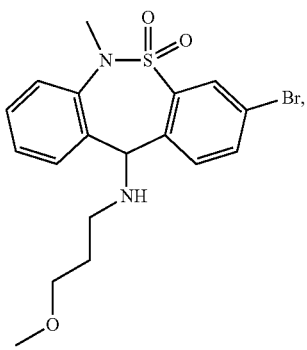
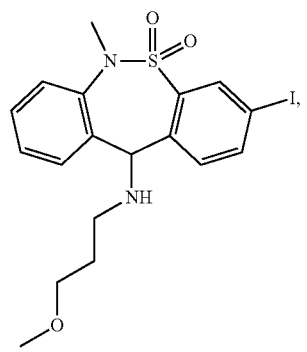
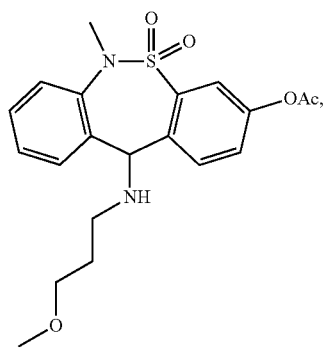
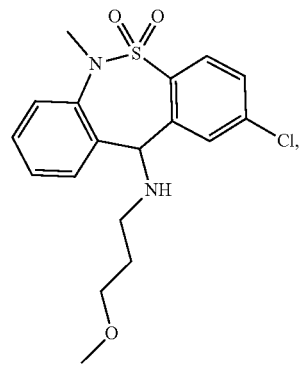
-continued
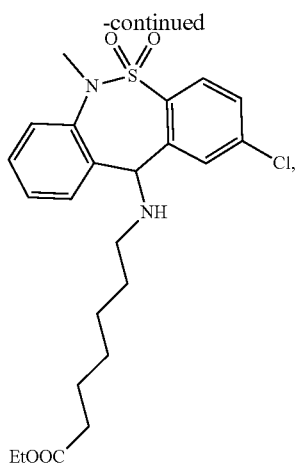
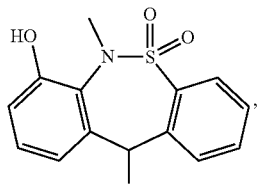
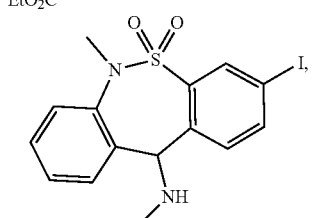
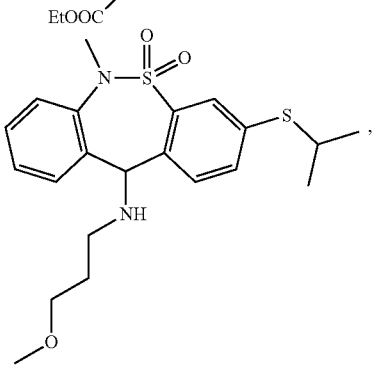

-continued
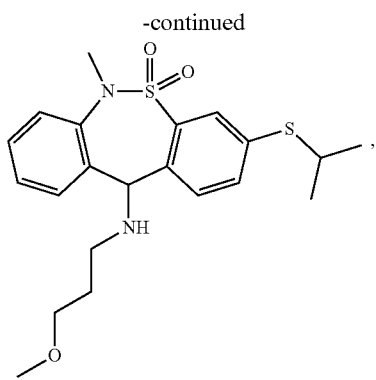
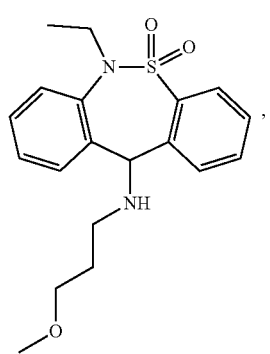
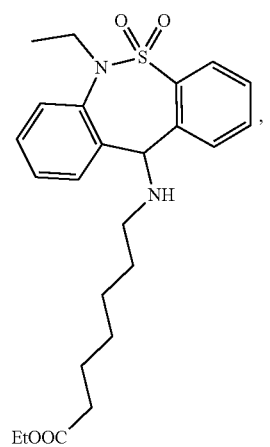
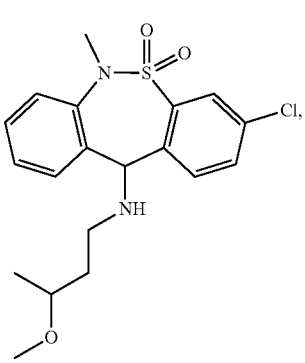
-continued
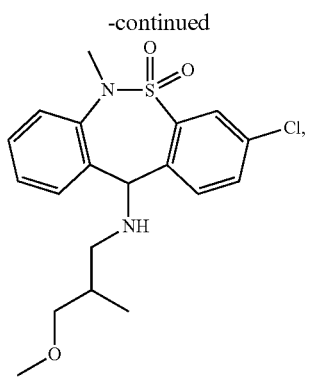
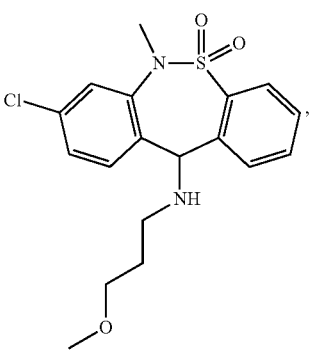
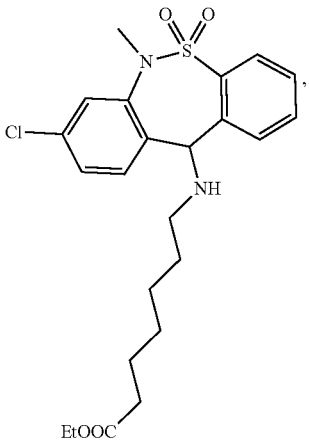
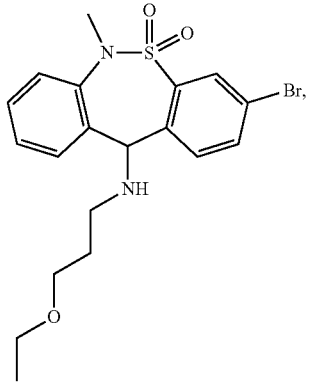

-continued
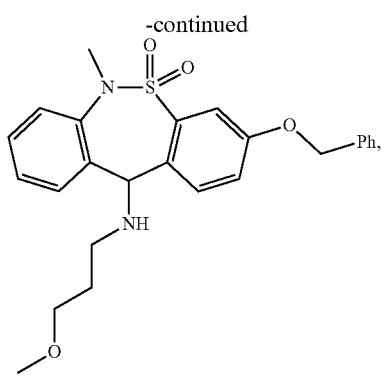
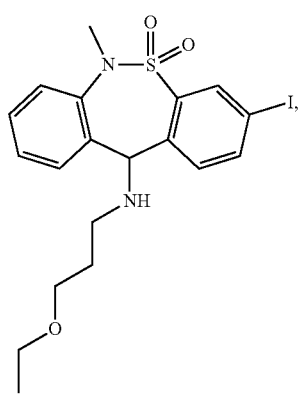
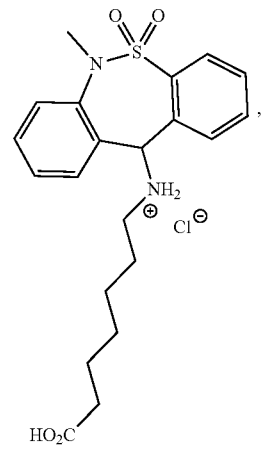
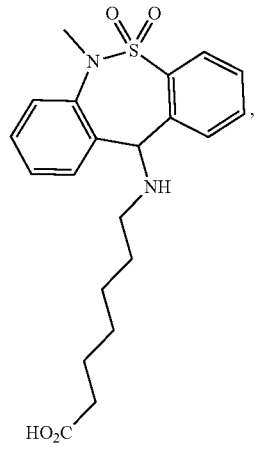
-continued
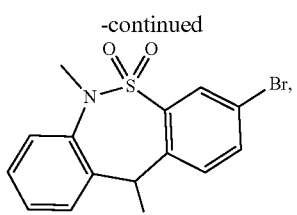
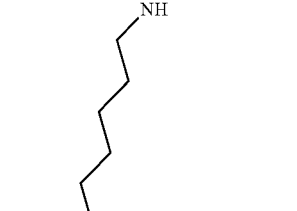
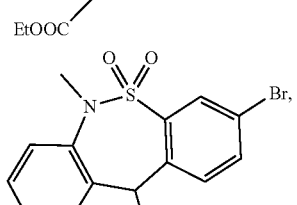
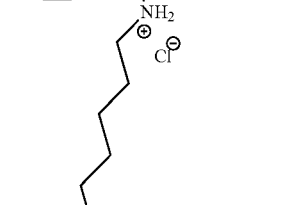
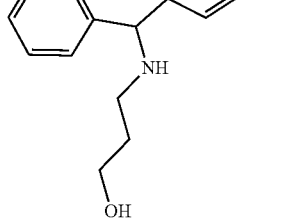

77
-continued
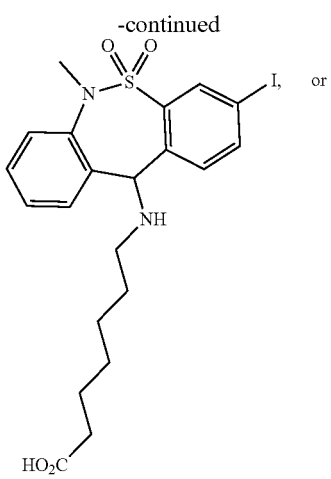
, or
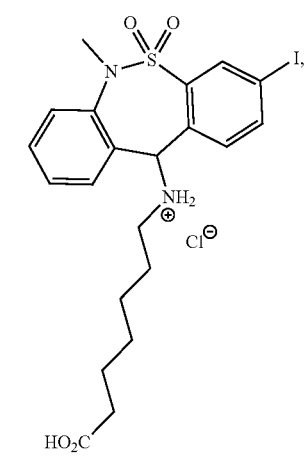
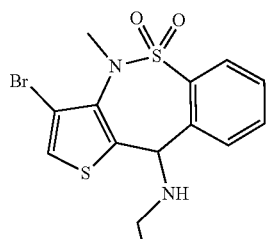
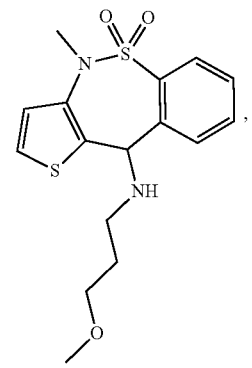
78
-continued
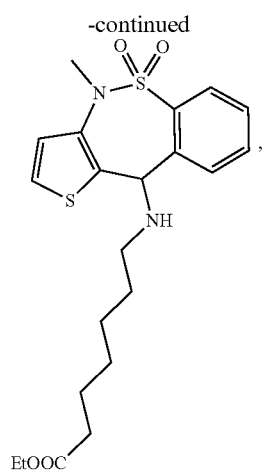
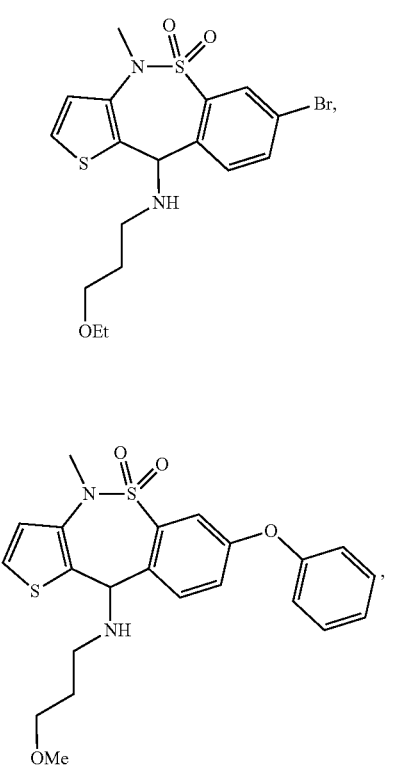

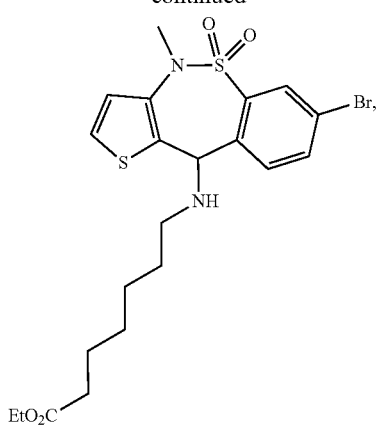

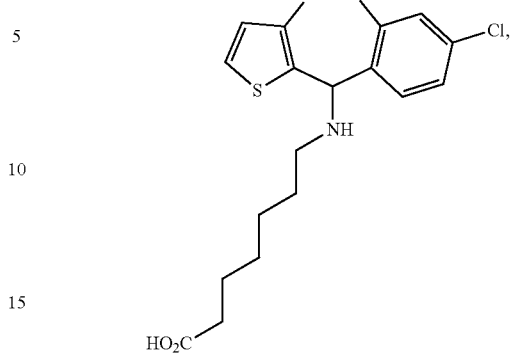

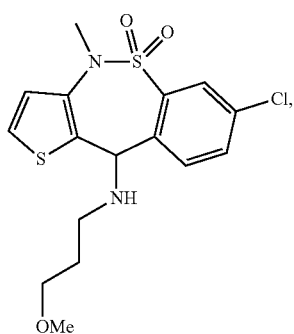

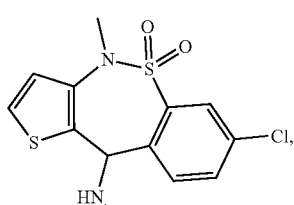

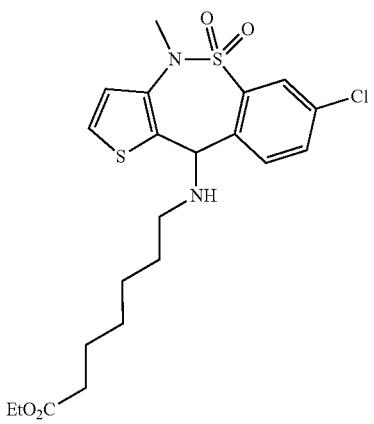

or a pharmaceutically acceptable salt thereof.

In some embodiments, a pharmaceutically acceptable salt of any of the above compounds of the present invention.

In some embodiments, a salt of the compound of the present invention is used in any of the above methods, uses, packages or compositions.

In some embodiments, a pharmaceutically salt of the compound of the present invention is used in any of the above methods, uses, packages or compositions.

In some embodiments, an ester of the compound of the present invention is used in any of the above methods, uses, packages or compositions.

Any of the above compounds may be used in any of the disclosed methods, uses, packages or pharmaceutical compositions.

Any of the compounds used in the disclosed methods, uses, packages or pharmaceutical compositions may be replaced with any other compound disclosed in the present invention.

Any of the above generic compounds may be used in any of the disclosed methods, uses, packages or compositions.

In some embodiments, the methods, uses, packages or pharmaceutical compositions of the present invention wherein the depressive disorder includes, but is not limited to, depression, major depression, dysthymia, postpartum depression, seasonal affective disorder, atypical depression, psychotic depression, bipolar disorder, premenstrual dysphoric disorder, situational depression or adjustment disorder with depressed mood.

In some embodiments, the methods, uses, packages or pharmaceutical compositions of the present invention wherein the depressive disorder is cyclothymia.

In some embodiments, the methods, uses, packages or pharmaceutical compositions of the present invention wherein the mood disorder includes, but is not limited to, anxiety, post-traumatic stress disorder (PTSD), acute stress disorder, generalized anxiety disorder (GAD), obsessive-compulsive disorder (OCD), panic disorder, social phobia or social anxiety disorder.

In some embodiments, the methods, uses, packages or pharmaceutical compositions of the present invention wherein the mood disorder is borderline personality disorder.

In some embodiments, the methods, uses, packages or pharmaceutical compositions of the present invention wherein the pain includes, but is not limited to, chronic pain or acute pain.

In some embodiments, the methods, uses, packages or pharmaceutical compositions wherein the opioid addiction includes, but is not limited to, addiction to codeine, hydrocodone, morphine, oxycodone, hydromorphone, oxymorphone, fentanyl or heroin.

In some embodiments, the methods, uses, packages or pharmaceutical compositions wherein the opioid withdrawal symptoms include, but are not limited to, agitation, anxiety, muscle aches, increased tearing, insomnia, runny nose, sweating, yawning, abdominal cramping, diarrhea, dilated pupils, goose bumps, nausea or vomiting.

In some embodiments, the NMDA receptor antagonist is an arylcyclohexylamine, dextromorphinan or adamantane.

In some embodiments, the NMDA receptor antagonist is dextromethorphan, dextrorphan, dextrallorphan, memantine, amantadine, rimantadine, nitromemantine (YQW-36), ketamine (and its analogs, e.g. tiletamine), phencyclidine (and its analogs, e.g. tenocyclidine, eticyclidine, rolicyclidine), methoxetamine (and its analogs), gacyclidine (GK-11), neramexane, lanicemine (AZD6765), diphenidine, dizocilpine (MK-801), 8a-phenyldecahydroquinoline (8A-PDHQ), remacemide, ifenprodil, traxoprodil (CP-101,606), eliprodil (SL-82.0715), etoxadrol (CL-1848C), dexoxadrol, WMS-2539, NEFA, delucemine (NPS-1506), aptiganel (Cerestat; CNS-1102), midafotel (CPPene; SDZ EAA 494), dexanabinol (HU-211 or ETS2101), selfotel (CGS-19755), 7-chlorokynurenic acid (7-CKA), 5,7-dichlorokynurenic acid (5,7-DCKA), L-683344, L-689560, L-701324, GV150526A, GV196771A, CERC-301 (formerly MK-0657), atomoxetine, LY-235959, CGP 61594, CGP 37849, CGP 40116 (active enantiomer of CG 37849), LY-233536, PEAQX (NVP-AAM077), ibogaine, noribogaine, Ro 25-6981, GW468816, EVT-101, indantadol, perzinfotel (EAA-090), SSR240600, 2-MDP (U-23807A) or AP-7.

In some embodiments, the NMDA receptor partial agonist is a NRX-1074 or rapastinel (GLYX-13).

In some embodiments, the neurokinin 1 receptor antagonist is aprepitant, fosaprepitant, casopitant, maropitant, vestipitant, vofopitant, lanepitant, orvepitant, ezlopitant, netupitant, rolapitant, L-733060, L-703606, L-759274, L-822429, L-760735, L-741671, L-742694, L-732138, CP-122721, RPR-100893, CP-96345, CP-99994, TAK-637, T-2328, CJ-11974, RP 67580, NKP608, VPD-737, GR 205171, LY686017, AV608, SR140333B, SSR240600C, FK 888 or GR 82334.

In some embodiments, the neurokinin 2 receptor antagonist is saredutant, ibodutant, nepadutant, GR-159897 or MEN-10376.

In some embodiments, the neurokinin 3 receptor antagonist is osanetant, talnetant, SB-222200 or SB-218795.

In some embodiments, the DOR agonist is tianeptine, (+)BW373U86, SNC-80, SNC-121, SNC-162, DPI-287, DPI-3290, DPI-221, TAN-67, KN-127, AZD2327, JNJ-20788560, NIH11082, RWJ-394674, ADL5747, ADL5859, UFP-512, AR-M100390, SB-235863 or 7-spiroindanyloxymorphone.

In some embodiments, the DOR antagonist is naltrindole, naltriben, N-benzylnaltrindole, 7-benzylidenenaltrexone, SDM25N, or DPI-2505.

The term "MOR agonist" is intended to mean any compound or substance that activates the mu-opioid receptor (MOR). The agonist may be a partial, full or super agonist.

The term "DOR agonist" is intended to mean any compound or substance that activates the delta-opioid receptor (DOR). The agonist may be a partial, full or super agonist.

The term "DOR antagonist" is intended to mean any compound or substance that blocks or reverses activation of the delta-opioid receptor (DOR).

In some embodiments, the compound is prepared by the following process:

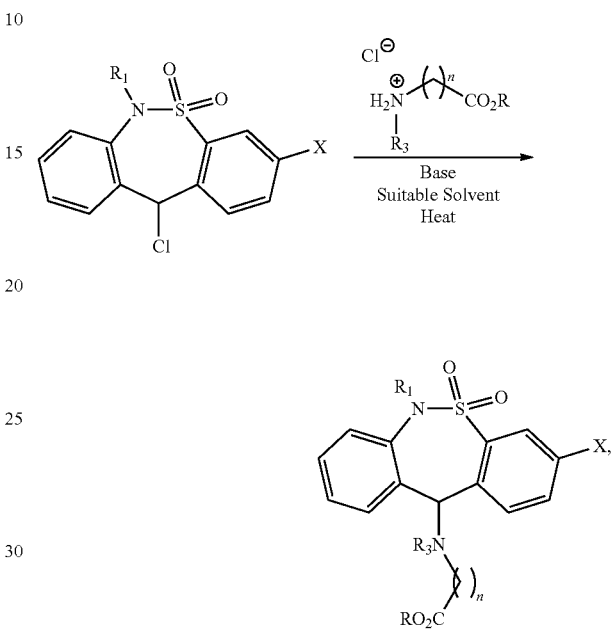

wherein R is -(alkyl); $R_1$ is —H or -(alkyl); $R_3$ is —H or -(alkyl); X=Br or I; and n=2-5.

In some embodiments, the compound is prepared by the following process:

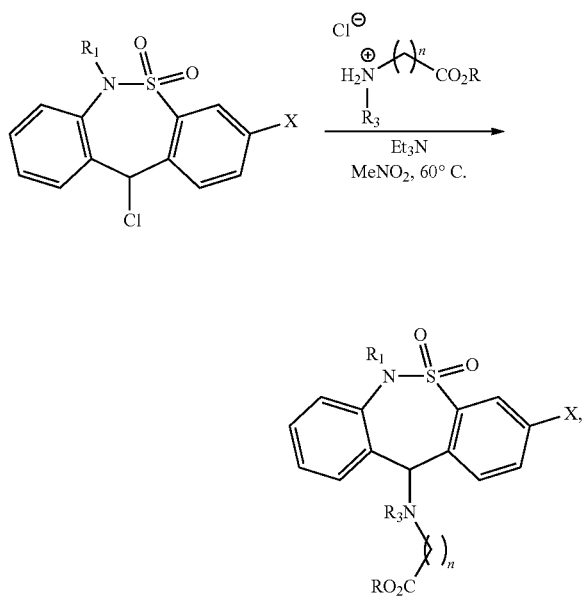

wherein R is -(alkyl); $R_1$ is —H or -(alkyl); $R_3$ is —H or -(alkyl); X=Br or I; and n=2-5.

In some embodiments, the compound is prepared by the following process:

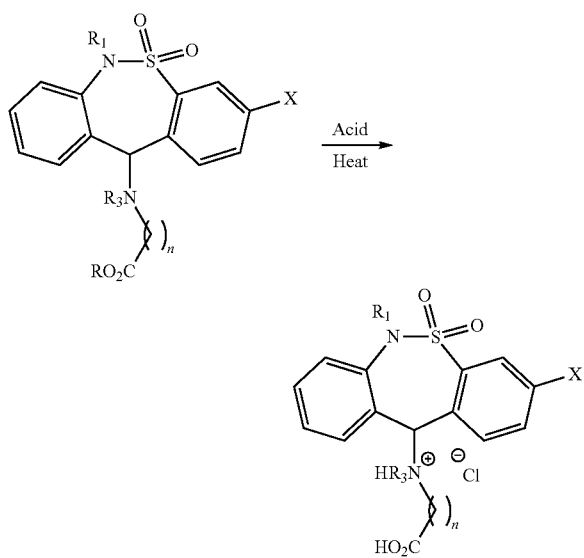

wherein R is -(alkyl); $R_1$ is —H or -(alkyl); $R_3$ is —H or -(alkyl); X=Br or I; and n=2-5.

In one embodiments of the above process, the acid is aqueous acid.

In some embodiments, the compound is prepared by the following process:

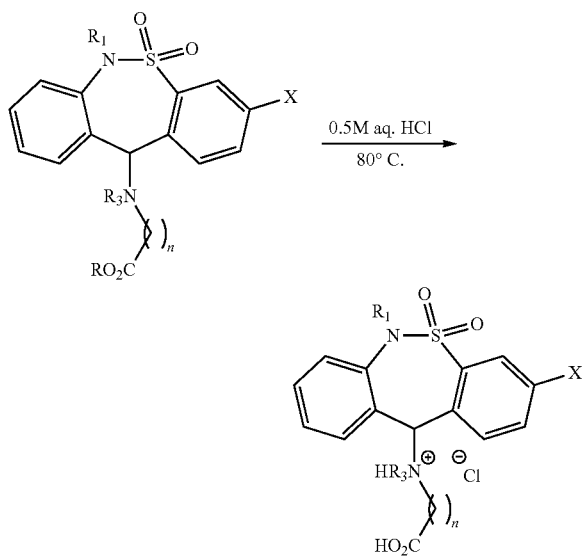

wherein R is -(alkyl); $R_1$ is —H or -(alkyl); $R_3$ is —H or -(alkyl); X=Br or I; and n=2-5.

Except where otherwise specified, the structure of a compound of this invention includes an asymmetric carbon atom, it is understood that the compound occurs as a racemate, racemic mixture, and isolated single enantiomer. All such isomeric forms of these compounds are expressly included in this invention. Except where otherwise specified, each stereogenic carbon may be of the R or S configuration.

It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis, such as those described in "Enantiomers, Racemates and Resolutions" by J. Jacques, A. Collet and S. Wilen, Pub. John Wiley & Sons, NY, 1981. For example, the resolution may be carried out by preparative chromatography on a chiral column.

The subject invention is also intended to include all isotopes of atoms occurring on the compounds disclosed herein. Isotopes include those atoms having the same atomic number but different mass numbers.

By way of general example and without limitation, isotopes of hydrogen include tritium and deuterium. Isotopes of carbon include C-13 and C-14.

It will be noted that any notation of a carbon in structures throughout this application, when used without further notation, are intended to represent all isotopes of carbon, such as $^{12}C$, $^{13}C$, or $^{14}C$. Furthermore, any compounds containing $^{13}C$ or $^{14}C$ may specifically have the structure of any of the compounds disclosed herein.

It will also be noted that any notation of a hydrogen in structures throughout this application, when used without further notation, are intended to represent all isotopes of hydrogen, such as 1H, $^2H$, or $^3H$.

Furthermore, any compounds containing $^2H$ or $^3H$ may specifically have the structure of any of the compounds disclosed herein.

Isotopically-labeled compounds can generally be prepared by conventional techniques known to those skilled in the art using appropriate isotopically-labeled reagents in place of the non-labeled reagents employed.

In the compounds used in the method of the present invention, the substituents may be substituted or unsubstituted, unless specifically defined otherwise.

In the compounds used in the method of the present invention, alkyl, heteroalkyl, monocycle, bicycle, aryl, heteroaryl and heterocycle groups can be further substituted by replacing one or more hydrogen atoms with alternative non-hydrogen groups. These include, but are not limited to, halo, hydroxy, mercapto, amino, carboxy, cyano and carbamoyl.

It is understood that substituents and substitution patterns on the compounds used in the method of the present invention can be selected by one of ordinary skill in the art to provide compounds that are chemically stable and that can be readily synthesized by techniques known in the art from readily available starting materials. If a substituent is itself substituted with more than one group, it is understood that these multiple groups may be on the same carbon or on different carbons, so long as a stable structure results.

In choosing the compounds used in the method of the present invention, one of ordinary skill in the art will recognize that the various substituents, i.e. $R_1$, $R_2$, etc. are to be chosen in conformity with well-known principles of chemical structure connectivity.

As used herein, "alkyl" is intended to include both branched and straight-chain saturated aliphatic hydrocarbon groups having the specified number of carbon atoms. Thus, $C_1$-$C_n$ as in "$C_1$-$C_n$ alkyl" is defined to include groups having 1, 2 . . . , n–1 or n carbons in a linear or branched arrangement, and specifically includes methyl, ethyl, propyl, butyl, pentyl, hexyl, heptyl, isopropyl, isobutyl, sec-butyl and so on. An embodiment can be $C_1$-$C_{12}$ alkyl, $C_2$-$C_{12}$ alkyl, $C_3$-$C_{12}$ alkyl, $C_4$-$C_{12}$ alkyl and so on. An embodiment can be $C_1$-$C_8$ alkyl, $C_2$-$C_8$ alkyl, $C_3$-$C_8$ alkyl, $C_4$-$C_8$ alkyl and so on. "Alkoxy" represents an alkyl group as described above attached through an oxygen bridge.

The term "alkenyl" refers to a non-aromatic hydrocarbon radical, straight or branched, containing at least 1 carbon to carbon double bond, and up to the maximum possible number of non-aromatic carbon-carbon double bonds may be present. Thus, $C_2$—C, alkenyl is defined to include groups having 1, 2 . . . , n–1 or n carbons. For example, "$C_2$-$C_6$ alkenyl" means an alkenyl radical having 2, 3, 4, 5, or 6 carbon atoms, and at least 1 carbon-carbon double bond, and up to, for example, 3 carbon-carbon double bonds in the case of a $C_6$ alkenyl, respectively. Alkenyl groups include ethenyl, propenyl, butenyl and cyclohexenyl. As described above with respect to alkyl, the straight, branched or cyclic portion of the alkenyl group may contain double bonds and may be substituted if a substituted alkenyl group is indicated. An embodiment can be $C_2$-$C_{12}$ alkenyl or $C_2$-$C_8$ alkenyl.

The term "alkynyl" refers to a hydrocarbon radical straight or branched, containing at least 1 carbon to carbon triple bond, and up to the maximum possible number of non-aromatic carbon-carbon triple bonds may be present. Thus, $C_2$-$C_n$ alkynyl is defined to include groups having 1, 2 . . . , n–1 or n carbons. For example, "$C_2$-$C_6$ alkynyl" means an alkynyl radical having 2 or 3 carbon atoms, and 1 carbon-carbon triple bond, or having 4 or 5 carbon atoms, and up to 2 carbon-carbon triple bonds, or having 6 carbon atoms, and up to 3 carbon-carbon triple bonds. Alkynyl groups include ethynyl, propynyl and butynyl. As described above with respect to alkyl, the straight or branched portion of the alkynyl group may contain triple bonds and may be substituted if a substituted alkynyl group is indicated. An embodiment can be a $C_2$-$C_n$ alkynyl. An embodiment can be $C_2$-$C_{12}$ alkynyl or $C_3$-$C_8$ alkynyl.

As used herein, "hydroxyalkyl" includes alkyl groups as described above wherein one or more bonds to hydrogen contained therein are replaced by a bond to an —OH group. In some embodiments, $C_1$-$C_{12}$ hydroxyalkyl or $C_1$-$C_6$ hydroxyalkyl. $C_1$-$C_n$ as in "$C_1$-$C_n$ alkyl" is defined to include groups having 1, 2, . . . , n–1 or n carbons in a linear or branched arrangement (e.g. $C_1$-$C_2$ hydroxyalkyl, $C_1$-$C_3$ hydroxyalkyl, $C_1$-$C_4$ hydroxyalkyl, $C_1$-$C_5$ hydroxyalkyl, or $C_1$-$C_6$ hydroxyalkyl) For example, $C_1$-$C_6$, as in "$C_1$-$C_6$ hydroxyalkyl" is defined to include groups having 1, 2, 3, 4, 5, or 6 carbons in a linear or branched alkyl arrangement wherein a hydrogen contained therein is replaced by a bond to an —OH group.

As used herein, "heteroalkyl" includes both branched and straight-chain saturated aliphatic hydrocarbon groups having the specified number of carbon atoms and at least 1 heteroatom within the chain or branch.

As used herein, "monocycle" includes any stable polyatomic carbon ring of up to 10 atoms and may be unsubstituted or substituted. Examples of such non-aromatic monocycle elements include but are not limited to: cyclobutyl, cyclopentyl, cyclohexyl, and cycloheptyl. Examples of such aromatic monocycle elements include but are not limited to: phenyl.

As used herein, "bicycle" includes any stable polyatomic carbon ring of up to 10 atoms that is fused to a polyatomic carbon ring of up to 10 atoms with each ring being independently unsubstituted or substituted. Examples of such non-aromatic bicycle elements include but are not limited to: decahydronaphthalene. Examples of such aromatic bicycle elements include but are not limited to: naphthalene.

As used herein, "aryl" is intended to mean any stable monocyclic, bicyclic or polycyclic carbon ring of up to 10 atoms in each ring, wherein at least one ring is aromatic, and may be unsubstituted or substituted. Examples of such aryl elements include but are not limited to: phenyl, p-toluenyl (4-methylphenyl), naphthyl, tetrahydro-naphthyl, indanyl, phenanthryl, anthryl or acenaphthyl. In cases where the aryl substituent is bicyclic and one ring is non-aromatic, it is understood that attachment is via the aromatic ring.

The term "heteroaryl", as used herein, represents a stable monocyclic, bicyclic or polycyclic ring of up to 10 atoms in each ring, wherein at least one ring is aromatic and contains from 1 to 4 heteroatoms selected from the group consisting of O, N and S. Bicyclic aromatic heteroaryl groups include phenyl, pyridine, pyrimidine or pyridazine rings that are (a) fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom selected from O, N or S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrrazolyl, indolyl, benzotriazolyl, benzothiazolyl, benzoxazolyl, isoxazolyl, isothiazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

The term "heterocycle", "heterocyclyl" or "heterocyclic" refers to a mono- or poly-cyclic ring system which can be saturated or contains one or more degrees of unsaturation and contains one or more heteroatoms. Preferred heteroatoms include N, O, and/or S, including N-oxides, sulfur oxides, and dioxides. Preferably the ring is three to ten-membered and is either saturated or has one or more degrees of unsaturation. The heterocycle may be unsubstituted or substituted, with multiple degrees of substitution being allowed. Such rings may be optionally fused to one or more of another "heterocyclic" ring(s), heteroaryl ring(s), aryl ring(s), or cycloalkyl ring(s). Examples of heterocycles include, but are not limited to, tetrahydrofuran, pyran, 1,4-dioxane, 1,3-dioxane, piperidine, piperazine, pyrrolidine, morpholine, thiomorpholine, tetrahydrothiopyran, tetrahydrothiophene, 1,3-oxathiolane, and the like.

The term "ester" is intended to a mean an organic compound containing the R—O—CO—R' group.

The term "substitution", "substituted" and "substituent" refers to a functional group as described above in which one or more bonds to a hydrogen atom contained therein are replaced by a bond to non-hydrogen or non-carbon atoms, provided that normal valencies are maintained and that the substitution results in a stable compound. Substituted groups also include groups in which one or more bonds to a carbon(s) or hydrogen(s) atom are replaced by one or more bonds, including double or triple bonds, to a heteroatom. Examples of substituent groups include the functional groups described above, and halogens (i.e., F, Cl, Br, and I); alkyl groups, such as methyl, ethyl, n-propyl, isopropryl, n-butyl, tert-butyl, and trifluoromethyl; hydroxyl; alkoxy groups, such as methoxy, ethoxy, n-propoxy, and isopropoxy; aryloxy groups, such as phenoxy; arylalkyloxy, such as benzyloxy (phenylmethoxy) and p-trifluoromethylbenzyloxy (4-trifluoromethylphenylmethoxy); heteroaryloxy groups; sulfonyl groups, such as trifluoromethanesulfonyl, methanesulfonyl, and p-toluenesulfonyl; nitro, nitrosyl; mercapto; sulfanyl groups, such as methylsulfanyl, ethylsulfanyl and propylsulfanyl; cyano; amino groups, such as amino, methylamino, dimethylamino, ethylamino, and diethylamino; and carboxyl. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

The compounds used in the method of the present invention may be prepared by techniques well known in organic synthesis and familiar to a practitioner ordinarily skilled in the art. However, these may not be the only means by which to synthesize or obtain the desired compounds.

The compounds used in the method of the present invention may be prepared by techniques described in Vogel's Textbook of Practical Organic Chemistry, A. I. Vogel, A. R. Tatchell, B. S. Furnis, A. J. Hannaford, P. W. G. Smith, (Prentice Hall) 5$^{th}$ Edition (1996), March's Advanced Organic Chemistry: Reactions, Mechanisms, and Structure, Michael B. Smith, Jerry March, (Wiley-Interscience) 5$^{th}$ Edition (2007), and references therein, which are incorporated by reference herein. However, these may not be the only means by which to synthesize or obtain the desired compounds.

The various R groups attached to the aromatic rings of the compounds disclosed herein may be added to the rings by standard procedures, for example those set forth in Advanced Organic Chemistry: Part B: Reactions and Synthesis, Francis Carey and Richard Sundberg, (Springer) 5th ed. Edition. (2007), the content of which is hereby incorporated by reference.

Another aspect of the invention comprises a compound used in the method of the present invention as a pharmaceutical composition.

As used herein, the term "pharmaceutically active agent" means any substance or compound suitable for administration to a subject and furnishes biological activity or other direct effect in the treatment, cure, mitigation, diagnosis, or prevention of disease, or affects the structure or any function of the subject. Pharmaceutically active agents include, but are not limited to, substances and compounds described in the Physicians' Desk Reference (PDR Network, LLC; 64th edition; Nov. 15, 2009) and "Approved Drug Products with Therapeutic Equivalence Evaluations" (U.S. Department Of Health And Human Services, 30$^{th}$ edition, 2010), which are hereby incorporated by reference. Pharmaceutically active agents which have pendant carboxylic acid groups may be modified in accordance with the present invention using standard esterification reactions and methods readily available and known to those having ordinary skill in the art of chemical synthesis. Where a pharmaceutically active agent does not possess a carboxylic acid group, the ordinarily skilled artisan will be able to design and incorporate a carboxylic acid group into the pharmaceutically active agent where esterification may subsequently be carried out so long as the modification does not interfere with the pharmaceutically active agent's biological activity or effect.

The compounds used in the method of the present invention may be in a salt form. As used herein, a "salt" is a salt of the instant compounds which has been modified by making acid or base salts of the compounds. In the case of compounds used to treat an infection or disease caused by a pathogen, the salt is pharmaceutically acceptable. Examples of pharmaceutically acceptable salts include, but are not limited to, mineral or organic acid salts of basic residues such as amines; alkali or organic salts of acidic residues such as phenols; alkali or organic salts of acidic residues such as carboxylic acids. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkali earth metal salts, sodium, potassium or lithium. The salts can be made using an organic or inorganic base. Such basic salts are alkali metal salts, such as sodium, potassium or lithium and alkaline earth metal salts, such as magnesium and calcium.

The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. Representative salts also include the sodium, potassium, lithium, magnesium and calcium salts and the like. (See, e.g., Berge et al. (1977) "Pharmaceutical Salts", *J. Pharm. Sci.* 66:1-19).

As used herein, "treating" means preventing, slowing, halting, or reversing the progression of a disease or infection. Treating may also mean improving one or more symptoms of a disease or infection.

The compounds used in the method of the present invention may be administered in various forms, including those detailed herein. The treatment with the compound may be a component of a combination therapy or an adjunct therapy, i.e. the subject or patient in need of the drug is treated or given another drug for the disease in conjunction with one or more of the instant compounds. This combination therapy can be sequential therapy where the patient is treated first with one drug and then the other or the two drugs are given simultaneously. These can be administered independently by the same route or by two or more different routes of administration depending on the dosage forms employed.

As used herein, a "pharmaceutically acceptable carrier" is a pharmaceutically acceptable solvent, suspending agent or vehicle, for delivering the instant compounds to the animal or human. The carrier may be liquid or solid and is selected with the planned manner of administration in mind. Liposomes are also a pharmaceutically acceptable carrier.

The dosage of the compounds administered in treatment will vary depending upon factors such as the pharmacodynamic characteristics of a specific chemotherapeutic agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

A dosage unit of the compounds used in the method of the present invention may comprise a single compound or mixtures thereof with additional antibacterial agents. The compounds can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by injection, topical application, or other methods, into or onto a site of infection, all using dosage forms well known to those of ordinary skill in the pharmaceutical arts.

The compounds used in the method of the present invention can be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit will be in a form suitable for oral, rectal, topical, intravenous or direct injection or parenteral administration. The compounds can be administered alone or mixed with a pharmaceutically acceptable carrier. This carrier can be a solid or liquid, and the type of carrier is generally chosen based on the type of administration being used. The active agent can be co-administered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules.

Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

Techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol. 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.). All of the aforementioned publications are incorporated by reference herein.

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds used in the method of the present invention may also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines. The compounds may be administered as components of tissue-targeted emulsions.

The compounds used in the method of the present invention may also be coupled to soluble polymers as targetable drug carriers or as a prodrug. Such polymers include polyvinylpyrrolidone, pyran copolymer, polyhydroxylpropylmethacrylamide-phenol, polyhydroxyethylasparta-midephenol, or polyethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient compounds and powdered carriers, such as lactose, starch, cellulose derivatives, magnesium stearate, stearic acid, and the like. Similar diluents can be used to make compressed tablets. Both tablets and capsules can be manufactured as immediate release products or as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

For oral administration in liquid dosage form, the oral drug components are combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

The compounds used in the method of the present invention may also be administered in intranasal form via use of suitable intranasal vehicles, or via transdermal routes, using those forms of transdermal skin patches well known to those of ordinary skill in that art. To be administered in the form of a transdermal delivery system, the dosage administration will generally be continuous rather than intermittent throughout the dosage regimen.

Parenteral and intravenous forms may also include minerals and other materials to make them compatible with the type of injection or delivery system chosen.

Each embodiment disclosed herein is contemplated as being applicable to each of the other disclosed embodiments. Thus, all combinations of the various elements described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Example 1. Preparation of Compounds

General Considerations.

Reagents and solvents were obtained from commercial sources and were used without further purification unless otherwise stated. All compounds were prepared in racemic form. All reactions were performed in flame-dried glassware under an argon atmosphere unless otherwise stated, and monitored by TLC using solvent mixtures appropriate to each reaction. All column chromatography was performed on silica gel (40-63 μm). Preparative TLC was conducted on 20×20 cm plates coated with a 1 mm silica layer. Nuclear magnetic resonance spectra were recorded on Bruker 400 or 500 MHz instruments as indicated. Chemical shifts are reported as δ values in ppm referenced to CDCl$_3$ ($^1$H NMR=7.26 and $^{13}$C NMR=77.16) or CD$_3$OD ($^1$H NMR=3.31 and $^{13}$C NMR=49.00). Multiplicity is indicated as follows: s (singlet); d (doublet); t (triplet); q (quartet); p (pentet); dd (doublet of doublets); ddd (doublet of doublet of doublets); dt (doublet of triplets); td (triplet of doublets); m (multiplet); br (broad). All carbon peaks are rounded to one decimal place unless such rounding would cause two close peaks to become identical; in these cases, two decimal places are retained. Low-resolution mass spectra were recorded on a JEOL LCmate (ionization mode: APCI+). For compounds 4 and 5 mass spectra are reported for carbocations corresponding to loss of OH or Cl respectively.

Those having ordinary skill in the art of organic synthesis will appreciate that modifications to general procedures and synthetic routes contained in this application can be used to yield additional derivatives and structurally diverse compounds. Suitable organic transformations are described in March's Advanced Organic Chemistry: Reactions, Mechanisms, and Structure (Wiley-Interscience; 6$^{th}$ edition, 2007), the content of which is hereby incorporated by reference.

Preparation of Diarylthiazepinones (3)

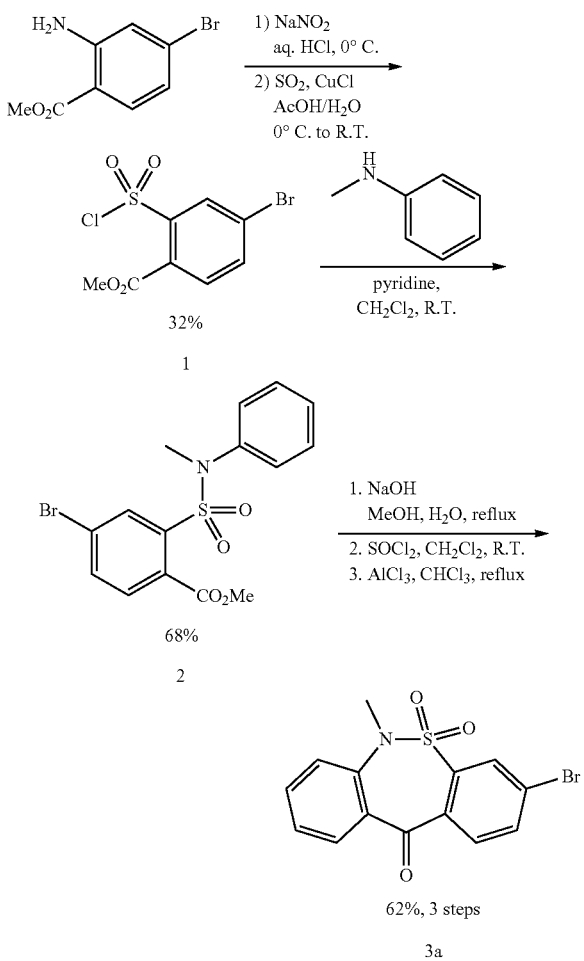

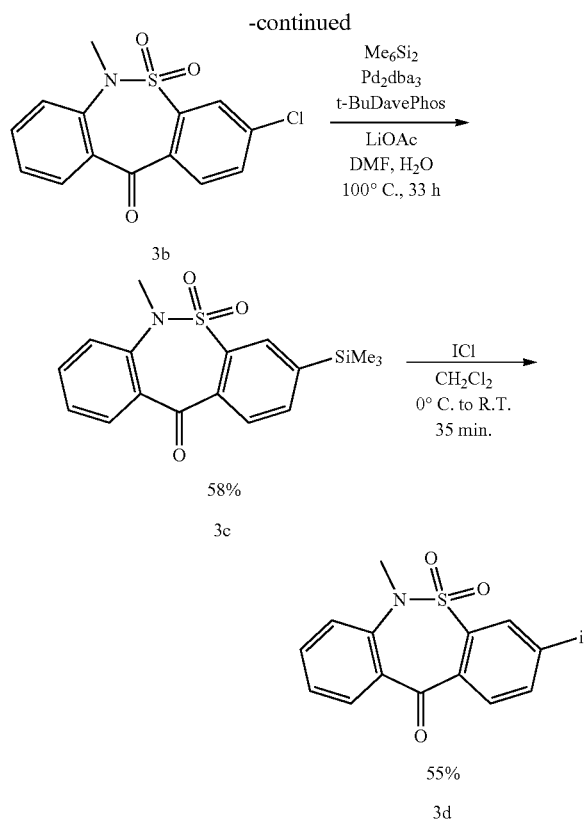

58%

3c

55%

3d

Methyl 4-bromo-2-(chlorosulfonyl)benzoate (1)

A suspension of methyl 2-amino-4-bromobenzoate (10.35 g, 45.0 mmol) in 20% aqueous HCl (29 mL) was sonicated for several minutes and warmed slightly until all clumps were broken up and the mixture was a uniform suspension of fine particles. This mixture was cooled to 0° C., and a solution of $NaNO_2$ (3.11 g, 45.0 mmol) in water (7.5 mL) was added dropwise, maintaining the internal temperature below 5° C. The resulting mixture was then stirred for 2 h at 0° C. Simultaneously, a solution of $SO_2$ (23.1 g, 360 mmol) in AcOH (36.0 mL) and water (3.75 mL) was prepared by bubbling the gas though the mixed solvents at 0° C. until the mass had increased by the required amount. To this $SO_2$ solution was then added CuCl (1.11 g, 11.25 mmol) followed by the diazonium salt solution portionwise over 30 minutes at 0° C. The resulting mixture was then stirred for 1 h at 0° C. and 1 h at room temperature, poured into ice water (150 mL), and extracted with $CH_2Cl_2$ (3×50 mL). The combined organics were poured into saturated aqueous $NaHCO_3$ (75 mL), and solid $NaHCO_3$ was added carefully until effervescence ceased. The organic phase was then separated, washed with brine (50 mL), dried over $Na_2SO_4$, and concentrated to provide the crude sulfonyl chloride as a waxy brown solid (6.11 g, 74 mass % product by NMR, 32% yield). This material was used in the next step without further purification.

Methyl 4-bromo-2-(N-methyl-N-phenylsulfamoyl)benzoate (2)

To a solution of crude methyl 4-bromo-2-(chlorosulfonyl) benzoate 1 (6.04 g, 74% pure, 14.25 mmol) in anhydrous pyridine (10.7 mL) was added N-methylaniline (1.71 mL, 1.68 g, 15.68 mmol) at room temperature, and the resulting mixture was stirred for 1 h. The reaction mixture was then diluted with $CH_2Cl_2$ (100 mL) and washed with 7% aqueous HCl (2×100 mL), brine (100 mL), saturated aqueous $NaHCO_3$ (100 mL), and brine again (100 mL), dried over $Na_2SO_4$, and concentrated to give a yellow-brown oil (2.41 g). This material was purified by column chromatography (9:1 hexanes:EtOAc, 4 column volumes→8:2 hexanes:E-tOAc, 4 column volumes) to provide pure sulfonamide 2 as an oil (3.71 g, 68%). $^1H$ NMR (500 MHz, $CDCl_3$) δ 7.69 (dd, J=8.2, 1.9 Hz, 1H), 7.52 (d, J=1.9 Hz, 1H), 7.38-7.29 (m, 4H), 7.21-7.17 (m, 2H), 3.82 (s, 3H), 3.30 (s, 3H); $^{13}C$ NMR (126 MHz, $CDCl_3$) δ 167.7, 141.0, 137.1, 135.5, 132.8, 132.3, 129.8, 129.3, 128.0, 127.4, 123.9, 53.4, 39.0.

3-Bromo-6-methyldibenzo[c,f][1,2]thiazepin-11 (6H)-one 5,5-dioxide (3a)

To a solution of sulfonamide 2 (3.69 g, 9.60 mmol) in MeOH (24 mL) was added water (12 mL) and NaOH (1.15 g, 28.80 mmol) and the mixture was refluxed for 1 h. Most of the MeOH was then removed in vacuo and the resulting clumpy white mixture was diluted with water (30 mL), acidified with 10% aqueous HCl (20 mL), and extracted with $CH_2Cl_2$(50 mL, 2×20 mL). The combined organics were dried over $Na_2SO_4$ and concentrated to provide the carboxylic acid as a pale-pink glass (3.46 g), which was used in the next step without further purification. The carboxylic acid (3.43 g, 9.26 mmol) was dissolved in thionyl chloride (15 mL), and the solution was stirred for 13 h at room temperature. The volatiles were then removed to provide the crude acyl chloride as a yellow-orange oil. This material was dissolved in $CHCl_3$ (40 mL), aluminum chloride (3.95 g, 29.63 mmol) was added, and the mixture was refluxed for 1 h. The reaction was then cooled to room temperature, quenched with ice water (150 mL), and extracted with $CH_2Cl_2$ (3×50 mL). The combined organics were filtered through a silica plug, washing with additional $CH_2Cl_2$ until all of the product had passed through, and the filtrate was concentrated to provide an off-white solid. This material was recrystallized from MeOH (~250 mL) to provide the pure ketone 3a as cream colored needles (2.08 g, 62% over 3 steps). $^1H$ NMR (500 MHz, $CDCl_3$) δ 8.30 (dd, J=8.1, 1.5 Hz, 1H), 8.11 (t, J=1.0 Hz, 1H), 7.84 (d, J=1.1 Hz, 2H), 7.68-7.62 (m, 1H), 7.41-7.37 (m, 1H), 7.35 (dd, J=8.1, 0.7 Hz, 1H), 3.36 (s, 3H); $^{13}C$ NMR (126 MHz, $CDCl_3$) δ 189.8, 141.5, 138.5, 136.4, 135.1, 135.0, 133.4, 132.3, 131.0, 128.4, 126.9, 126.4, 124.8, 39.2; LR-MS calcd. for $C_{14}H_{11}BrNO_3S$ $[M+H]^+$ 351.96, found 351.85.

3-Chloro-6-methyldibenzo[c,f][1,2]thiazepin-11 (6H)-one 5,5-dioxide (3b)

Ketone 3b was purchased from Ark Pharm Inc. (Libertyville, Ill.) and used without further purification.

6-Methyl-3-(trimethylsilyl)dibenzo[c,f][1,2]thiazepin-11(6H)-one 5,5-dioxide (3c)

Ketone 3c was prepared from the aryl chloride utilizing the trimethylsilylation procedure of Buchwald (McNeill, E. et al. 2007). Ketone 3b (462 mg, 1.50 mmol), $Pd_2dba_3$ (20.6 mg, 0.0225 mmol), t-BuDavePhos (2'-(Di-tert-butylphosphino)-N,N-dimethyl-biphenyl-2-amine, 46.1 mg, 0.135 mmol), and LiOAc (495 mg, 7.50 mmol) were combined under argon. Anhydrous DMF (4.5 mL), water (54 µL, 3.00 mmol), and hexamethyldisilane (369 µL, 1.80 mmol) were then added, and the resulting orange-brown mixture was heated to 100° C. for 33 h. After cooling to room temperature, the reaction mixture was diluted with water (20 mL) and extracted with Et₂O (3×10 mL). The combined organics were washed with water (10 mL), dried over Na₂SO₄, and concentrated to yield a yellow crystalline solid. This crude material was recrystallized from MeOH to obtain pure ketone 3c as fine yellow needles (301 mg, 58%). $^1$H NMR (500 MHz, CDCl₃) δ 8.30 (dd, J=8.1, 1.6 Hz, 1H), 8.04 (d, J=0.8 Hz, 1H), 7.91 (d, J=7.5 Hz, 1H), 7.85 (dd, J=7.6, 1.1 Hz, 1H), 7.63 (ddd, J=8.1, 7.3, 1.7 Hz, 1H), 7.41-7.29 (m, 2H), 3.35 (s, 3H), 0.36 (s, 9H); 13C NMR (126 MHz, CDCl₃) δ 191.2, 147.4, 141.9, 138.3, 136.6, 136.0, 134.8, 132.1, 131.2, 130.5, 129.7, 126.0, 124.6, 39.1, −1.2; LR-MS calcd. for C₁₇H₂NO₃SSi [M+H]⁺346.09, found 345.86.

3-Iodo-6-methyldibenzo[c,f][1,2]thiazepin-11 (6H)-one 5,5-dioxide (3d)

To a solution of trimethylsilylketone 3c (108 mg, 0.313 mmol) in anhydrous CH₂Cl₂ (0.94 mL) at 0° C. was added a solution of iodine monochloride (173 mg, 1.06 mmol) in anhydrous CH₂Cl₂ (0.63 mL) dropwise over 3 min. The resulting dark-brown solution was allowed to warm to room temperature, stirred for 35 min (extended reaction times produce polyiodinated byproducts), and quenched with saturated aqueous Na₂S₂O₃ (3 mL). The resulting mixture was diluted with water (15 mL) and extracted with CH₂Cl₂ (2×15 mL). The combined organics were washed with water (15 mL), dried over Na₂SO₄, and concentrated to yield a yellow solid. This material was purified by column chromatography (1:1 CH₂Cl₂:hexanes) to yield impure product. This crude product was recrystallized from MeOH and the resulting fine-white needles were dissolved in CH₂Cl₂ and concentrated, causing a second crystallization to occur once most of the solvent had been removed. The powdery white crystals thus obtained were washed with ice-cold MeOH and dried to yield the pure ketone 3d (68.4 mg, 55%). $^1$H NMR (400 MHz, CDCl₃) δ 8.32-8.27 (m, 2H), 8.06 (dd, J=8.1, 1.7 Hz, 1H), 7.69-7.62 (m, 2H), 7.38 (ddd, J=8.2, 7.3, 1.1 Hz, 1H), 7.34 (dd, J=8.1, 0.9 Hz, 1H), 3.35 (s, 3H); ¹³C NMR (101 MHz, CDCl₃) δ 190.1, 142.4, 141.5, 138.1, 135.6, 135.1, 133.9, 133.1, 132.2, 131.0, 126.3, 124.7, 98.7, 39.2; LR-MS calcd. for C₁₄H₁₁INO₃S [M+H]⁺ 399.95, found 399.78.

Preparation of Diarylthiazepinyl Chlorides (5)

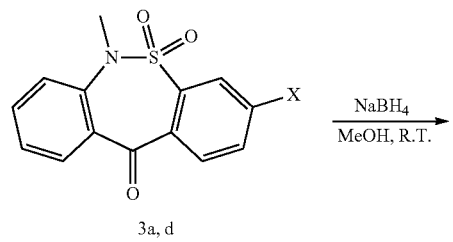

Scheme 2. Preparation of diarylthiazepinyl chlorides.

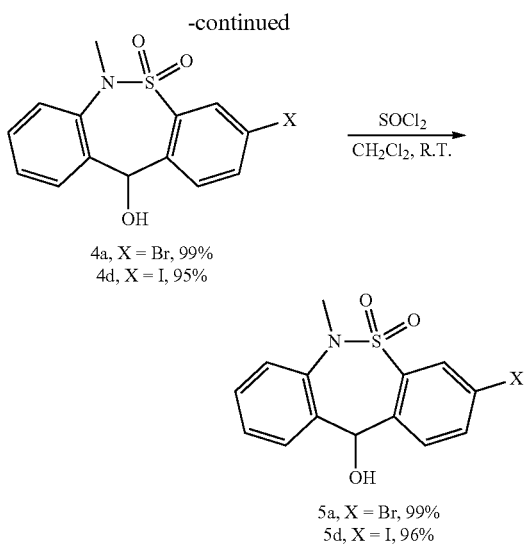

4a, X = Br, 99%
4d, X = I, 95%

5a, X = Br, 99%
5d, X = I, 96%

General Procedure for Preparation of Diarylthiazepinyl Alcohols (4)

Sodium borohydride (2 equivalents) was added to an ice-cooled solution (or suspension) of the appropriate ketone 3 (1 equivalent) in MeOH (0.143 M based on 3) and the mixture was allowed to warm to room temperature and stirred until TLC indicated the complete consumption of starting material. The reaction was then quenched with saturated aqueous ammonium chloride (5 mL per mmol 3) and saturated aqueous NaHCO₃ (5 mL per mmol 3). The MeOH was evaporated and the precipitate was filtered, washed with water, and dried (alternatively, the residue was extracted with EtOAc and the combined organic layers were washed with water, dried over Na₂SO₄, filtered, and concentrated). The resulting product 4 was used in the next step without further purification.

3-Bromo-11-hydroxy-6-methyl-6,1-dihydrodibenzo [c,f][1,2]thiazepine 5,5-dioxide (4a)

The product 4a was prepared according to the general procedure and obtained as a white solid (1.85 g, 99%). $^1$H NMR (500 MHz, CDCl₃) δ 8.11 (d, J=2.0 Hz, 1H), 7.73 (dd, J=8.2, 2.0 Hz, 1H), 7.61 (dd, J=7.7, 1.0 Hz, 1H), 7.57 (d, J=8.2 Hz, 1H), 7.41 (td, J=7.6, 1.5 Hz, 1H), 7.37-7.30 (m, 2H), 5.93 (d, J=9.7 Hz, 1H), 4.16 (d, J=9.7 Hz, 1H), 3.20 (s, 3H); ¹³C NMR (126 MHz, CDCl₃) δ 138.9, 138.8, 136.9, 136.4, 135.3, 131.8, 131.5, 131.0, 130.1, 127.9, 127.0, 122.7, 76.2, 39.4; LR-MS calcd. for C₁₄H₁₁BrNO₂S [M−OH]335.97, found 335.89.

11-Hydroxy-3-iodo-6-methyl-6,11-dihydrodibenzo [c,f][1,2]thiazepine 5,5-dioxide (4d)

The product 4d was prepared according to the general procedure and obtained as a white solid (74.8 mg, 95%). $^1$H NMR (500 MHz, CDCl₃) (observed as a ~4:1 ratio of 2 conformers, resulting in partial integrals) δ 8.27 (d, J=1.8 Hz, 1H), 7.99 (dd, J=7.7, 1.1 Hz, 0.2H), 7.93 (dd, J=8.1, 1.8 Hz, 0.8H), 7.68 (d, J=7.2 Hz, 0.2H), 7.65-7.58 (m, 1H), 7.53 (td, J=7.6, 1.3 Hz, 0.2H), 7.44-7.37 (m, 1.8H), 7.37-7.29 (m, 1.8H), 5.92 (s, 1H), 4.40 (d, J=9.6 Hz, 0.2H), 4.15 (d, J=7.5 Hz, 0.8H), 3.20 (s, 2.4H), 3.14 (s, 0.6H); ¹³C NMR (126 MHz, CDCl₃) (additional peaks due to conformers) δ 142.4, 138.8, 138.7, 137.5, 136.5, 135.4, 133.6, 132.1, 131.7, 131.4, 130.6, 130.1, 130.0, 128.9, 128.4, 127.9, 127.6, 127.0, 126.9, 93.6, 76.2, 39.3; LR-MS calcd. for $C_{14}H_1INO_2S$ [M–OH]$^+$ 383.96, found 383.71.

General Procedure for Preparation of Diarylthiazepinyl Chlorides (5)

Thionyl chloride (6 equivalents) was added dropwise to a solution of the appropriate alcohol 4 (1 equivalent) in anhydrous $CH_2Cl_2$ (0.143 M based on 4). The reaction mixture was stirred overnight at room temperature and then concentrated to provide the corresponding chloride 5, which was used directly in the following reactions without further purification.

3-Bromo-11-chloro-6-methyl-6,11-dihydrodibenzo[c,f][1,2]thiazepine 5,5-dioxide (5a)

The product 5a was prepared according to the general procedure and obtained as a white solid (1.92 g, 99%). $^1$H NMR (400 MHz, CDCl$_3$) δ 8.14 (d, J=2.1 Hz, 1H), 7.66 (dd, J=8.3, 2.1 Hz, 1H), 7.55-7.49 (m, 2H), 7.45-7.40 (m, 2H), 7.39-7.33 (m, 1H), 6.10 (s, 1H), 3.58 (s, 3H); $^{13}$C NMR (101 MHz, CDCl$_3$) δ 142.0, 139.2, 137.6, 135.6, 134.1, 133.0, 131.7, 131.0, 130.2, 129.5, 129.0, 124.3, 63.7, 39.3; LR-MS calcd. for $C_{14}H_{11}BrNO_2S$ [M–Cl]$^+$ 335.97, found 335.79.

3,11-dichloro-6-methyl-6,11-dihydrodibenzo[c,f][1,2]thiazepine 5,5-dioxide (5b)

Chloride 5b was purchased from Ark Pharm Inc. (Libertyville, Ill.) and used without further purification.

11-Chloro-3-iodo-6-methyl-6,11-dihydrodibenzo[c,f][1,2]thiazepine 5,5-dioxide (5d)

The product 5d was prepared according to the general procedure and obtained as a gray solid (73.4 mg, 96%). $^1$H NMR (400 MHz, CDCl$_3$) δ 8.32 (d, J=1.8 Hz, 1H), 7.87 (dd, J=8.2, 1.8 Hz, 1H), 7.57-7.48 (m, 2H), 7.43 (d, J=7.1 Hz, 1H), 7.39-7.33 (m, 1H), 7.27 (d, J=7.1 Hz, 1H), 6.08 (s, 1H), 3.57 (s, 3H); 3C NMR (101 MHz, CDCl$_3$) δ 141.8, 141.5, 139.3, 137.6, 136.7, 134.7, 132.9, 131.7, 130.1, 129.5, 129.0, 95.4, 63.8, 39.3; LR-MS calcd. for $C_{14}H_{11}INO_2S$ [M–Cl]$^+$ 383.96, found 383.70.

Preparation of Diarylthiazepinamine Esters (6)

Scheme 3. Preparation of diarylthiazepinamine esters.

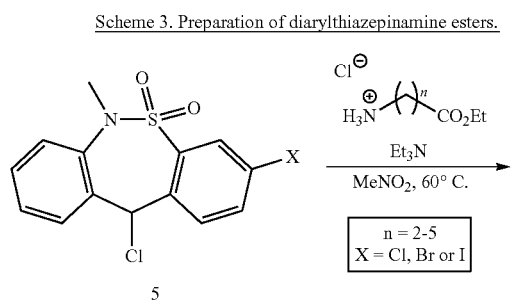

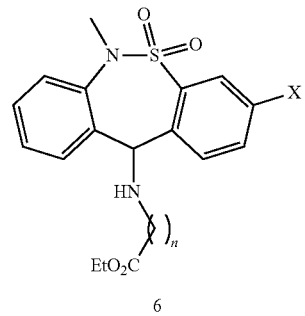

General Procedure for Preparation of Diarylthiazepinamines

To a suspension of the appropriate chloride 5 (1 equivalent) in nitromethane (0.5 M based on 5) was added an aminoester hydrochloride (1.2 equivalents) and Et$_3$N (2.4 equivalents) and the mixture was warmed to 60° C. and left to stir until TLC indicated that the reaction was complete (typically <1 h). The reaction mixture was then concentrated in vacuo and purified directly by column chromatography. Alternatively, the concentrated reaction residue was partitioned between Et$_2$O (20 mL per mmol 5) and water (20 mL per mmol 5). The ethereal layer was separated and the aqueous extracted again with Et$_2$O (20 mL per mmol 5). The combined organics were washed with water (20 mL per mmol 5) and 10% NH$_4$OH (20 mL per mmol 5), dried over Na$_2$SO$_4$, and concentrated to yield the product. If necessary, the product was further purified by column chromatography or preparative TLC.

Ethyl 3-((3-bromo-6-methyl-5,5-dioxido-6,11l-dihydrodibenzo[c,f][1,2]thiazepin-11-yl)amino)propanoate (6a)

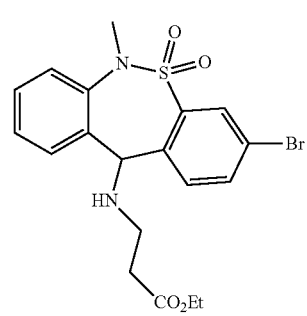

The product 6a was prepared according to the general procedure and purified by preparative TLC (20:1 CH$_2$Cl$_2$:Et$_2$O) to provide a viscous, pale-yellow oil (30.8 mg, 68%). $^1$H NMR (500 MHz, CDCl$_3$) δ 8.09 (d, J=2.0 Hz, 1H), 7.61 (dd, J=8.3, 2.0 Hz, 1H), 7.42-7.33 (m, 4H), 7.29 (td, J=7.5, 1.3 Hz, 1H), 5.03 (s, 1H), 4.12 (q, J=7.1 Hz, 2H), 3.39 (s, 3H), 2.80-2.69 (m, 2H), 2.56-2.43 (m, 2H), 2.47 (br s, 1H), 1.24 (t, J=7.1 Hz, 3H); $^{13}$C NMR (126 MHz, CDCl$_3$) δ 172.7, 140.7, 138.8, 138.6, 137.3, 135.4, 131.3, 131.2, 129.9, 129.6, 128.3, 128.0, 122.1, 65.9, 60.7, 43.6, 38.6, 34.8, 14.3.

Ethyl 3-((3-iodo-6-methyl-5,5-dioxido-6,11-dihydrodibenzo[c,f][1,2]thiazepin-11-yl)amino)propanoate (6b)

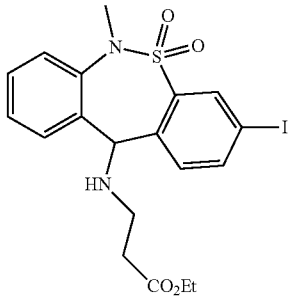

The product 6b was prepared according to the general procedure and purified by preparative TLC (20:1 CH$_2$Cl$_2$:Et$_2$O) to provide a viscous, colorless oil (46.8 mg, 94%). $^1$H NMR (500 MHz, CDCl$_3$) δ 8.26 (d, J=1.8 Hz, 1H), 7.81 (dd, J=8.1, 1.8 Hz, 1H), 7.41-7.37 (m, 2H), 7.35 (td, J=7.4, 1.6 Hz, 1H), 7.28 (td, J=7.5, 1.4 Hz, 1H), 7.25 (d, J=8.2 Hz, 1H), 5.02 (s, 1H), 4.12 (q, J=7.1 Hz, 2H), 3.38 (s, 3H), 2.80-2.69 (m, 2H), 2.57-2.43 (m, 2H), 2.44 (br s, 1H), 1.24 (t, J=7.1 Hz, 3H); $^{13}$C NMR (126 MHz, CDCl$_3$) δ 172.7, 141.3, 140.6, 138.7, 138.6, 137.9, 136.8, 131.2, 129.8, 129.5, 128.3, 128.0, 93.0, 65.9, 60.7, 43.5, 38.5, 34.8, 14.3.

Ethyl 4-((3-bromo-6-methyl-5,5-dioxido-6,11-dihydrodibenzo[c,f][1,2]thiazepin-11-yl)amino)butanoate (6c)

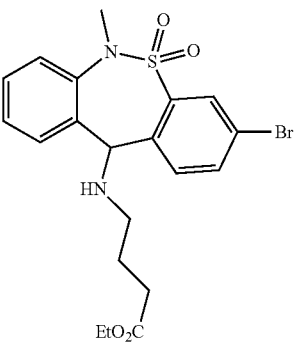

The product 6c was prepared according to the general procedure and purified directly by column chromatography (20:1 CH$_2$Cl$_2$:Et$_2$O, 4 column volumes→7:3 CH$_2$Cl$_2$:Et$_2$O, 2 column volumes) to provide a viscous, nearly colorless oil (43.5 mg, 93%). $^1$H NMR (500 MHz, CDCl$_3$) δ 8.10 (d, J=2.0 Hz, 1H), 7.61 (dd, J=8.2, 2.1 Hz, 1H), 7.40-7.33 (m, 4H), 7.31-7.27 (m, 1H), 5.00 (s, 1H), 4.09 (q, J=7.1 Hz, 2H), 3.35 (s, 3H), 2.51 (t, J=6.9 Hz, 2H), 2.41-2.29 (m, 2H), 2.13 (br s, 1H), 1.81 (p, J=7.1 Hz, 2H), 1.22 (t, J=7.1 Hz, 3H); $^{13}$C NMR (126 MHz, CDCl$_3$) δ 173.6, 140.5, 138.7, 138.4, 137.4, 135.3, 131.43, 131.37, 130.2, 129.5, 128.2, 128.0, 122.0, 66.0, 60.5, 47.3, 38.8, 34.3, 32.2, 25.3, 14.3.

Ethyl 5-((3-bromo-6-methyl-5,5-dioxido-6,11-dihydrodibenzo[c,f][1,2]thiazepin-11-yl)amino)pentanoate (6d)

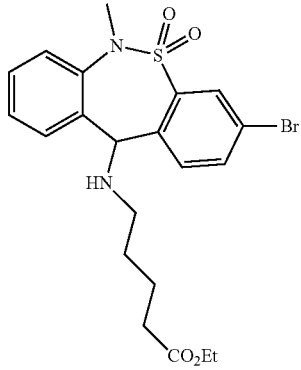

The product 6d was prepared according to the general procedure and purified by preparative TLC (6:4 hexanes:EtOAc) to provide a viscous, colorless oil (40.8 mg, 85%). $^1$H NMR (500 MHz, CDCl$_3$) δ 8.10 (d, J=2.1 Hz, 1H), 7.62 (dd, J=8.2, 2.1 Hz, 1H), 7.40-7.34 (m, 4H), 7.32-7.27 (m, 1H), 4.98 (s, 1H), 4.10 (q, J=7.1 Hz, 2H), 3.36 (s, 3H), 2.47 (t, J=7.0 Hz, 2H), 2.27 (t, J=7.4 Hz, 2H), 2.07 (br s, 1H), 1.69-1.59 (m, 2H), 1.57-1.46 (m, 2H), 1.24 (t, J=7.1 Hz, 3H); 13C NMR (126 MHz, CDCl$_3$) δ 173.6, 140.5, 138.7, 138.6, 137.4, 135.3, 131.5, 131.4, 130.2, 129.5, 128.3, 128.1, 122.1, 66.3, 60.4, 47.8, 38.8, 34.2, 29.6, 22.7, 14.4.

Ethyl 5-((3-iodo-6-methyl-5,5-dioxido-6,11-dihydrodibenzo[c,f][1,2]thiazepin-11-yl)amino)pentanoate (6e)

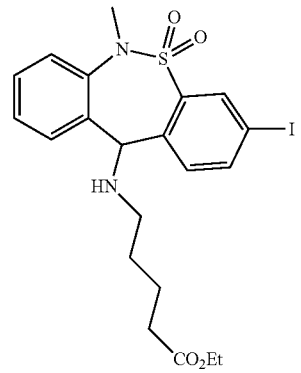

The product 6e was prepared according to the general procedure and purified by preparative TLC (20:1 CH$_2$Cl$_2$:Et$_2$O) to provide a viscous, nearly colorless oil (30.1 mg, 57%). $^1$H NMR (500 MHz, CDCl$_3$) δ 8.27 (d, J=1.8 Hz, 1H), 7.81 (dd, J=8.1, 1.8 Hz, 1H), 7.40-7.33 (m, 3H), 7.31-7.26 (m, 1H), 7.21 (d, J=8.2 Hz, 1H), 4.97 (s, 1H), 4.11 (q, J=7.1 Hz, 2H), 3.36 (s, 3H), 2.48 (t, J=7.0 Hz, 2H), 2.27 (t, J=7.4 Hz, 2H), 2.06 (br s, 1H), 1.69-1.59 (m, 2H), 1.57-1.46 (m, 2H), 1.24 (t, J=7.1 Hz, 3H); $^{13}$C NMR (126 MHz, CDCl$_3$)

δ 173.6, 141.3, 140.6, 138.7, 138.1, 137.0, 131.5, 130.2, 129.5, 128.2, 128.1, 92.9, 66.3, 60.4, 47.8, 38.8, 34.2, 29.6, 22.8, 14.4.

Ethyl 6-((3-bromo-6-methyl-5,5-dioxido-6,11-dihydrodibenzo[c,f][1,2]thiazepin-11-yl)amino)hexanoate (6f)

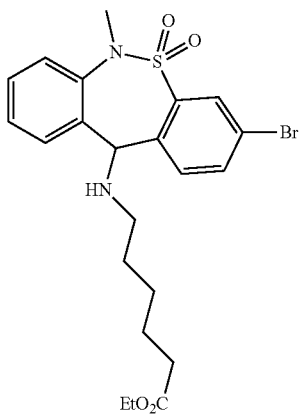

6f

The product 6f was prepared according to the general procedure and purified directly by column chromatography (20:1 CH$_2$Cl$_2$:Et$_2$O, 4 column volumes→7:3 CH$_2$Cl$_2$:Et$_2$O, 2 column volumes) to provide a viscous, pale-yellow oil (43.2 mg, 87%). $^1$H NMR (400 MHz, CDCl$_3$) δ 8.10 (d, J=2.0 Hz, 1H), 7.62 (dd, J=8.2, 2.0 Hz, 1H), 7.43-7.33 (m, 4H), 7.32-7.27 (m, 1H), 5.01 (s, 1H), 4.10 (q, J=7.1 Hz, 2H), 3.35 (s, 3H), 2.54-2.40 (m, 2H), 2.26 (t, J=7.4 Hz, 2H), 2.21 (br s, 1H), 1.64-1.55 (m, 2H), 1.55-1.45 (m, 2H), 1.37-1.28 (m, 2H), 1.23 (t, J=7.1 Hz, 3H); 13C NMR (101 MHz, CDCl$_3$) δ 173.7, 140.6, 138.8, 138.3, 137.2, 135.4, 131.6, 131.3, 130.3, 129.6, 128.2, 128.1, 122.1, 66.3, 60.4, 48.0, 38.8, 34.3, 29.8, 26.9, 24.9, 14.4.

Ethyl 6-((3-iodo-6-methyl-5,5-dioxido-6,11-dihydrodibenzo[c,f][1,2]thiazepin-11-yl)amino)hexanoate (6g)

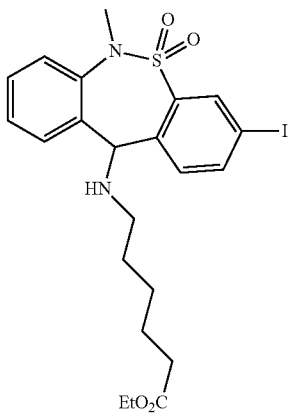

6g

The product 6g was prepared according to the general procedure and purified directly by column chromatography (20:1 CH$_2$Cl$_2$:Et$_2$O, 4 column volumes→7:3 CH$_2$Cl$_2$:Et$_2$O, 2 column volumes) to provide a viscous, pale-yellow oil (47.4 mg, 87%). $^1$H NMR (400 MHz, CDCl$_3$) δ 8.26 (d, J=1.8 Hz, 1H), 7.81 (dd, J=8.1, 1.8 Hz, 1H), 7.40-7.27 (m, 4H), 7.21 (d, J=8.2 Hz, 1H), 4.96 (s, 1H), 4.10 (q, J=7.1 Hz, 2H), 2.46 (t, J=7.1 Hz, 2H), 2.26 (t, J=7.4 Hz, 2H), 1.99 (br s, 1H), 1.65-1.54 (m, 2H), 1.54-1.44 (m, 2H), 1.38-1.27 (m, 2H), 1.23 (t, J=7.1 Hz, 3H); $^{13}$C NMR (101 MHz, CDCl$_3$) δ 173.7, 141.2, 140.6, 138.8, 138.7, 138.2, 136.9, 131.4, 130.1, 129.4, 128.2, 128.1, 92.9, 66.3, 60.3, 48.0, 38.7, 34.3, 29.9, 26.9, 24.9, 14.4.

Ethyl 3-((3-chloro-6-methyl-5,5-dioxido-6,11-dihydrodibenzo[c,f][1,2]thiazepin-11-yl)amino)propanoate (6h)

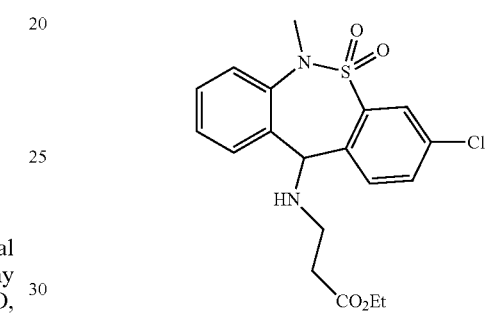

6h

The product 6h was prepared according to the general procedure and purified directly by column chromatography (20:1 CH$_2$Cl$_2$:Et$_2$O, 3 column volumes→7:3 CH$_2$Cl$_2$:Et$_2$O, 3 column volumes) to provide a viscous, colorless oil (393 mg, 96%). $^1$H NMR (400 MHz, CDCl$_3$) δ 7.96-7.93 (m, 1H), 7.49-7.43 (m, 2H), 7.42-7.33 (m, 3H), 7.31-7.26 (m, 1H), 5.05 (s, 1H), 4.12 (q, J=7.1 Hz, 2H), 3.39 (s, 3H), 2.83-2.68 (m, 2H), 2.59-2.41 (m, 2H), 2.51 (br s, 1H), 1.24 (t, J=7.1 Hz, 3H); 13C NMR (101 MHz, CDCl$_3$) δ 172.7, 140.6, 138.8, 138.6, 136.9, 134.5, 132.4, 131.1, 129.9, 129.5, 128.5, 128.3, 128.1, 65.9, 60.7, 43.6, 38.6, 34.9, 14.3.

Ethyl 5-((3-chloro-6-methyl-5,5-dioxido-6,11-dihydrodibenzo[c,f][1,2]thiazepin-11-yl)amino)pentanoate (6i)

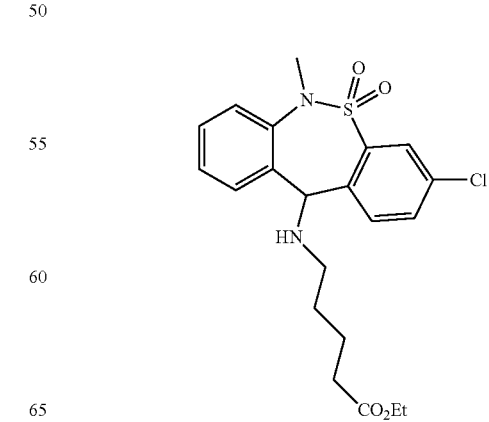

6i

The product 6i was prepared according to the general procedure and purified by column chromatography (40:1 $CH_2Cl_2$:$Et_2O$, 4 column volumes—20:1 $CH_2Cl_2$:$Et_2O$, 2 column volumes→7:3 $CH_2Cl_2$:$Et_2O$, 2 column volumes) to provide a viscous, nearly colorless oil (256 mg, 59%). $^1$H NMR (400 MHz, CDCl$_3$) δ 7.96 (d, J=2.1 Hz, 1H), 7.48-7.33 (m, 5H), 7.32-7.27 (m, 1H), 5.00 (s, 1H), 4.11 (q, J=7.1 Hz, 2H), 3.36 (s, 3H), 2.48 (t, J=7.0 Hz, 2H), 2.27 (t, J=7.3 Hz, 2H), 2.08 (br s, 1H), 1.71-1.57 (m, 2H), 1.57-1.46 (m, 2H), 1.24 (t, J=7.1 Hz, 3H); $^{13}$C NMR (101 MHz, CDCl$_3$) δ 173.6, 140.5, 138.7, 137.0, 134.4, 132.3, 131.3, 130.3, 129.5, 128.6, 128.2, 128.1, 66.3, 60.4, 47.8, 38.8, 34.2, 29.6, 22.8, 14.4.

Ethyl 6-((3-chloro-6-methyl-5,5-dioxido-6,11-dihydrodibenzo[c,f][1,2]thiazepin-11-yl)amino)hexanoate (6j)

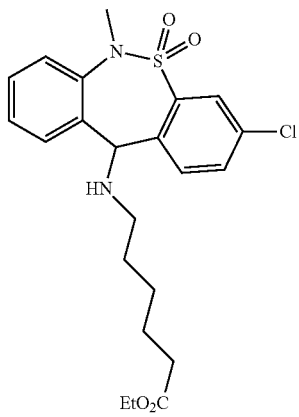

6j

The product 6j was prepared according to the general procedure and purified by preparative TLC (6:4 hexanes: EtOAc) to provide a viscous, pale-yellow oil (42.0 mg, 93%). $^1$H NMR (500 MHz, CDCl$_3$) δ 7.95 (d, J=2.1 Hz, 1H), 7.48-7.40 (m, 2H), 7.40-7.33 (m, 3H), 7.29 (td, J=7.2, 1.8 Hz, 1H), 4.99 (s, 1H), 4.10 (q, J=7.1 Hz, 2H), 3.36 (s, 3H), 2.46 (t, J=7.1 Hz, 2H), 2.26 (t, J=7.5 Hz, 2H), 1.96 (br s, 1H), 1.63-1.54 (m, 2H), 1.54-1.43 (m, 2H), 1.37-1.28 (m, 2H), 1.23 (t, J=7.1 Hz, 3H); $^{13}$C NMR (126 MHz, CDCl$_3$) δ 173.8, 140.4, 138.7, 138.6, 136.9, 134.4, 132.3, 131.3, 130.2, 129.5, 128.6, 128.3, 128.1, 66.3, 60.4, 48.0, 38.8, 34.3, 29.9, 26.9, 24.9, 14.4.

Preparation of Diarylthiazepinamine Carboxylic Acids (7)

Scheme 4. Preparation of diarylthiazepinamine carboxylic acids.

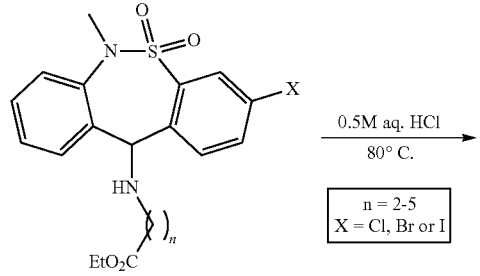

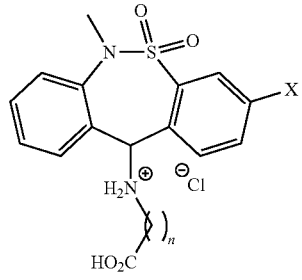

7

General Procedure for Preparation of Carboxylic Acids

The appropriate ester 6 (0.04 M concentration) was heated in aqueous HCl (0.5 M) at 80° C. until TLC indicated the complete consumption of starting material (typically <2 h). The reaction mixture was then concentrated and dried thoroughly in vacuo to provide the pure HCl salt of the corresponding amino carboxylic acid. If desired, the obtained products may be triturated with hexanes and then concentrated to provide a powdered solid.

3-((3-Bromo-6-methyl-5,5-dioxido-6,1-dihydrodibenzo[c,f][1,2]thiazepin-11-yl)amino)propanoic acid hydrochloride salt (7a)

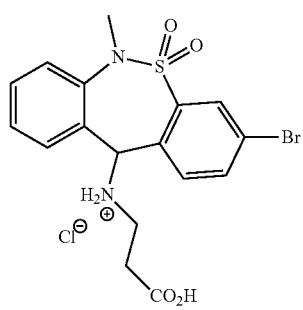

7a

The product 7a was prepared according to the general procedure and obtained as a glassy, white foam (10.0 mg, 66%). $^1$H NMR (500 MHz, CD$_3$OD) δ 8.22 (d, J=2.0 Hz, 1H), 8.02 (dd, J=8.1, 1.9 Hz, 1H), 7.86 (d, J=8.1 Hz, 1H), 7.77 (d, J=7.6 Hz, 1H), 7.65 (t, J=7.5 Hz, 1H), 7.60 (d, J=7.2 Hz, 1H), 7.49 (t, J=7.1 Hz, 1H), 6.02 (s, 1H), 3.30-3.25 (m, 1H), 3.28 (s, 3H), 3.11 (dt, J=12.5, 6.1 Hz, 1H), 2.82-2.69 (m, 2H); $^{13}$C NMR (126 MHz, CD$_3$OD) δ 174.2, 142.3, 142.1, 138.3, 137.2, 134.7, 133.6, 132.3, 129.3, 128.3, 128.2, 127.3, 126.7, 68.1, 44.4, 39.3, 30.7.

3-((3-Iodo-6-methyl-5,5-dioxido-6,11-dihydrodibenzo[c,f][1,2]thiazepin-11-yl)amino) propanoic acid hydrochloride salt (7b)

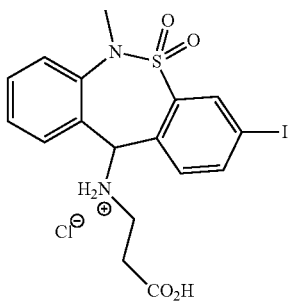

7b

The product 7b was prepared according to the general procedure and obtained as a glassy, white foam (10.0 mg, 99%). $^1$H NMR (500 MHz, CD$_3$OD) δ 8.38 (d, J=1.8 Hz, 1H), 8.22 (dd, J=8.0, 1.8 Hz, 1H), 7.74 (dd, J=7.8, 1.3 Hz, 1H), 7.68-7.62 (m, 2H), 7.59 (dd, J=8.1, 1.2 Hz, 1H), 7.49 (td, J=7.6, 1.3 Hz, 1H), 5.94 (s, 1H), 3.29-3.24 (m, 1H), 3.27 (s, 3H), 3.10 (ddd, J=12.7, 7.2, 5.7 Hz, 1H), 2.80-2.68 (m, 2H); $^{13}$C NMR (126 MHz, CD$_3$OD) δ 174.2, 144.5, 142.4, 141.6, 138.0, 136.8, 134.6, 133.6, 129.2, 128.6, 128.4, 127.3, 98.1, 68.4, 44.3, 39.4, 30.7.

4-((3-Bromo-6-methyl-5,5-dioxido-6,11-dihydrodibenzo[c,f][1,2]thiazepin-11-yl)amino)butanoic acid hydrochloride salt (7c)

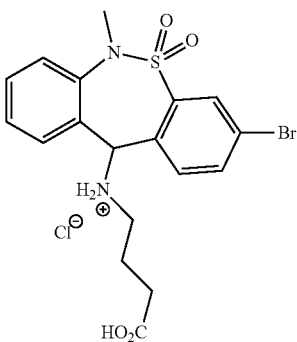

7c

The product 7c was prepared according to the general procedure and obtained as a white solid (15.3 mg, 88%). $^1$H NMR (500 MHz, CD$_3$OD) δ 8.22 (d, J=2.0 Hz, 1H), 8.01 (dd, J=8.2, 2.1 Hz, 1H), 7.82 (d, J=8.2 Hz, 1H), 7.72 (dd, J=7.8, 1.0 Hz, 1H), 7.67-7.62 (m, 1H), 7.59 (dd, J=8.0, 1.0 Hz, 1H), 7.51-7.46 (m, 1H), 5.94 (s, 1H), 3.26 (s, 3H), 3.07 (ddd, J=12.4, 9.0, 5.9 Hz, 1H), 2.93 (ddd, J=12.4, 8.9, 6.4 Hz, 1H), 2.42 (t, J=6.8 Hz, 2H), 2.02-1.85 (m, 2H); $^{13}$C NMR (126 MHz, CD$_3$OD) δ 176.4, 142.4, 142.1, 138.2, 137.0, 134.6, 133.5, 132.2, 129.2, 128.53, 128.47, 127.6, 126.6, 67.7, 47.9, 39.5, 31.7, 22.2.

5-((3-Bromo-6-methyl-5,5-dioxido-6,11-dihydrodibenzo[c,f][1,2]thiazepin-11-yl)amino)pentanoic acid hydrochloride salt (7d)

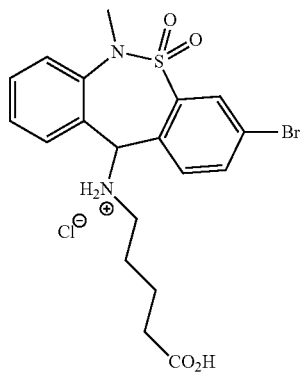

7d

The product 7d was prepared according to the general procedure and obtained as a glassy, white foam (6.6 mg, 45%). $^1$H NMR (400 MHz, CD$_3$OD) 8.23 (s, 1H), 8.03 (d, J=8.1 Hz, 1H), 7.80 (d, J=8.1 Hz, 1H), 7.71 (d, J=7.6 Hz, 1H), 7.65 (t, J=7.7 Hz, 1H), 7.58 (d, J=8.0 Hz, 1H), 7.49 (t, J=7.5 Hz, 1H), 5.92 (s, 1H), 3.23 (s, 3H), 3.04-2.94 (m, 1H), 2.92-2.81 (m, 1H), 2.32 (t, J=6.9 Hz, 2H), 1.79-1.65 (m, 2H), 1.65-1.54 (m, 2H).

5-((3-Iodo-6-methyl-5,5-dioxido-6,11-dihydrodibenzo[c,f][1,2]thiazepin-11-yl)amino)pentanoic acid hydrochloride salt (7e)

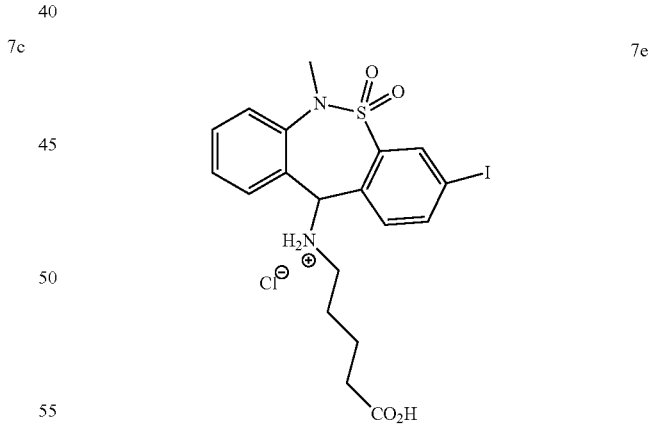

7e

The product 7e was prepared according to the general procedure and obtained as a white solid (10.5 mg, 65%). $^1$H NMR (400 MHz, CD$_3$OD) δ 8.38 (d, J=1.7 Hz, 1H), 8.22 (dd, J=8.0, 1.7 Hz, 1H), 7.71 (d, J=7.7 Hz, 1H), 7.68-7.60 (m, 2H), 7.57 (d, J=7.1 Hz, 1H), 7.48 (t, J=7.5 Hz, 1H), 5.88 (s, 1H), 3.23 (s, 3H), 3.04-2.93 (m, 1H), 2.90-2.80 (m, 1H), 2.31 (t, J=6.9 Hz, 2H), 1.79-1.65 (m, 2H), 1.65-1.54 (m, 2H); $^{13}$C NMR (101 MHz, CD$_3$OD) δ 176.8, 144.5, 142.6, 141.4, 138.0, 136.7, 134.7, 133.5, 129.1, 128.8, 128.5, 127.1, 98.0, 68.0, 48.1, 39.7, 33.8, 26.4, 22.7.

6-((3-Bromo-6-methyl-5,5-dioxido-6,11-dihydrod-ibenzo[c,f][1,2]thiazepin-11-yl)amino)hexanoic acid hydrochloride salt (7f)

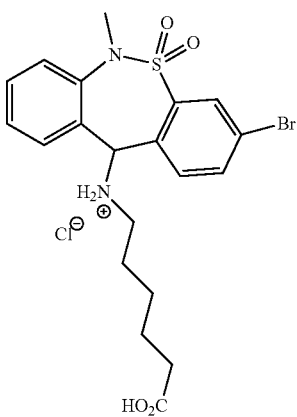

7f

The product 7f was prepared according to the general procedure and obtained as a white, glassy foam (18.2 mg, 94%). $^1$H NMR (500 MHz, CD$_3$OD) δ 8.22 (d, J=2.1 Hz, 1H), 8.03 (dd, J=8.2, 2.1 Hz, 1H), 7.85 (d, J=8.2 Hz, 1H), 7.76 (dd, J=7.8, 1.2 Hz, 1H), 7.68-7.62 (m, 1H), 7.58 (dd, J=8.1, 1.1 Hz, 1H), 7.49 (td, J=7.7, 1.2 Hz, 1H), 5.99 (s, 1H), 3.24 (s, 3H), 2.98 (ddd, J=11.9, 10.5, 5.5 Hz, 1H), 2.87-2.80 (m, 1H), 2.28 (t, J=7.3 Hz, 2H), 1.77-1.62 (m, 2H), 1.62-1.54 (m, 2H), 1.39-1.30 (m, 2H); $^{13}$C NMR (126 MHz, CD$_3$OD) 177.2, 142.5, 141.9, 138.3, 137.2, 134.8, 133.5, 132.2, 129.2, 128.5, 128.4, 127.1, 126.6, 67.6, 48.2, 39.7, 34.3, 26.9, 26.6, 25.3.

6-((3-Iodo-6-methyl-5,5-dioxido-6,11-dihydrod-ibenzo[c,f][1,2]thiazepin-11-yl)amino)hexanoic acid hydrochloride salt (7g)

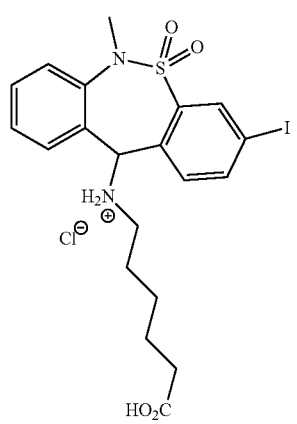

7g

The product 7g was prepared according to the general procedure and obtained as a glassy, white foam (19.7 mg, 91%). $^1$H NMR (500 MHz, CD$_3$OD) δ 8.37 (d, J=1.8 Hz, 1H), 8.22 (dd, J=8.0, 1.8 Hz, 1H), 7.76 (dd, J=7.8, 1.2 Hz, 1H), 7.68 (d, J=8.1 Hz, 1H), 7.66-7.61 (m, 1H), 7.57 (dd, J=8.1, 1.1 Hz, 1H), 7.48 (td, J=7.7, 1.3 Hz, 1H), 5.96 (s, 1H), 3.23 (s, 3H), 2.97 (ddd, J=12.1, 10.4, 5.5 Hz, 1H), 2.82 (ddd, J=12.2, 10.3, 5.9 Hz, 1H), 2.28 (t, J=7.3 Hz, 2H), 1.77-1.61 (m, 2H), 1.61-1.54 (m, 2H), 1.39-1.29 (m, 2H); $^{13}$C NMR (126 MHz, CD$_3$OD) δ 177.2, 144.5, 142.5, 141.4, 137.9, 136.8, 134.8, 133.4, 129.1, 128.8, 128.5, 127.1, 98.0, 67.7, 48.2, 39.7, 34.4, 26.9, 26.7, 25.3.

3-((3-Chloro-6-methyl-5,5-dioxido-6,11-dihydrod-ibenzo[c,f][1,2]thiazepin-11-yl)amino)propanoic acid hydrochloride salt (7h)

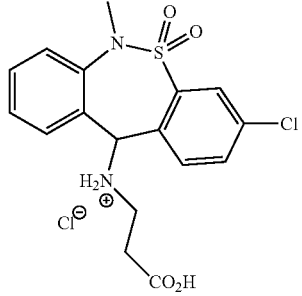

7h

The product 7h was prepared according to the general procedure and obtained as a glassy, white foam (364 mg, 98%). $^1$H NMR (400 MHz, CD$_3$OD) 8.09 (d, J=2.2 Hz, 1H), 7.94 (d, J=8.3 Hz, 1H), 7.87 (dd, J=8.2, 2.2 Hz, 1H), 7.77 (dd, J=7.8, 1.4 Hz, 1H), 7.69-7.63 (m, 1H), 7.60 (dd, J=8.1, 1.3 Hz, 1H), 7.49 (td, J=7.6, 1.4 Hz, 1H), 6.02 (s, 1H), 3.30-3.25 (m, 1H), 3.28 (s, 3H), 3.12 (dt, J=18.3, 6.4 Hz, 1H), 2.84-2.68 (m, 2H); $^{13}$C NMR (101 MHz, CD$_3$OD) δ 174.2, 142.3, 142.1, 139.0, 137.1, 135.1, 134.7, 133.6, 129.5, 129.3, 128.3, 127.8, 127.4, 68.1, 44.3, 39.4, 30.7.

5-((3-Chloro-6-methyl-5,5-dioxido-6,11-dihydrod-ibenzo[c,f][1,2]thiazepin-11-yl)amino)pentanoic acid hydrochloride salt (7i)

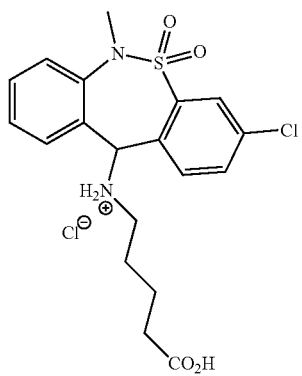

7i

The product 7i was prepared according to the general procedure and obtained as a glassy, off-white foam (243 mg, 98%). $^1$H NMR (400 MHz, CD$_3$OD) δ 8.09 (d, J=2.1 Hz, 1H), 7.92 (d, J=8.2 Hz, 1H), 7.87 (dd, J=8.2, 2.2 Hz, 1H), 7.74 (dd, J=7.8, 1.4 Hz, 1H), 7.68-7.62 (m, 1H), 7.58 (dd, J=8.1, 1.3 Hz, 1H), 7.49 (td, J=7.6, 1.4 Hz, 1H), 5.98 (s, 1H), 3.24 (s, 3H), 3.00 (ddd, J=12.3, 9.6, 5.9 Hz, 1H), 2.86 (ddd, J=12.3, 9.6, 6.3 Hz, 1H), 2.31 (t, J=7.0 Hz, 2H), 1.82-1.64 (m, 2H), 1.64-1.54 (m, 2H); $^{13}$C NMR (101 MHz, CD$_3$OD) δ 176.71, 142.51, 141.87, 138.84, 137.07, 135.19, 134.78, 133.50, 129.42, 129.16, 128.53, 127.88, 127.08, 67.61, 48.07, 39.71, 33.83, 26.40, 22.70.

Example 2. Opioid Receptor Activity

The diarylthiazepinamine esters (6) and carboxylic acids (7) were tested for agonist activity at the human mu-opioid receptor (MOR) and delta-opioid receptor (DOR) using bioluminescence resonance energy transfer (BRET) assays measuring G protein activation as previously described (Table 1) (Rives, M.-L. et al. 2012; Negri, A. et al. 2013).

Transfection.

Human MOR or DOR cDNA was transfected alongside Gα$_{oB}$ with RLuc8 inserted at position 91 (Gα$_{oB}$—RLuc8), Gβ$_1$ (β$_1$), and Gγ$_2$ fused to the full-length mVenus at its N terminus (mVenus-γ2) into HEK-293T cells (5×10$^6$ cells/plate) in 10-cm dishes using PEI (Polysciences Inc.; Warrington, Pa.) in a 1:1 ratio diluted in Opti-MEM (Life Technologies Corp.; Grand Island, N.Y.) to assay for G protein activation as described previously (Rives, M.-L. et al. 2012; Negri, A. et al. 2013). Cells were maintained in Dulbecco's Modified Eagle Medium (high glucose #11965; Life Technologies) supplemented with 10% FBS (Premium Select, Atlanta Biologicals; Atlanta, Ga.) and 100 U/mL penicillin and 100 μg/mL streptomycin (#15140, Life Technologies). After 24 hours the media was changed, and the experiment was performed 24 hours later (48 hours after transfection).

BRET.

Transfected cells were dissociated and re-suspended in phosphate-buffered saline (PBS). Approximately 200,000 cells/well were added to a black-framed, white well 96-well plate (#60050; Perkin Elmer; Waltham, Mass.). The microplate was centrifuged and the cells were re-suspended in PBS. Then 5 μM of the luciferase substrate coelenterazine H was added to each well for 5 minutes. Following coelenterazine H addition, ligands were added and the BRET signal was measured at 5 minutes on a PHERAstar FS plate reader. Quantification of the BRET signal required calculating the ratio of the light emitted by the energy acceptor, mVenus (510-540 nm), over the light emitted by the energy donor, RLuc8 (485 nm). This drug-induced BRET signal was normalized using the E$_{max}$ of [D-Ala, N-MePhe, Gly-ol]-enkephalin (DAMGO) or [D-Pen(2,5)]Enkephalin (DP-DPE) as the 100% maximal response for G protein activation at MOR or DOR, respectively (Rives, M.-L. et al. 2012; Negri, A. et al. 2013). Dose response curves were fit using a three-parameter logistics equation in GraphPad Prism 6.

The following compounds listed in Table 1 activated human MOR and/or DOR. Accordingly, the compounds listed in Table 1 are agonists of MOR and/or DOR.

TABLE 1

Functional agonist activity of compounds at human MOR and DOR.

| Compound | Structure | Human MOR (EC$_{50}$) | Human DOR (EC$_{50}$) |
| --- | --- | --- | --- |
| Tianeptine | 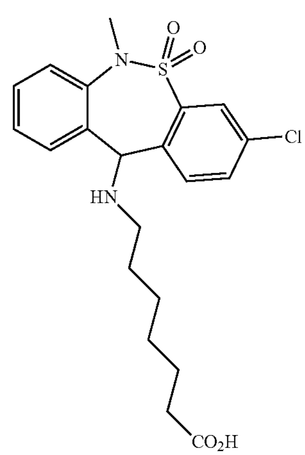 [SMILES: CN1c2ccccc2C(NCCCCCCC(=O)O)c2ccc(Cl)cc2S1(=O)=O] | 194 ± 70 nM | 37.4 ± 11.2 μM |
| 6a | 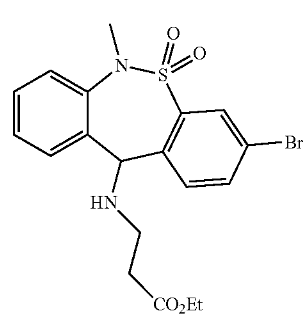 [SMILES: CCOC(=O)CCNC1c2ccccc2N(C)S(=O)(=O)c2cc(Br)ccc21] | 5.9 ± 1.0 μM | >10 μM |

TABLE 1-continued

Functional agonist activity of compounds at human MOR and DOR.

| Compound | Structure | Human MOR (EC$_{50}$) | Human DOR (EC$_{50}$) |
|---|---|---|---|
| 6b | 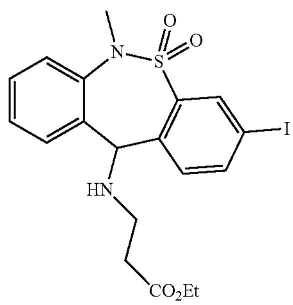 [SMILES: CCOC(=O)CCNC1c2ccccc2N(C)S(=O)(=O)c2cc(I)ccc21] | 1.6 ± 0.2 μM | >10 μM |
| 6c | 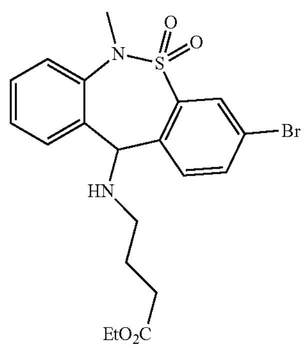 [SMILES: CCOC(=O)CCCNC1c2ccccc2N(C)S(=O)(=O)c2cc(Br)ccc21] | 270 ± 38 nM | >10 μM |
| 6i | 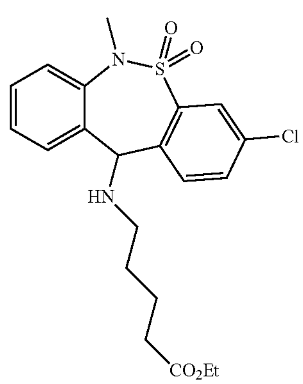 [SMILES: CCOC(=O)CCCCNC1c2ccccc2N(C)S(=O)(=O)c2cc(Cl)ccc21] | 533 ± 267 nM | >10 μM |
| 6d | 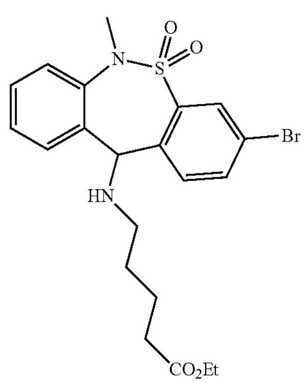 [SMILES: CCOC(=O)CCCCNC1c2ccccc2N(C)S(=O)(=O)c2cc(Br)ccc21] | 120 nM | 10 μM |

TABLE 1-continued
Functional agonist activity of compounds at human MOR and DOR.
| Compound | Structure | Human MOR (EC$_{50}$) | Human DOR (EC$_{50}$) |
|---|---|---|---|
| 6e | 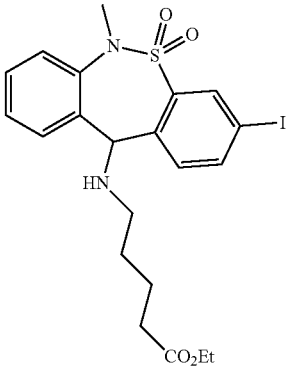 [SMILES: CCOC(=O)CCCCNC1c2ccccc2N(C)S(=O)(=O)c2cc(I)ccc21] | 28.2 ± 3.2 nM | 6.8 ± 0.03 µM |
| 6j | 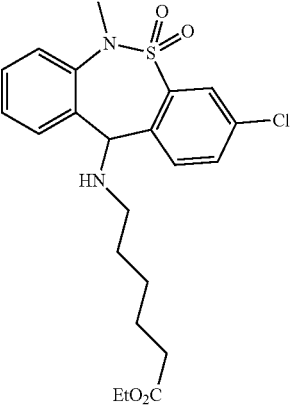 [SMILES: CCOC(=O)CCCCCNC1c2ccccc2N(C)S(=O)(=O)c2cc(Cl)ccc21] | 318 ± 162 nM | 13.9 ± 4.8 µM |
| 6f | 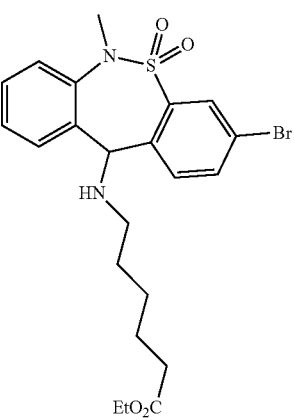 [SMILES: CCOC(=O)CCCCCNC1c2ccccc2N(C)S(=O)(=O)c2cc(Br)ccc21] | 90.8 ± 31.4 nM | 11.7 ± 0.06 µM |

TABLE 1-continued

Functional agonist activity of compounds at human MOR and DOR.

| Compound | Structure | Human MOR (EC$_{50}$) | Human DOR (EC$_{50}$) |
|---|---|---|---|
| 6g | 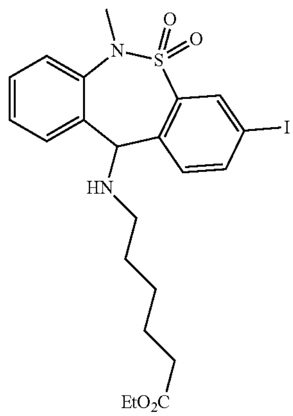 [SMILES: CCOC(=O)CCCCCNC1c2ccccc2N(C)S(=O)(=O)c2cc(I)ccc21] | 48.5 ± 4.9 nM | 8.5 ± 6.3 µM |
| 7h | 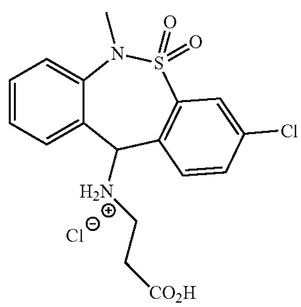 [SMILES: CN1c2ccccc2C([NH2+]CCC(=O)O)c2ccc(Cl)cc2S1(=O)=O ; [Cl-]] | 24.9 ± 12.6 µM | >10 µM |
| 7a | 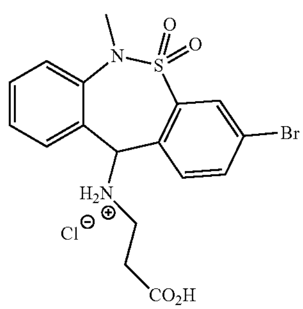 [SMILES: CN1c2ccccc2C([NH2+]CCC(=O)O)c2ccc(Br)cc2S1(=O)=O ; [Cl-]] | 4.7 ± 1.4 µM | >10 µM |
| 7b | 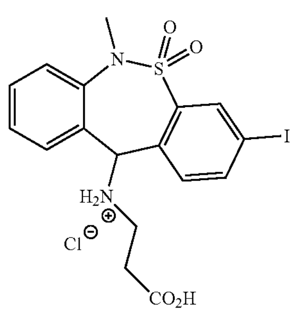 [SMILES: CN1c2ccccc2C([NH2+]CCC(=O)O)c2ccc(I)cc2S1(=O)=O ; [Cl-]] | 1.2 ± 0.3 µM | >10 µM |

TABLE 1-continued

Functional agonist activity of compounds at human MOR and DOR.

| Compound | Structure | Human MOR (EC$_{50}$) | Human DOR (EC$_{50}$) |
| --- | --- | --- | --- |
| 7c | 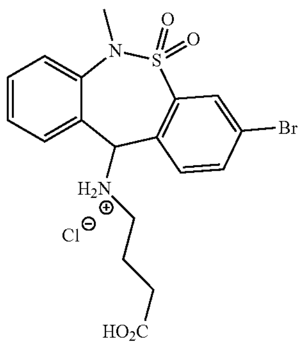 [SMILES: CN1c2ccccc2C([NH2+]CCCC(=O)O)c2ccc(Br)cc2S1(=O)=O ; [Cl-]] | 2.0 ± 0.3 μM | >10 μM |
| 7i | 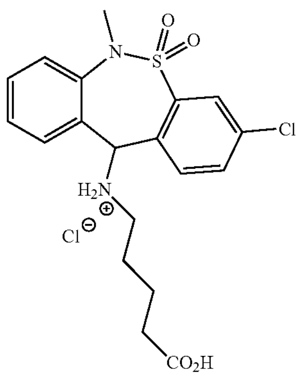 [SMILES: CN1c2ccccc2C([NH2+]CCCCC(=O)O)c2ccc(Cl)cc2S1(=O)=O ; [Cl-]] | 361.2 ± 92.9 nM | >10 μM |
| 7d | 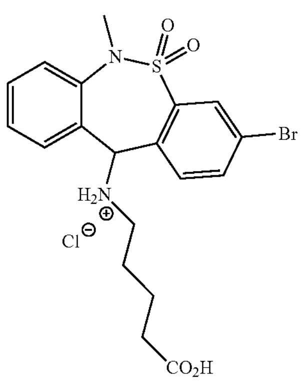 [SMILES: CN1c2ccccc2C([NH2+]CCCCC(=O)O)c2ccc(Br)cc2S1(=O)=O ; [Cl-]] | 405 nM | >10 μM |
| 7e | 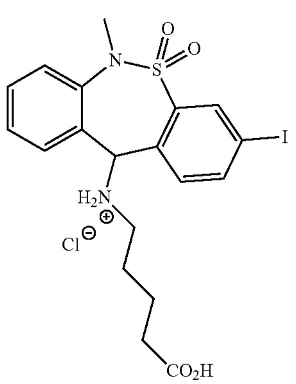 [SMILES: CN1c2ccccc2C([NH2+]CCCCC(=O)O)c2ccc(I)cc2S1(=O)=O ; [Cl-]] | 18.3 ± 0.2 nM | 8.9 ± 0.007 μM |

TABLE 1-continued

Functional agonist activity of compounds at human MOR and DOR.

| Compound | Structure | Human MOR (EC$_{50}$) | Human DOR (EC$_{50}$) |
|---|---|---|---|
| 7f | [structure with Br substituent] | 133 ± 13.2 nM | 23.7 ± 1.5 μM |
| 7g | [structure with I substituent] | 24.3 ± 4.5 nM | 5.1 ± 1.4 μM |

Where indicated, error represents ± SEM of 2 or more independent trials. The data shows the strong trend for increasing potency as the size of the halogen substituent is increased from chloro through iodo, a trend that holds across several example subgenera.

The data contained herein shows the strong trend for increasing potency as the size of the halogen substituent is increased from chloro through iodo. The compounds disclosed herein have increasing potency based on the following trend: X=Cl<X=Br<X=I. The compounds where X=I or X=Br have increased potency relative to the corresponding compounds where X=Cl.

Example 3. Administration of MOR Agonists

An amount of any one of compounds 6a, 6b, 6c, 6d, 6e, 6f, 6g, 7a, 7b, 7c, 7d, 7e, 7f, or 7g is administered to a subject afflicted with depression. The amount of the compound is effective to treat the subject afflicted with depression or major depression.

An amount of any one of compounds 6a, 6b, 6c, 6d, 6e, 6f, 6g, 7a, 7b, 7c, 7d, 7e, 7f, or 7g is administered to a subject afflicted with pain. The amount of the compound is effective to treat the subject afflicted with pain.

An amount of any one of compounds 6a, 6b, 6c, 6d, 6e, 6f, 6g, 7a, 7b, 7c, 7d, 7e, 7f, or 7g is administered to a subject afflicted with anxiety. The amount of the compound is effective to treat the subject afflicted with anxiety.

An amount of any one of compounds 6a, 6b, 6c, 6d, 6e, 6f, 6g, 7a, 7b, 7c, 7d, 7e, 7f, or 7g is administered to a subject afflicted with a mood or depressive disorder. The amount of the compound is effective to treat the subject afflicted with the disorder.

An amount of any one of compounds 6a, 6b, 6c, 6d, 6e, 6f, 6g, 7a, 7b, 7c, 7d, 7e, 7f, or 7g is administered to a subject afflicted with a borderline personality disorder. The amount of the compound is effective to treat the subject afflicted with the disorder.

An amount of any one of compounds 6a, 6b, 6c, 6d, 6e, 6f, 6g, 7a, 7b, 7c, 7d, 7e, 7f, or 7g is administered to a subject afflicted with a opioid addiction, opioid withdrawal symptoms, opioid induce respiratory depression or opioid overdose. The amount of the compound is effective to treat the subject afflicted with the opioid addiction, opioid withdrawal symptoms, opioid induce respiratory depression or opioid overdose.

Example 4. Metabolism and Pharmacokinetics

Experimental Protocol for PK Studies.

The brain pharmacokinetics of tianeptine and its 5-carbon metabolite (7i) were determined by Sai Life Sciences Limited (Hinjewadi, India) as follows in male C57BL/6 mice following a single administration of tianeptine. A group of male mice were administered with a solution formulation of tianeptine (normal saline with 7.5% NMP and 5% Solutol HS) intraperitoneally at a dose of 30 mg/kg. Brain samples were collected from three mice at 0.08, 0.25, 0.5, 1, 2, 4, 8 and 24 h, homogenized using ice-cold phosphate buffer saline (pH 7.4), and stored below −70° C. until analysis. Total homogenate volume was three times the tissue weight. All samples were processed for analysis by protein precipitation using acetonitrile (ACN) and analyzed with a fit-for-purpose LC/MS/MS method (LLOQ—1.01 ng/mL in brain). Pharmacokinetic parameters were calculated using the non-compartmental analysis tool of Phoenix WinNonlin® (Version 6.3).

Tianeptine is known to be metabolized primarily by R-oxidation of the carboxylic acid side chain, in a manner similar to fatty acids (Grislain, L. et al. 1990). This results in metabolites with shortened carboxylic acid side chains. In the specific case of tianeptine, these metabolites include compounds 7h and 7i. Other carboxylic acid analogs, including the compounds described in the present disclosure, are expected to be metabolized in a similar manner. Surprisingly, the 5-carbon metabolite (7i) resulting from degradation of tianeptine exhibits a significantly longer half-life and greater brain exposure (as measured by AUC) compared to the parent compound (Table 2). Accordingly, the shortened carboxylic acid analogs of this application (where X is Br or I), in addition to their higher potency, are expected to exhibit improved pharmacokinetics, and thus enhanced therapeutic efficacy over tianeptine and analogs of tianeptine where Cl is replaced with Br or I. Further, the specific length of the side chain selected is useful for fine control of the pharmacokinetic profile in this genus.

TABLE 2

Pharmacokinetic parameters of tianeptine and the resulting 5-carbon metabolite (7i) in the brains of C57BL/6 mice following a single injection (30 mg/kg, i.p.) of tianeptine.

| Compound | Route | Dose (mg/kg) | Matrix | $T_{max}$ (h) | $C_{max}$ (ng/g) | $AUC_{last}$ (h * ng/g) | $T_{1/2}$ (h) | CL (mL/min/kg) |
|---|---|---|---|---|---|---|---|---|
| tianeptine | i.p. | 30 | brain | 0.08 | 1019 | 351 | 0.29 | 1417 |
| 7i | — | — | brain | 0.5 | 2865 | 5963 | 2.33 | 78 |

Example 5. Esters as Prodrugs

Carboxylate esters are well known as prodrugs for the corresponding carboxylic acids obtained by hydrolysis (Beaumont, et al. 2003). Such ester prodrugs show improved oral bioavailability, better brain penetration, and/or longer duration of action compared to their carboxylic acid counterparts. Accordingly, compounds of this application having an ester side chain (6), although biologically active on their own, may also act as prodrugs for the corresponding carboxylic acids (7). Further, one skilled in the art will be able to apply the methods and knowledge of this application to prepare additional prodrugs. For example, the type of ester (e.g. methyl, ethyl, propyl, isopropyl, tert-butyl, phenyl) or the length of the side chain may be varied to adjust the activity and pharmacokinetic properties of the prodrugs and their corresponding carboxylic acid hydrolysis products.

Example 6. Combinations With NMDA Receptor Antagonists

Antagonists of the N-methyl-D-aspartate receptor (NMDAR) are known to potentiate the beneficial effects of opioid receptor agonists in the treatment of pain and to prevent development of tolerance to those effects (Trujillo, K. A. et al. 1994; Mao, J. et al. 1996). NMDAR antagonists are also known to be effective in the treatment of depression (Murrough, J. W. et al. 2013). Therefore, pharmaceutical compositions of the compounds disclosed herein, combined with NMDAR antagonists, are useful in the treatment of pain or mood disorders. Alternatively, the opioid modulator and NMDAR antagonist may be dosed separately, as a novel method for treating pain or mood disorders.

The pharmaceutical compositions of the compounds of the present invention, combined with NMDAR antagonists, are useful in the treatment of borderline personality disorder, opioid addiction, or opioid withdrawal symptoms, where the NMDAR antagonist serves as an adjunct to prevent the development of tolerance to the compounds of the present invention with chronic use.

NMDAR antagonists are also known to be effective in the treatment of depression (Murrough, J. W. et al. 2013; Zarate, C. A. Jr et al. 2006). Therefore, pharmaceutical compositions of the compounds of the present invention, combined with NMDAR antagonists, treat depressive disorders or other mood disorders with enhanced efficacy compared to the compounds of the present invention alone. Alternatively, the opioid modulator and NMDAR antagonist may be dosed separately, as a novel method for treating the conditions described above.

Non-Limiting Examples of NMDA Receptor Antagonists

Dextromorphinans—dextromethorphan, dextrorphan, dextrallorphan

Adamantanes—memantine, amantadine, rimantadine, nitromemantine (YQW-36)

Arylcyclohexylamines—ketamine (and its analogs, e.g. tiletamine), phencyclidine (and its analogs, e.g. tenocyclidine, eticyclidine, rolicyclidine), methoxetamine (and its analogs), gacyclidine (GK-11);

Miscellaneous—neramexane, lanicemine (AZD6765), diphenidine, dizocilpine (MK-801), 8a-phenyldecahydroquinoline (8A-PDHQ), remacemide, ifenprodil, traxoprodil (CP-101,606), eliprodil (SL-82.0715), etoxadrol (CL-1848C), dexoxadrol, WMS-2539, NEFA, delucemine (NPS-1506), aptiganel (Cerestat; CNS-1102), midafotel (CPPene; SDZ EAA 494), dexanabinol (HU-211 or ETS2101), selfotel (CGS-19755), 7-chlorokynurenic acid (7-CKA), 5,7-dichlorokynurenic acid (5,7-DCKA), L-683344, L-689560, L-701324, GV150526A, GV196771A, CERC-301 (formerly MK-0657), atomoxetine, LY-235959, CGP 61594, CGP 37849, CGP 40116 (active enantiomer of CG 37849), LY-233536, PEAQX (NVP-AAM077), ibogaine, noribogaine, Ro 25-6981, GW468816, EVT-101, indantadol, perzinfotel (EAA-090), SSR240600, 2-MDP (U-23807A), AP-7

Example 7. Combinations With NMDA Receptor Partial Agonists

Weak partial agonists of NMDAR are also known (Moskal, J. R. et al. 2005), and may be expected to produce beneficial or synergistic effects similar to an antagonist when intrinsic glutamate signaling activity is high or overactivated. Therefore, pharmaceutical compositions of the novel compounds disclosed herein, combined with NMDAR partial agonists, are useful in the treatment of pain or mood disorders. Alternatively, the opioid modulator and NMDAR partial agonist may be dosed separately, as a novel method for treating pain or mood disorders.

Pharmaceutical compositions of the compounds of the present invention, combined with NMDAR partial agonists, may be useful in the treatment of borderline personality disorder, opioid addiction, or opioid withdrawal symptoms, where the NMDAR partial agonist serves as an adjunct to prevent the development of tolerance to the compounds of the present invention with chronic use. Similarly, pharmaceutical compositions of the compounds of the present invention, combined with NMDAR partial agonists, treat depressive disorders or other mood disorders with enhanced efficacy compared to the compounds of the present invention alone. Alternatively, the opioid modulator and NMDAR partial agonist may be dosed separately, as a novel method for treating the conditions described above.

Non-Limiting Examples of NMDA Receptor Partial Agonists

NRX-1074, rapastinel (GLYX-13)

Example 8. Combinations with Neurokinin 1 Receptor Antagonists

Antagonists of the neurokinin 1 receptor (NK-1) are known to modulate the effects of opioid agonists, specifically in reward and self-administration protocols. More specifically, NK-1 antagonists attenuate opioid reward and self-administration in animal models (Robinson, J. E. et al. 2012). NK-1 antagonists are also known to be effective in the treatment of depression (Kramer, M. S. et al. 2004). Therefore, pharmaceutical compositions of the novel compounds disclosed herein, combined with NK-1 antagonists, are useful in the treatment of pain or mood disorders with increased efficacy and less potential for abuse. Alternatively, the opioid modulator and NK-1 antagonist may be dosed separately, as a novel method for treating pain or mood disorders.

Pharmaceutical compositions of the compounds of the present invention, combined with NK-1 antagonists, are useful in the treatment of depressive disorders, borderline personality disorder, opioid addiction, or opioid withdrawal, where the NK-1 antagonist serves as an adjunct to reduce the abuse potential of the compounds of the present invention. NK-1 antagonists are also known to be effective in the treatment of depression (Kramer, M. S. et al. 2004). Therefore, pharmaceutical compositions of the compounds of the present invention, combined with NK-1 antagonists, treat depressive disorders or other mood disorders with enhanced efficacy compared to the compounds of the present invention alone. Alternatively, the opioid modulator and NK-1 antagonist may be dosed separately, as a novel method for treating the conditions described above.

Non-Limiting Examples of Neurokinin 1 Receptor Antagonists aprepitant, fosaprepitant, casopitant, maropitant, vestipitant, vofopitant, lanepitant, orvepitant, ezlopitant, netupitant, rolapitant, L-733060, L-703606, L-759274, L-822429, L-760735, L-741671, L-742694, L-732138, CP-122721, RPR-100893, CP-96345, CP-99994, TAK-637, T-2328, CJ-11974, RP 67580, NKP608, VPD-737, GR 205171, LY686017, AV608, SR140333B, SSR240600C, FK 888, GR 82334

Example 9. Combinations With Neurokinin 2 Receptor Antagonists

Antagonists of the neurokinin 2 receptor (NK-2) are known to show antidepressant effects and to synergize with tricyclic antidepressants (Overstreet, D. H. et al. 2010). Therefore, pharmaceutical compositions of the novel compounds disclosed herein, combined with NK-2 antagonists, are useful in the treatment of mood disorders with increased efficacy. Alternatively, the opioid modulator and NK-2 antagonist may be dosed separately, as a novel method for treating mood disorders.

Pharmaceutical compositions of the compounds of the present invention, combined with NK-2 antagonists, are useful in the treatment of depressive disorders with increased efficacy compared to the compounds of the present invention alone. Alternatively, the opioid modulator and NK-2 antagonist may be dosed separately, as a novel method for treating depressive disorders.

Non-Limiting Examples of Neurokinin 2 Receptor Antagonists saredutant, ibodutant, nepadutant, GR-159897, MEN-10376

Example 10. Combinations With Neurokinin 3 Receptor Antagonists

Antagonists of the neurokinin 3 receptor (NK-3) are known to show antidepressant effects (Salome, et al. 2006).

Further, the actions of NK-3 modulators show a dependency on the opioid receptor system (Panocka, I. et al. 2001). Therefore, pharmaceutical compositions of the novel compounds disclosed herein, combined with NK-3 antagonists, are useful in the treatment of mood disorders with increased efficacy. Alternatively, the opioid modulator and NK-3 antagonist may be dosed separately, as a novel method for treating mood disorders.

Pharmaceutical compositions of the compounds of the present invention, combined with NK-3 antagonists, may be useful in the treatment of depressive disorders with increased efficacy compared to the compounds of the present invention alone. Alternatively, the opioid modulator and NK-3 antagonist may be dosed separately, as a novel method for treating depressive disorders.

Non-Limiting Examples of Neurokinin 3 Receptor Antagonists osanetant, talnetant, SB-222200, SB-218795

Example 11. Combinations With DOR Agonists

DOR Agonists have also been shown to elicit antidepressant effects (Torregrossa, et al. 2005). Therefore, pharmaceutical compositions of the novel compounds disclosed herein, combined with DOR agonists, are useful in the treatment of mood disorders with increased efficacy. Alternatively, the opioid modulator and DOR agonist may be dosed separately, as a novel method for treating mood disorders.

DOR Agonists have been shown to elicit antidepressant and anxiolytic effects (Saitoh, A. et al. 2004; Torregrossa, et al. 2005; Jutkiewicz, E. M. 2006) and are analgesic (Vanderah, T. W. 2010; Peppin, J. F. and Raffa, R. B. 2015). They have also been shown to reverse the respiratory depression induced by MOR agonists (Su, Y-F. et al. 1998). Therefore, pharmaceutical compositions of the compounds of the present invention, combined with DOR agonists, are useful in the treatment of depression, borderline personality disorder, pain, opioid-induced respiratory depression, or opioid overdose with increased efficacy or reduced side effects compared to the compounds of the present invention alone. Alternatively, the opioid modulator and DOR agonist may be dosed separately, as a novel method for treating the conditions described above.

Non-Limiting Examples of DOR Agonists tianeptine, (+)BW373U86, SNC-80, SNC-121, SNC-162, DPI-287, DPI-3290, DPI-221, TAN-67, KN-127, AZD2327, JNJ-20788560, NIH11082, RWJ-394674, ADL5747, ADL5859, UFP-512, AR-M100390, SB-235863, 7-spiroindanyloxymorphone.

Example 12. Combinations with DOR Antagonists

DOR antagonists have been shown in animals to attenuate several negative side effects exhibited by MOR agonists. For example, DOR antagonists slow the development of tolerance to the analgesic effects of morphine and also limit physical dependence (Hepburn, M. J. et al. 1997; Suzuki, T. et al. 1997). Further, DOR antagonists have been shown to attenuate the abuse liability of MOR agonists as determined by both conditioned place preference and self-administration paradigms (Suzuki, T. et al. 1994; Martin, T. J. et al. 2000). Therefore, pharmaceutical compositions of the compounds of the present invention, combined with DOR antagonists, may be useful in the treatment of depression, mood disorders, anxiety disorders, borderline personality disorder, pain, opioid addiction, or opioid withdrawal symptoms, where the DOR antagonist serves as an adjunct to prevent the development of tolerance to the compounds of the present invention or to reduce their abuse potential. Additionally, DOR antagonists have been shown to reverse the respiratory depression induced by MOR agonists (Su, Y-F. et al. 1998). Therefore, pharmaceutical compositions of the compounds of the present invention, combined with DOR antagonists, are useful in the treatment of opioid-induced respiratory depression or opioid overdose with enhanced efficacy compared to the compounds of the present invention alone. Alternatively, the opioid modulator and DOR antagonist may be dosed separately, as a novel method for treating the conditions described above.

Non-Limiting Examples of DOR Antagonists naltrindole, naltriben, N-benzylnaltrindole, 7-benzylidenenaltrexone, SDM25N, DPI-2505

Example 13. Combinations with SSRI or SNRIs

Selective serotonin reuptake inhibitors (SSRIs) and serotonin-norepinephrine reuptake inhibitors (SNRIs) are the standard of care for a many depressive disorders and mood disorders (Thase, M. E. 2008; Vaswani, M. et al. 2003). They are also useful in the treatment of chronic pain (Marks, D. M. et al. 2009). Therefore, pharmaceutical compositions of the compounds of the present invention, combined with SSRIs or SNRIs, are useful in the treatment of depressive disorders, mood disorders, borderline personality disorder, or pain with increased efficacy compared to the compounds of the present invention alone. Alternatively, the opioid modulator and SSRI or SNRI may be dosed separately, as a novel method for treating the conditions described above. Further, the compound of the present invention may be used as an add-on therapy to enhance the efficacy of preexisting SSRI or SNRI therapy for the conditions described above.

Non-Limiting Examples of SSRIs citalopram, escitalopram, fluoxetine, fluvoxamine, paroxetine, sertraline, dapoxetine Non-Limiting Examples of SNRIs venlafaxine, desvenlafaxine Example 14. Combination with Naloxone Naloxone is an MOR antagonist that is effective in blockading all behavioral effects induced by classical MOR agonists and is the standard treatment for opioid overdose. It is highly bioavailable by parenteral routes of administration but not by the oral route (Smith, K. et al. 2012). Accordingly, pharmaceutical compositions containing mixtures of an MOR agonist and naloxone remain effective when given by the oral route but the naloxone component inhibits the effects of the MOR agonist component when the mixture is administered parenterally. Thus, addition of naloxone to pharmaceutical compositions containing MOR agonists is useful for preventing their misuse or abuse by parenteral routes of administration. Therefore, pharmaceutical compositions of the compounds of the present invention, combined with naloxone, are useful in providing the therapeutic benefits of the compounds of the present invention while having diminished potential for abuse.

Example 15. Combinations with Methylnaltrexone

Constipation is a frequent, unpleasant side effect of MOR agonists resulting from inhibition of intestinal smooth muscle contractions via activation of MORs located in this tissue. Methylnaltrexone (Relistor) is a clinically approved quaternary ammonium salt of the opioid receptor antagonist naltrexone that does not cross the blood brain barrier. Accordingly, this compound is capable of inhibiting MORs in the gastrointestinal tract and preventing opioid-induced constipation while avoiding simultaneous inhibition of centrally mediated therapeutic effects. Therefore, pharmaceutical compositions of the compounds of the present invention, combined with methylnaltrexone, are useful in the treatment of depressive disorders, mood disorders, borderline personality disorder, pain, opioid addiction, or opioid withdrawal symptoms with reduced constipation compared to the compounds of the present invention alone. Alternatively, the opioid modulator and methylnaltrexone may be dosed separately, as a novel method for treating the conditions described above with less constipation.

DISCUSSION

The compounds disclosed herein activate MOR or dually activate MOR and DOR. Therefore, they are useful as analgesics. Furthermore, this activity leads to antidepressant effects, either directly, or via indirect modulation of the glutamatergic system. Accordingly, the compounds disclosed herein are also useful as antidepressants or anxiolytics.

Compounds of the present invention are advantageous compared to tianeptine due to their higher potency, which allows reduced dosing to treat a subject and thus, less probability for idiosyncratic toxicity due to off target effects. The compounds of the present invention are also advantageous compared to tianeptine in that they are longer lasting in vivo (longer half-life). Accordingly, the compounds of the present invention can replace tianeptine therapy with reduced side effects and reduced dosing frequency, i.e. one or two times daily as compared to three times daily for tianeptine.

An additional aspect of the invention provides synthetic methods and chemical intermediates that may be used to encompass chemical space around the diarythiazepinamine core structure.

REFERENCES

Barbier, E. et al. *Neuropsychopharmacology* 2013, 38, 976-984.
Bart, G. J. Addict. Dis. 2012, 31, 207-25.
Beaumont, K.; Webster, R.; Gardner, I.; Dack, K. *Curr. Drug Metab.* 2003, 4, 461-485.
Berrocoso, E.; Sánchez-Blázquez, P.; Garzón, J.; Mico, J. A. *Curr. Pharm. Des.* 2009, 15, 1612-1622.
Besson, A.; Privat, A. M.; Eschalier, A.; Fialip, J. *Psychopharmacology* 1996, 123, 71-78.
Bodkin, J. A.; Zornberg, G. L.; Lukas, S. E.; Cole, J. O. *J. Clin. Psychopharmacol.* 1995, 15, 49-57.
Buchwald, S. L.; Huang, X.; Zim, D. Ligands for metals and improved metal-catalyzed processes based thereon. US2004/171833 A1, 2004.
Corbett, A. D.; Henderson, G.; McKnight, A. T.; Paterson, S. J.; Brit. J. Pharmacol. 2006, 147, S153-S162.
David, D. J. et al. *Neuron* 2009, 62, 479-493.
Dreher, S. D.; Lim, S.-E.; Sandrock, D. L.; Molander, G. A. *J. Org. Chem.* 2009, 74, 3626-3631.
Durand, P.; Richard, P.; Renaut, P. *J. Org. Chem.* 1998, 63, 9723-9727.
Gassaway, M. M.; Rives, M-L.; Kruegel A. C.; Javitch, J. A.; Sames, D. *Transl. Psychiatry* 2014, 4, e411.
Gilleron, P.; Wlodarczyk, N.; Houssin, R.; Farce, A.; Laconde, G.; Goossens, J.-F.; Lemoine, A.; Pommery, N.; Hénichart, J.-P.; Millet, R. *Bioorg. Med. Chem. Lett.* 2007, 17, 5465-5471.
Grislain, L.; Gele, P.; Bertrand, M.; Luijten, W.; Bromet, N.; Salvadori, C.; Kamoun, A. *Drug Metab. Dispos.* 1990, 18, 804-808.
Hepburn, M. J. et al. *J. Pharmacol. Exp. Ther.* 1997, 281, 1350-1356.
Invernizzi, R.; Pozzi, L.; Garattini, S.; Samanin, R. *Neuropharmacology* 1992, 31, 221-227.
Jutkiewicz, E. M. *Mol. Interv.* 2006, 6, 162-169.
Kramer, M. S. et al. *Neuropsychopharmacology* 2004, 29, 385-392.
Mao, J.; Price, D. D.; Caruso, F. S.; Mayer, D. *J. Pain* 1996, 67, 361-368.
Martin, T. J. et al. *J. Pharmacol. Exp. Ther.* 2000, 294, 975-982.
McNeill, E.; Barder, T. E.; Buchwald, S. L. *Org. Lett.* 2007, 99, 3785-3788.
Moskal, J. R. Et al. *Neuropharmacology* 2005, 49, 1077-1087.
Murrough, J. W.; Iosifescu, D. V.; Chang, L. C.; Al Jurdi, R. K.; Green, C. E.; Perez, A. M.; Iqbal, S.; Pillemer, S.; Foulkes, A.; Shah, A.; Charney, D. S.; Mathew, S. *J. Am. J. Psychiatry* 2013, 170, 1134-1142.
Negri, A. Et al. *J. Chem. Inf. Model.* 2013, 53 (3), 521-526.
Overstreet, D. H. Et al. *Pharmacol. Biochem. Behav.* 2010, 96, 206-210.
Rives, M.-L. et al. *J. Biol. Chem.* 2012, 287 (32), 27050-27054.
Robinson, J. E. et al. *Psychopharmacology* 2012, 220, 215-224.
Pan, J.; Wang, X.; Zhang, Y.; Buchwald, S. L. *Org. Lett.* 2011, 13, 4974-4976.
Panocka, I. et al. *Peptides* 2001, 22, 1037-1042.
Pattinson, K. T. S. *Br. J. Anaesth.* 2008, 100, 747-758.
Paul, I. A.; Skolnick, P. *Ann. N. Y. Acad. Sci.* 2003, 1003, 250-272.
Peppin, J. F.; Raffa, R. B. *J. Clin. Pharm. Ther.* 2015, 40, 155-166.
Prossin, A. R.; Love, T. M.; Koeppe, R. A.; Zubieta, J-K.; Silk, K. R. *Am. J. Psychiatry* 2010, 167, 925-933.
Saitoh, A. et al. *J. Pharmacol. Sci.* 2004, 95, 374-380.
Salome, N.; Stemmelin, J.; Cohen, C.; Griebel, G. *Pharmacol. Biochem. Behav.* 2006, 83, 533-539.
Sansone, R. A.; Whitecar, P.; Wiederman, M. W. *Int. J. Psychiatry Med.* 2008, 38, 217-226.
Smith, K. et al. *Int. J. Clin. Pharmacol. Ther.* 2012, 50, 360-367.
Su, Y. F.; McNutt, R. W.; Chang, K. J. *J. Pharmacol. Exp. Ther.* 1998, 287, 815-823.
Suzuki, T. et al. *Jpn. J. Pharmacol.* 1994, 66, 131-137.
Suzuki, T. et al. *Pharmacol. Biochem. Behav.* 1997, 57, 293-299.
Svoboda, K. R.; Adams, C. E.; Lupica, C. R.; *J. Neurosci.* 1999, 19, 85-95.
Thase, M. E. *Psychopharmacol. Bull.* 2008, 41, 58-85.

Torregrossa, M. M. et al. *Psychopharmacology* (Berl). 2005, 183(1), 31-40.
Trujillo, K. A.; Akil, H. *Brain Res.* 1994, 633, 178-188.
Uy, R.; Yang, L.; Zhou, H.; Price, S. C.; You, W. *Macromolecules* 2011, 44, 9146-9154.
Vanderah, T. W. *Clin. J. Pain.* 2010, 26 Suppl, S10-15.
Vaswani, M.; Linda, F. K.; Ramesh, S. *Prog. Neuropsychopharmacol. Biol. Psychiatry* 2003, 27, 85-102.
Wermeling, D. P. *Ther. Adv. Drug Saf.* 2015, 6, 20-31.
Williams, J. T. et al. *Pharmacol. Rev.* 2013, 65, 223-254.
Xie, C. W., Lewis D. V. *J. Neurophysiol.* 1997, 78: 759-766.
Zarate, C. A. Jr et al. *Arch. Gen. Psychiatry* 2006, 63, 856-864.

What is claimed is:

1. A compound having the structure:

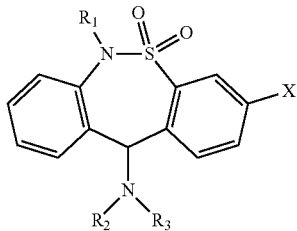

wherein
$R_1$ is —H or -(alkyl);
$R_2$ is —($C_2$-$C_5$ alkyl)-$CO_2$H or —$C_2$-$C_5$ alkyl)-$CO_2$-(alkyl);
$R_3$ is —H or -(alkyl); and
X is —Br or —I,
or a pharmaceutically acceptable salt or ester thereof.

2. The compound of claim 1,
wherein
$R_1$ is —H or -(alkyl);
$R_2$ is —($C_2$-$C_5$ alkyl)-$CO_2$H or —($C_2$-$C_5$ alkyl)-$CO_2$-(alkyl);
$R_3$ is —H or -(alkyl); and
X is —I,
or a pharmaceutically acceptable salt or ester thereof.

3. The compound of claim 1,
wherein
$R_1$ is —H, —$CH_3$ or —$CH_2CH_3$; and $R_3$ is —H, —CH or —$CH_2CH_3$,
or a pharmaceutically acceptable salt or ester thereof.

4. The compound of claim 1,
wherein
$R_2$ is —($C_2$ alkyl)-$CO_2$H, —($C_3$ alkyl)-$CO_2$H, —($C_4$ alkyl)-$CO_2$H, or ($C_5$ alkyl)-$CO_2$H, —$C_2$ alkyl)-$CO_2CH_2CH_3$, —($C_3$ alkyl)-$CO_2CH_2CH_3$, —($C_4$ alkyl)-$CO_2CH_2CH_3$, or —($C_5$ alkyl)-$CO_2CH_2CH_3$; and
$R_3$ is —H,
or a pharmaceutically acceptable salt or ester thereof.

5. The compound of claim 1,
wherein
$R_1$ is -(alkyl);
$R_2$ is —($C_2$-$C_5$ alkyl)-$CO_2$H or —($C_2$-$C_5$ alkyl)-$CO_2$-(alkyl);
$R_3$ is —H; and
X is —Br or —I,
or a pharmaceutically acceptable salt or ester thereof.

6. The compound of claim 5,
wherein
$R_1$ is -(alkyl);
$R_2$ is —($C_2$-$C_5$ alkyl)-$CO_2$H or —($C_2$-$C_5$ alkyl)-$CO_2CH_2CH_3$;
$R_3$ is —H; and
X is —I,
or a pharmaceutically acceptable salt or ester thereof.

7. The compound of claim 1 having the structure:

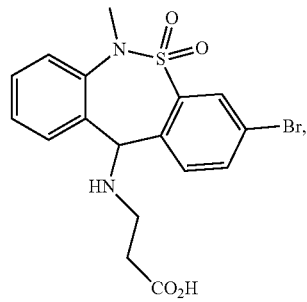

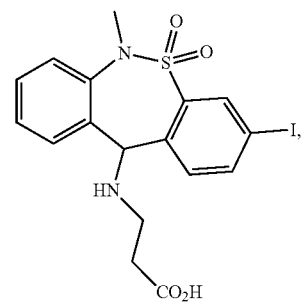

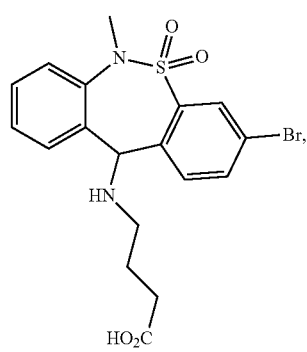

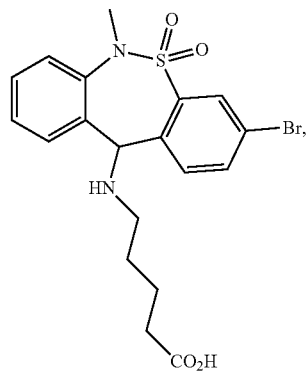

131
-continued
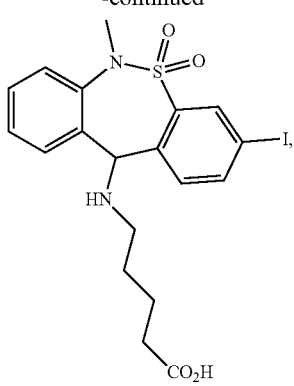
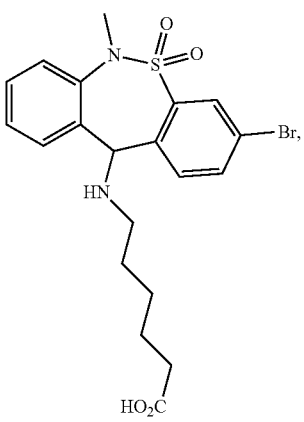
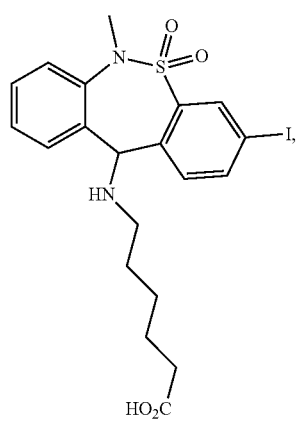
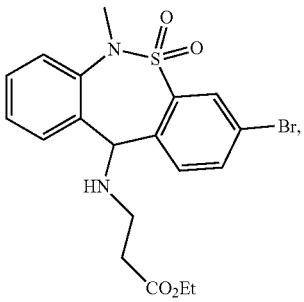
132
-continued
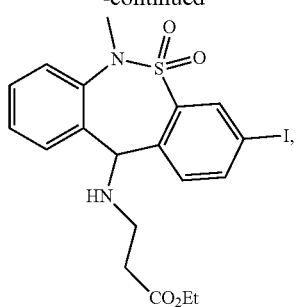
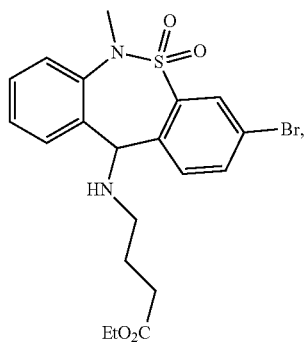
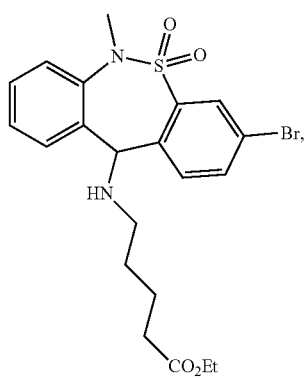
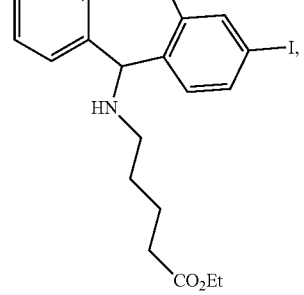

-continued
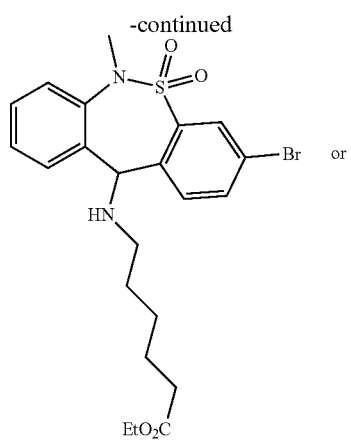
Br or
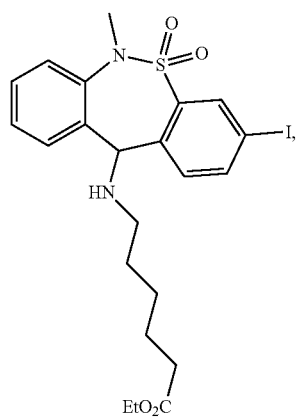
I,
or a pharmaceutically acceptable salt or ester thereof.
8. The compound of claim 1 having the structure:
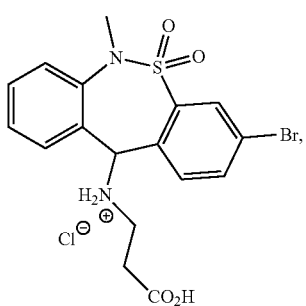
Br,
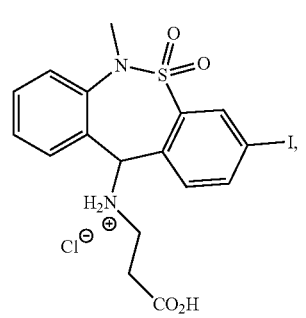
I,
-continued
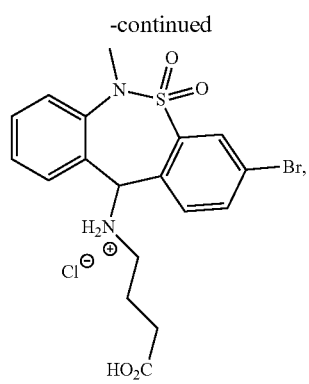
Br,
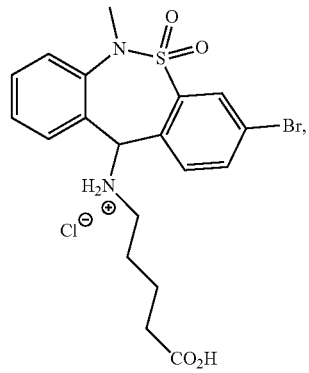
Br,
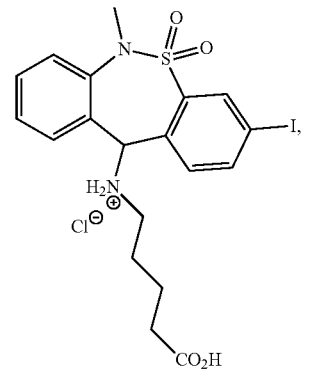
I,
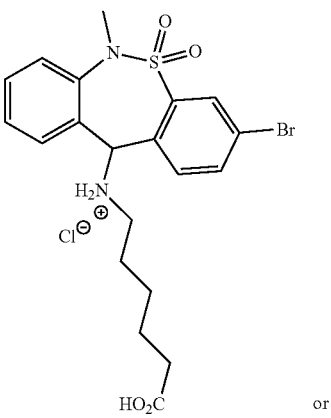
Br or -continued

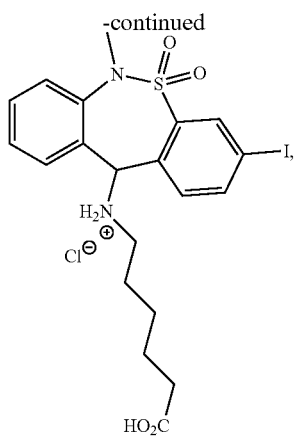

or an ester thereof.

9. A pharmaceutical composition comprising the compound of claim 1 and a pharmaceutically acceptable carrier.

10. A method of activating a mu-opioid receptor or delta-opioid receptor comprising contacting the mu-opioid receptor or delta-opioid receptor with the compound of claim 1.

11. A method of treating a subject afflicted with pain, a depressive disorder or a mood disorder comprising administering an effective amount of the compound of claim 1 to the subject so as to treat the subject afflicted with pain, the depressive disorder or the mood disorder.

12. A method of treating a subject afflicted with borderline personality disorder, opioid addiction, opioid withdrawal symptoms, opioid-induced respiratory depression or opioid overdose comprising administering an effective amount of the compound of claim 1 to the subject so as to treat the subject afflicted with the borderline personality disorder, opioid addiction, opioid withdrawal symptoms, opioid-induced respiratory depression or opioid overdose.

13. A method of treating a subject afflicted with a pain, a depressive disorder or a mood disorder comprising administering to the subject an effective amount of a NMDA receptor antagonist, an NMDA receptor partial agonist, a neurokinin 1 receptor antagonist, a neurokinin 2 receptor antagonist, a neurokinin 3 receptor antagonist or a DOR agonist and an effective amount of the compound of claim 1 so as to thereby treat the subject afflicted with pain, the depressive disorder or the mood disorder, or
of treating a subject afflicted with a pain, a depressive disorder or a mood disorder comprising administering to the subject an effective amount of a DOR antagonist and an effective amount of the compound of claim 1 so as to thereby treat the subject afflicted with pain, the depressive disorder or the mood disorder, or
of treating a subject afflicted with borderline personality disorder comprising administering to the subject an effective amount of a NMDA receptor antagonist, an NMDA receptor partial agonist, a neurokinin 1 receptor antagonist, a DOR agonist or a DOR antagonist and an effective amount of the compound of claim 1 so as to thereby treat the subject afflicted with the borderline personality disorder, or
of treating a subject afflicted with opioid addiction or opioid withdrawal symptoms comprising administering to the subject an effective amount of a NMDA receptor antagonist, an NMDA receptor partial agonist, a neurokinin 1 receptor antagonist or a DOR antagonist and an effective amount of the compound of claim 1 so as to thereby treat the subject afflicted with the opioid addiction or opioid withdrawal symptoms, or
of treating a subject afflicted with opioid overdose comprising or opioid-induced respiratory depression administering to the subject an effective amount of a DOR agonist or a DOR antagonist and an effective amount of the compound of claim 1 so as to thereby treat the subject afflicted with the opioid overdose or opioid-induced respiratory depression.

14. A method of treating a subject afflicted with opioid overdose, opioid addiction or opioid withdrawal symptoms comprising administering to the subject an effective amount of naloxone or methylnaltrexone and an effective amount of the compound of claim 1 so as to thereby treat the subject afflicted with the opioid overdose, opioid addiction or opioid withdrawal symptoms.

15. A method of treating a subject afflicted with pain, a depressive disorder, a mood disorder, borderline personality disorder or opioid-induced respiratory depression, comprising administering to the subject an effective amount of naloxone or methylnaltrexone and an effective amount of the compound of claim 1 so as to thereby treat the subject afflicted with pain, the depressive disorder, mood disorder, borderline personality disorder or opioid-induced respiratory depression.

16. A pharmaceutical composition comprising the compound of claim 1, a NMDA receptor antagonist, an NMDA receptor partial agonist, a neurokinin 1 receptor antagonist, a neurokinin 2 receptor antagonist, a neurokinin 3 receptor antagonist, a DOR agonist, a DOR antagonist, naloxone or methylnaltrexone and a pharmaceutically acceptable carrier.

17. A process for producing the compound of claim 1 having the structure:

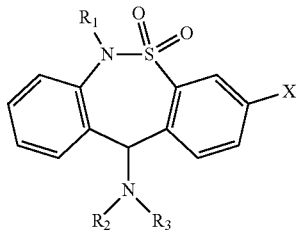

wherein
$R_1$ is —H or -(alkyl);
$R_2$ is —($C_2$-$C_5$ alkyl)-$CO_2H$ or —($C_2$-$C_5$ alkyl)-$CO_2$-(alkyl);
$R_3$ is —H or -(alkyl); and
X is —Br or —I,
comprising
(a) contacting the compound having the structure:

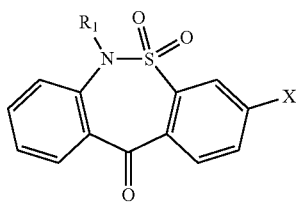

with a reducing agent in a first suitable solvent to produce a compound having the structure:

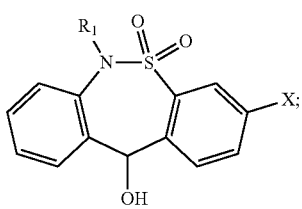

(b) reacting the product of step (a) with a halogenating agent, tosylating agent or triflating agent in a second suitable solvent so as to produce a compound having the structure:

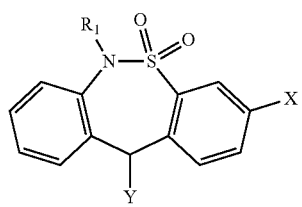

wherein Y is OTs, OTf, Cl, Br, or I; and (c) reacting the product of step (b) with an amine of the formula HNR$_2$R$_3$ in the presence of a base in a third suitable solvent so as to produce the compound having the structure:

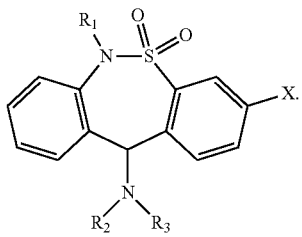

18. The compound of claim 1,
wherein
R$_1$ is —H or -(alkyl);
R$_2$ is —(C$_4$-C$_5$ alkyl)-CO$_2$H or —(C$_4$-C$_5$ alkyl)-CO$_2$-(alkyl);
R$_3$ is —H or -(alkyl); and
X is —I,
or a pharmaceutically acceptable salt or ester thereof.

19. The compound of claim 1,
wherein
R$_1$ is —H or -(alkyl);
R$_2$ is —(C$_4$-C$_5$ alkyl)-CO$_2$H or —(C$_4$-C$_5$ alkyl)-CO$_2$-(alkyl);
R$_3$ is —H or -(alkyl); and
X is —Br,
or a pharmaceutically acceptable salt or ester thereof.

20. The compound of claim 1 having the structure:

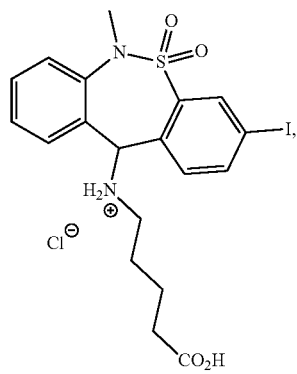 [SMILES: CN1c2ccccc2C([NH2+]CCCCC(=O)O)c2ccc(I)cc2S1(=O)=O ; [Cl-]]

or ester thereof, or

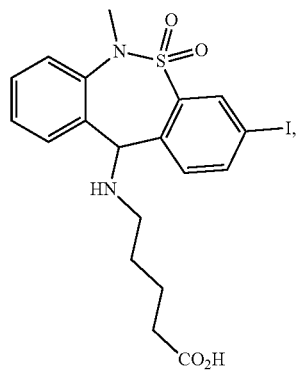 [SMILES: CN1c2ccccc2C(NCCCCC(=O)O)c2ccc(I)cc2S1(=O)=O]

or a pharmaceutically acceptable salt or ester thereof.

21. The compound of claim 1 having the structure:

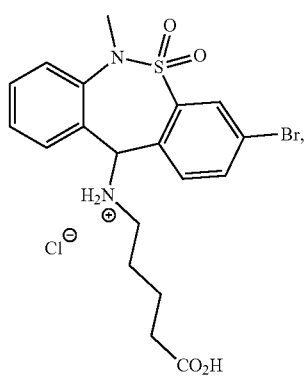 [SMILES: CN1c2ccccc2C([NH2+]CCCCC(=O)O)c2ccc(Br)cc2S1(=O)=O ; [Cl-]]

or ester thereof, or
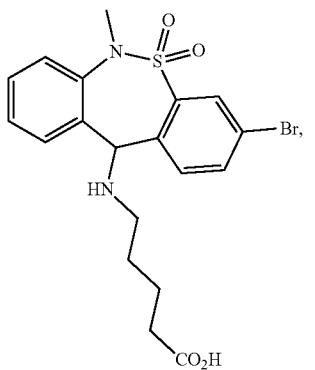 [SMILES: CN1c2ccccc2C(NCCCCC(=O)O)c2ccc(Br)cc2S1(=O)=O]
or a pharmaceutically acceptable salt or ester thereof.
* * * * *